(12) United States Patent
Cohen

(10) Patent No.: US 10,357,669 B2
(45) Date of Patent: *Jul. 23, 2019

(54) COMPOSITION CONTAINING A CELLULOSE DERIVED CAPSULE WITH A SUNSCREEN

(71) Applicant: CoLabs International Corporation, Las Vegas, NV (US)

(72) Inventor: Laura E. Cohen, Huntington Beach, CA (US)

(73) Assignee: CoLabs International Corporation, Las Vegas ( * ) Notice: Subject to any disclaimer, the term of this patent is extended or adjusted under 35 U.S.C. 154(b) by 0 days.

This patent is subject to a terminal disclaimer.

(21) Appl. No.: 15/796,631

(22) Filed: Oct. 27, 2017

(65) Prior Publication Data

US 2018/0042829 A1 Feb. 15, 2018

Related U.S. Application Data

(63) Continuation of application No. 15/264,285, filed on Sep. 13, 2016, now Pat. No. 10,098,823, which is a continuation of application No. 14/072,926, filed on Nov. 6, 2013, now Pat. No. 9,456,966.

(60) Provisional application No. 61/769,758, filed on Feb. 27, 2013, provisional application No. 61/722,870, filed on Nov. 6, 2012.

(51) Int. Cl.

| | | |
|---|---|---|
| A61Q 17/04 | (2006.01) | |
| A61K 8/49 | (2006.01) | |
| A61K 8/19 | (2006.01) | |
| A61K 8/46 | (2006.01) | |
| A61Q 17/02 | (2006.01) | |
| A61K 8/44 | (2006.01) | |
| C09B 69/10 | (2006.01) | |
| C09B 67/02 | (2006.01) | |
| A61K 8/35 | (2006.01) | |
| A61K 8/37 | (2006.01) | |
| A61K 8/06 | (2006.01) | |
| A61K 8/73 | (2006.01) | |
| A61Q 5/12 | (2006.01) | |
| A61K 8/11 | (2006.01) | |
| A61Q 19/10 | (2006.01) | |
| A61Q 5/02 | (2006.01) | |
| A61Q 17/00 | (2006.01) | |
| A61Q 19/00 | (2006.01) | |
| A61Q 5/06 | (2006.01) | |

(52) U.S. Cl.
CPC .............. *A61Q 17/04* (2013.01); *A61K 8/062* (2013.01); *A61K 8/11* (2013.01); *A61K 8/19* (2013.01); *A61K 8/35* (2013.01); *A61K 8/37* (2013.01); *A61K 8/445* (2013.01); *A61K 8/466* (2013.01); *A61K 8/494* (2013.01); *A61K 8/498* (2013.01); *A61K 8/4926* (2013.01); *A61K 8/731* (2013.01); *A61Q 5/02* (2013.01); *A61Q 5/06* (2013.01); *A61Q 5/12* (2013.01); *A61Q 17/02* (2013.01); *A61Q 19/007* (2013.01); *A61Q 19/10* (2013.01); *C09B 67/0097* (2013.01); *C09B 69/109* (2013.01); *A61K 2800/21* (2013.01); *A61K 2800/412* (2013.01); *A61K 2800/60* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 1,478,208 | A | 12/1923 | Duddleson et al. |
| 3,462,479 | A | 8/1969 | Strobel et al. |
| 3,691,270 | A | 9/1972 | Charle et al. |
| 4,402,977 | A | 9/1983 | Grollier et al. |
| 4,540,507 | A | 9/1985 | Grollier |
| 4,542,125 | A | 9/1985 | Gorman et al. |
| 4,663,155 | A | 5/1987 | Murray et al. |
| 4,663,156 | A | 5/1987 | Clum et al. |
| 4,683,134 | A | 7/1987 | Palinczar |
| 4,686,099 | A | 8/1987 | Palinczar |
| 4,699,779 | A | 10/1987 | Palinczar |
| 4,701,321 | A | 10/1987 | Bernstein |
| 4,749,501 | A | 6/1988 | Nakagawa et al. |
| 4,803,195 | A | 2/1989 | Holzner |
| 4,874,538 | A | 10/1989 | Dawson et al. |
| 4,904,524 | A | 2/1990 | Yoh |

(Continued)

FOREIGN PATENT DOCUMENTS

| | | |
|---|---|---|
| CN | 1341012 A | 3/2002 |
| EP | 0025379 B1 | 6/1984 |

(Continued)

OTHER PUBLICATIONS

U.S. Appl. No. 14/072,926, filed Nov. 6, 2013, Nov. 6, 2012, US20140127275, U.S. Pat. No. 9,456,966.

(Continued)

*Primary Examiner* — John Pak
*Assistant Examiner* — Daniel L Branson
(74) *Attorney, Agent, or Firm* — UltimatEdge IP Law Group, P.C.; Dean G. Stathakis

(57) ABSTRACT

A sunscreen composition comprised of one or more sunscreen active agents encapsulated in a cellulose derived capsule wherein the composition can contain one or more additional agents. A sunscreen composition can be mixed with a bodywash, shampoo, conditioner, lotion, gel, soap, cream, hand sanitizer, spray or mousse and can be used by an individual during their normal hygiene processes, such as during a shower or bath or while applying a body product to their skin or hair.

23 Claims, No Drawings

(56) References Cited

U.S. PATENT DOCUMENTS

| | | |
|---|---|---|
| 4,933,174 A | 6/1990 | Bernstein |
| 4,985,170 A | 1/1991 | Dawson et al. |
| 5,071,706 A | 12/1991 | Soper et al. |
| 5,089,269 A | 2/1992 | Noda et al. |
| 5,132,117 A | 7/1992 | Speaker et al. |
| 5,169,624 A | 12/1992 | Ziegler et al. |
| 5,292,801 A | 3/1994 | Avnir et al. |
| 5,300,564 A | 4/1994 | Avnir et al. |
| 5,306,485 A | 4/1994 | Robinson et al. |
| 5,455,048 A | 10/1995 | Lahmani et al. |
| 5,476,660 A | 12/1995 | Somasundaran et al. |
| 5,508,259 A | 4/1996 | Holzner et al. |
| 5,543,136 A | 8/1996 | Aldous |
| 5,589,177 A | 12/1996 | Herb et al. |
| 5,614,217 A | 3/1997 | Chiprich et al. |
| 5,599,555 A | 4/1997 | El-Nokaly |
| 5,620,692 A | 4/1997 | Potter et al. |
| 5,643,341 A | 7/1997 | Hirsch et al. |
| 5,661,189 A | 8/1997 | Grieveson et al. |
| 5,674,912 A | 10/1997 | Martin |
| 5,683,716 A | 11/1997 | Hata et al. |
| 5,716,920 A | 2/1998 | Glenn et al. |
| 5,733,531 A | 3/1998 | Mitchnick et al. |
| 5,759,524 A | 6/1998 | Tanner et al. |
| 5,770,556 A | 6/1998 | Farrell et al. |
| 5,785,979 A | 7/1998 | Wells |
| 5,849,273 A | 12/1998 | Bonda et al. |
| 5,876,755 A | 2/1999 | Perring et al. |
| 5,900,394 A | 5/1999 | Goel et al. |
| 5,904,917 A | 5/1999 | Mattai et al. |
| 5,914,101 A | 6/1999 | Tapley et al. |
| 5,948,416 A | 9/1999 | Wagner et al. |
| 5,955,409 A | 9/1999 | Farrell et al. |
| 5,989,529 A | 11/1999 | Kaplan |
| 5,989,536 A | 11/1999 | Deckner et al. |
| 6,024,942 A | 2/2000 | Tanner et al. |
| 6,043,204 A | 3/2000 | Kaufman et al. |
| 6,057,275 A | 5/2000 | Fair et al. |
| 6,074,630 A | 6/2000 | Devillez et al. |
| 6,096,697 A | 8/2000 | Wells |
| 6,110,888 A | 8/2000 | Lupo, Jr. et al. |
| 6,159,453 A | 12/2000 | Avnir et al. |
| 6,217,852 B1 | 4/2001 | Gildengerg et al. |
| 6,224,852 B1 | 5/2001 | Morgan et al. |
| 6,238,650 B1 | 5/2001 | Lapidot et al. |
| 6,248,364 B1 | 6/2001 | Sengupta et al. |
| 6,248,703 B1 | 6/2001 | Finucane et al. |
| 6,255,264 B1 | 7/2001 | Fleurot et al. |
| 6,303,149 B1 | 10/2001 | Magdassi et al. |
| 6,348,218 B1 | 2/2002 | Hed et al. |
| 6,362,146 B1 | 3/2002 | Macaulay |
| 6,391,287 B1 | 5/2002 | Baldo et al. |
| 6,395,269 B1 | 5/2002 | Fuller et al. |
| 6,399,045 B1 | 6/2002 | Morgan et al. |
| 6,412,658 B1 | 7/2002 | Bartholomew et al. |
| 6,436,375 B1 | 8/2002 | Lapidot et al. |
| 6,468,509 B2 | 10/2002 | Lapidot et al. |
| 6,471,975 B1 | 10/2002 | Banovetz et al. |
| 6,485,713 B1 | 11/2002 | Bonda et al. |
| 6,491,902 B2 | 12/2002 | Shefer et al. |
| 6,500,791 B2 | 12/2002 | Pereira et al. |
| 6,524,594 B1 | 2/2003 | Santora et al. |
| 6,555,095 B1 | 4/2003 | Garrison |
| 6,576,228 B1 | 6/2003 | Crookham et al. |
| 6,607,713 B1 | 8/2003 | Chodorowski et al. |
| 6,696,067 B2 | 2/2004 | Brandt et al. |
| 6,699,824 B1 | 3/2004 | Dawson et al. |
| 6,740,631 B2 | 5/2004 | Shefer et al. |
| 6,770,270 B2 | 8/2004 | Bonda |
| 6,825,161 B2 | 11/2004 | Shefer et al. |
| 6,855,335 B2 | 2/2005 | Seok et al. |
| 6,913,825 B2 | 7/2005 | Ostafin et al. |
| 6,998,113 B1 | 2/2006 | Traynor et al. |
| 7,001,592 B1 | 2/2006 | Traynor et al. |
| 7,025,952 B1 | 4/2006 | Traynor et al. |
| 7,037,513 B1 | 5/2006 | Traynor et al. |
| 7,053,034 B2 | 5/2006 | Shefer et al. |
| 7,074,747 B1 | 7/2006 | Lukenbach et al. |
| 7,098,032 B2 | 8/2006 | Trubetskoy et al. |
| 7,138,382 B2 | 11/2006 | Wolff et al. |
| 7,226,582 B2 | 6/2007 | Traynor et al. |
| 7,226,607 B2 | 6/2007 | Uchiyama et al. |
| 8,039,015 B2 | 10/2011 | Speaker |
| 2002/0028235 A1 | 3/2002 | Reed et al. |
| 2002/0034487 A1 | 3/2002 | Maubru et al. |
| 2002/0064541 A1 | 5/2002 | Lapidot et al. |
| 2002/0077256 A1 | 6/2002 | Niemiec et al. |
| 2002/0131939 A1 | 9/2002 | Djerassi et al. |
| 2002/0167404 A1 | 11/2002 | Jordan |
| 2003/0032593 A1 | 2/2003 | Wender et al. |
| 2003/0059382 A1 | 3/2003 | Brandt et al. |
| 2003/0059383 A1 | 3/2003 | SaNogueira et al. |
| 2003/0134761 A1 | 7/2003 | Sebillotte-Arnaud et al. |
| 2003/0147818 A1 | 8/2003 | Dubief et al. |
| 2003/0171230 A1 | 9/2003 | Shana'a et al. |
| 2003/0176303 A1 | 9/2003 | Niemiec et al. |
| 2003/0187665 A1 | 10/2003 | Boyd |
| 2004/0005278 A1 | 1/2004 | Reinhart et al. |
| 2004/0028709 A1 | 2/2004 | Dueva et al. |
| 2004/0101498 A1 | 5/2004 | Koshti et al. |
| 2004/0120905 A1 | 6/2004 | Gall et al. |
| 2004/0167046 A1 | 8/2004 | Lukenbach et al. |
| 2004/0169298 A1 | 9/2004 | Fukasawa et al. |
| 2004/0234558 A1 | 11/2004 | O'Conner et al. |
| 2004/0247543 A1 | 12/2004 | Huerta et al. |
| 2005/0065047 A1 | 3/2005 | Shefer et al. |
| 2005/0123611 A1 | 6/2005 | Barbe et al. |
| 2005/0255055 A1 | 11/2005 | Wagner et al. |
| 2006/0018966 A1 | 1/2006 | Lin et al. |
| 2006/0073106 A1 | 4/2006 | Berg-Schultz et al. |
| 2007/0028400 A1 | 2/2007 | Wolber et al. |
| 2007/0292676 A1 | 12/2007 | Naigertsik et al. |
| 2008/0112904 A1 | 5/2008 | Traynor et al. |
| 2008/0317795 A1 | 12/2008 | Traynor et al. |
| 2009/0280149 A1 | 11/2009 | Tajima et al. |
| 2009/0324655 A1 | 12/2009 | Polonka et al. |
| 2010/0015188 A1 | 1/2010 | Izu et al. |
| 2010/0092410 A1 | 4/2010 | Cockerell et al. |
| 2010/0135936 A1 | 6/2010 | Dueva-Koganov et al. |
| 2011/0020253 A1 | 1/2011 | Doyle et al. |
| 2011/0150795 A1 | 6/2011 | Loing et al. |
| 2011/0206793 A1 | 8/2011 | Hines et al. |
| 2012/0141395 A1 | 6/2012 | Chaudhuri et al. |
| 2012/0148644 A1 | 6/2012 | Popplewell et al. |
| 2012/0207804 A1 | 8/2012 | Traynor et al. |
| 2014/0127275 A1 | 8/2014 | Cohen |

FOREIGN PATENT DOCUMENTS

| | | |
|---|---|---|
| EP | 0254447 B1 | 3/1993 |
| EP | 0399911 B1 | 7/1993 |
| EP | 1162942 B1 | 6/2004 |
| WO | 1992016195 A1 | 10/1992 |
| WO | 199845036 A1 | 10/1998 |
| WO | 199943296 A2 | 11/1999 |
| WO | 200042985 A1 | 7/2000 |
| WO | 200057850 A1 | 10/2000 |
| WO | 2005009602 A2 | 2/2005 |
| WO | 2008144734 A1 | 11/2008 |
| WO | 2010000587 A2 | 1/2010 |
| WO | 2012074250 A2 | 6/2012 |
| WO | 2013087548 A2 | 6/2013 |
| WO | 2013107354 A1 | 7/2013 |
| WO | 2014074555 A1 | 5/2014 |
| WO | 2014132261 A2 | 9/2014 |
| WO | 2017139701 A1 | 8/2017 |

OTHER PUBLICATIONS

U.S. Appl. No. 14/269,127, filed May 3, 2014, Nov. 6, 2012, US20140242131, U.S. Pat. No. 9,456,967.

U.S. Appl. No. 14/269,129, filed May 3, 2014, Nov. 6, 2012, US20140255456, U.S. Pat. No. 9,468,591.

(56) References Cited

OTHER PUBLICATIONS

U.S. Appl. No. 14/269,131, filed May 3, 2014, Nov. 6, 2012, US20140242132, U.S. Pat. No. 9,456,968.
U.S. Appl. No. 14/702,615, filed May 1, 2015, Nov. 6, 2012, US20150231046, U.S. Pat. No. 9,592,184.
U.S. Appl. No. 15/264,285, filed Sep. 13, 2016, Nov. 6, 2012, US20170000697.
U.S. Appl. No. 15/264,300, filed Sep. 13, 2016, Nov. 6, 2012, US20170000698.
U.S. Appl. No. 15/796,616, filed Oct. 27, 2017, Nov. 6, 2012.
U.S. Appl. No. 15/796,627, filed Oct. 27, 2017, Nov. 6, 2012.
U.S. Appl. No. 15/430,416, filed Feb. 10, 2017, Nov. 6, 2012, US20170157021.
U.S. Appl. No. 15/490,812, filed Apr. 18, 2017, Nov. 6, 2012.
U.S. Appl. No. 15/490,815, filed Apr. 18, 2017, Nov. 6, 2012.
PCT Form ISA 210, International Search Report, PCT/US2018/017720, dated May 14, 2018.
PCT Form ISA 210, International Search Report, PCT/US2018/017722, dated Jun. 5, 2018.
PCT Form ISA 237, Written Opinion, PCT/US2018/017720, dated May 14, 2018.
PCT Form ISA 237, Written Opinion, PCT/US2018/017722, dated Jun. 5, 2018.
SANAR, website (2016).
Specos, et al., Microencapsulated Citronella Oil for Mosquito Repellent Finishing of Cotton Textiles, Trans. R. Soc. Trop. Med. Hyg. 104: 653-658 (2010).
Xiong, et al., Complex Coacervation of Ovalbumin-Carboxymethylcellulose Assessed by Isothermal Titration Calorimeter and Rheology: Effect of Ionic Strength and Charge Density of Polysaccharides, Food Hydrocolloids 73: 41-50 (2017).
Boissiere, et al. Turning Biopolymer Particles into Hybrid Capsules: the Example of Silica/Alginate Nanocomposites, J. Mater. Chem. 16: 1178-1182 (2006).
Business Wire, Leading Cosmetics Industry Chemist Joins Skin Innovator; Performance Brands Names Michael Dulak to Board of Directors (1999).
Copyrightkids.org, http://web.archive.org/web/20030919013921 /http://www.copyrightkids.org/definitions. html, Retrieved via WayBack Machine with archive date of Sep. 19, 2003.
Datachem Software Developers of CertiStep, License Agreements, http://web.archive.org/web/20031109074418/http://www.datachemsoftware.com/licenses.htm, retrieved via Wayback Machine with archive date of Nov. 9, 2003.
Donahue, Intellectual Property Licensing: A Crib Sheet for Deal Makers, http://teklaw.com/iplicens.htm (1998).

Donaldson, et al., Ultrafine Particles, Occup. Environ. Med., 58(3): 211-216 (2001).
Earth Supplied Products, LLC, ESP KERABEAD™ Avo/Octo Encap Product Specification.
Earth Supplied Products, LLC, ESP KERABEAD™ Shea Oil-20 Product Specification.
Earth Supplied Products, LLC, ESP KERABEAD™ Silicone-20 Product Specification.
Earth Supplied Products, LLC, ESP VEGABEAD™ OMC 40 Product Specification.
EMD Chemicals Inc., EUSOLEX® UV-PEARLS™ Product Information.
EPO, Supplemental Search Report, dated Apr. 15, 2016.
Ford, Sunscreen How Products Are Made, Find Articles at BNET, vol. 2, (1994), Retrieved from http://www.findarticles.com.
Ghosh, Functional Coatings and Microencapsulation: A General Perspective, in Functional Coatings, pp. 1-28 (Wiley-VCH Verlag GmbH & Co KgaA, Weinheim) 2006.
Karr, et al., A Novel Encapsulation of N,N-diethyl-3-methylbenzamide (DEET) Facorably Modifies Skin Absorption while Maintaining Effective Evaporation Rates, J. Controlled Release 160:502-508 (2012).
Klykken, et al., Silicone Film-Forming Technologies for Health Care Applications, Dow Corning [online] (2009).
Merck KGaA, EUSOLEX® T-AVO, website description page (2005).
Merck KGaA, EUSOLEX® UV-PEARLS™, website description page (2005).
PARSOL® 1789 Product Page.
PCT Form ISA 210, International Search Report, PCT/US2006/003365, dated May 24, 2006.
PCT Form ISA 237, Written Opinion, PCT/US2006/003365, dated May 24, 2006.
PCT Form ISA 210, International Search Report, PCT/US2013/068651, dated Mar. 5, 2014.
PCT Form ISA 237, Written Opinion, PCT/US2013/068651, dated Mar. 5, 2014.
PCT Form IB 373, International Preliminary Report on Patentability, PCT/US2013/068651, dated May 12, 2015.
PCT Form ISA 210, International Search Report, PCT/US2017/017556, dated Feb. 10, 2017.
PCT Form ISA 237, Written Opinion, PCT/US2017/017556, dated Feb. 10, 2017.
UCLA Trademarks and Licensing, http://web.archive.org/web/20030811091818/http://www.asucla.ucla.edu/licensing/index.asp, Retrieved via Wayback Machine with archive date of Aug. 11, 2003.
Yeh, et al. Synthesis of Hollow Silica Spheres with Mesostructed Shell Using Cationic-Anionic-Neutral Block Copolymer Ternary Surfactants, Langmuier 22(1): 6-9 (2006).

COMPOSITION CONTAINING A CELLULOSE DERIVED CAPSULE WITH A SUNSCREEN

This application is a continuation that claims priority pursuant to 35 U.S.C. § 120 to U.S. Non-Provisional Ser. No. 15/264,285, filed Sep. 13, 2016, a continuation that claims priority to U.S. Non-Provisional Ser. No. 14/072,926, filed Nov. 6, 2013, now U.S. Pat. No. 9,456,966, which claims priority pursuant to 35 U.S.C. § 119(e) to U.S. Provisional Patent Application 61/769,758, filed Feb. 27, 2013 and U.S. Provisional Patent Application 61/722,870, filed Nov. 6, 2012, each of which is hereby incorporated by reference in its entirety.

BACKGROUND

Overexposure to ultraviolet ("UV") radiation produced by the sun can result in deleterious effects to individuals, including, sunburn, premature aging of skin, premature wrinkling, and for many individuals, an increase in the risk of skin cancer. To avoid these adverse effects, it is common for individuals prior to exposure to sunlight to apply a sunscreen product to their skin. Such products are widely available and relatively inexpensive. However, many individuals fail to use them on a regular basis for reasons that include, without limitation, convenience of use and the feel of the product after application. Additionally, these products suffer from other issues such as uneven application and their inability to provide adequate protection due to loss of coverage suffered from such activities as swimming, exercise that results in perspiration and dermal penetration and subsequent excretion through the urine of the active agents incorporated in the sunscreen product that protects an individual from the sun's harmful UV radiation (hereinafter referred to as "sunscreen active agents").

To provide more convenient, consistent and even sunscreen protection, several products that are used by individuals on a regular basis have been developed that incorporate sunscreen active agents that protect an individual from the sun's harmful UV radiation. In the United States, it is common for individuals to bathe or shower on a regular basis, in most instances, every day. It is also common for those same individuals to use a body wash, shampoo, conditioner, lotion or cream while they shower. Therefore, products have been developed that include sunscreen active agents in bodywashes and shampoos. Other products that have been developed to include sunscreen active agents are make-up, lip balm and even hair spray products. Though the use of these products adds convenience, they generally have not overcome some of the other issues related to the use of sunscreen products.

Nevertheless, in spite of all the above attempts, there remains an unmet need for an effective sunscreen product that provides an effective level of sun protection, particularly a level of sun block or sunscreen that is higher than existing formulations and remains effective even after rinsing one or more times following application as well as having a gentle or acceptable feel on the human skin, as opposed to an oily feel. The present invention addresses one or more of these needs by utilizing encapsulation technologies, milder surfactant systems, and good adhesive polymers that provide a strong binding capability, making it more efficient for deposition of sunscreen. The present invention adds cellulose derived capsules that contain one or more sunscreen active agents, resulting in an increase in SPF in the formulation as compared to free sunscreen or non-encapsulated material.

The cellulose derived capsules of the present invention also lay down on the skin surface in a manner that result in a more even distribution and spreading of the sunscreen active agent over the skin of an individual. The cellulose derived capsules of the present invention also provide a means for formulating a sunscreen active agent that can result in a greater amount of sunscreen active agent after application through such products as shampoo, body wash, conditioner, lotion, mousse, spray, hand sanitizer, cream and gel.

SUMMARY

In an aspect, the present invention discloses a sunscreen composition comprising a sunscreen active agent encapsulated in a cellulose derived capsule and one or more additional agents. In a further aspect the present invention discloses that a sunscreen composition is combined with a bodywash, shampoo, conditioner, gel, soap, hand sanitizer, cream, spray, mousse or lotion. In an aspect, the present invention discloses that a sunscreen active agent included in a sunscreen composition absorbs or blocks UV radiation from about 290 to about 420 nm. In an aspect, the present invention discloses that a sunscreen active agent is an inorganic physical blocker of UVA solar radiation, an inorganic physical blocker of UVB solar radiation, an iron oxide or a polymer or a polyethylene.

In another aspect, the present invention discloses a sunscreen composition, wherein the composition comprises one, two, three, four or more sunscreen active agents. In a further aspect, the present invention discloses that the SPF protection provided by a sunscreen active agent in the composition is from about 1 to 70, is from about 1 to about 50, or about 2 to about 50, or about 2 to about 40, or about 2 to about 30, or about 2 to about 20, or about 2 to about 10, or about 2 to about 5, or about 5 to about 25, or about 5 to about 20, or about 5 to about 15, or about 5 to about 10. In another aspect the present invention discloses that the SPF protection provided by a sunscreen composition in the composition is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more and/or the SPF protection provided by a sunscreen composition in the composition remains above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more and/or the SPF protection provided by the composition lasts at least about 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 hours or more and/or the SPF protection provided by the composition lasts for an average of at least about about 1 day, 2 days, 3 days, 4 days, 5 days, 6 days, 7 days, 8 days, 9 days, 10 days, 11 days, 12 days, 13 days, 14 days, after rinsing.

In an aspect, the present invention discloses that the SPF protection provided by the composition increases after each additional application. In a further aspect, the present invention discloses that the SPF protection provided by the composition increases after each additional application so that after a second, third, fourth, fifth, sixth, seventh, eighth, ninth, tenth, eleventh or more washes, the SPF provided can be above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more.

In an aspect, the present invention discloses that a sunscreen composition includes a cationic polymer, and further, wherein the cationic polymer can be a quaternium or a polyquaternium. In a further aspect, the present invention discloses that a film former is dimethicone and/or petrolatum and/or a preservative is BHT and/or an additional agent is an antioxidant, a chelating agent, a liquid hydrocarbon, a foaming agent, a skin nourishing substance, sunless tanning actives, skin lightening actives, skin whitener, a hindered amine light stabilizers, anti-acne actives, anti-skin wrinkling and anti-skin aging actives, vitamins, anti-inflammatory actives, anesthetic actives, analgesic actives, anti-pruritic actives, anti-microbial actives (e.g. antifungals, antibacterials, and antiparasitics), anti-virals, anti-allergenics, medicinal actives (e.g., skin rash, skin disease and dermatitis medications), anti-cellulite additives, hindered amine light stabilizers, insect repellant actives, antioxidants, hair growth promoters, hair growth inhibitors, hair bleaching agents, vitamins, deodorant compounds, or more. In a further embodiment, sunless tanning actives include, without limitation, dihydroxyacetone (DHA); glyceryl aldehyde; tyrosine and tyrosine derivatives such as malyltyrosine, tyrosine glucosinate, and ethyl tyrosine; phospho-DOPA, indoles and derivatives. In a further embodiment, skin lightening actives include, without limitation, EMBLICA (also an antioxidant), monobenzone (a depigmenting agent), kojic acid, arbutin, ascorbic acid and derivatives thereof (e.g., magnesium ascorbyl phosphate or sodium ascorbyl phosphate), and extracts (e.g., mulberry extract, placental extract).

In an aspect, the present invention discloses that a composition is applied topically and/or sprayed. In an aspect, the present invention discloses that an additional agent is a surfactant and the surfactant can be cationic, anionic, nonionic, zwitterionic, amphoteric, or any combination thereof and/or organic or inorganic, further, wherein, a sunscreen composition can include an additional agent to treat a condition suffered by an individual. In a further aspect, the present invention discloses that a sunscreen composition can be used to treat Seborrheic dermatitis, eczema, xerosis, infestation, dyschromia, keratosis pilaris, acne, anti-aging, sensitive skin, ephilides, solar lentigines, photo sensitive disease, skin cancer and hx of skin cancer, melisma, auto immune, alopecia, fungal, bacterial, and viral infections, protect colored or treated hair, bromhidrosis, malodor, dandruff, wound healing, insect repellant, pet shampoo/skin care, lindane or similar conditions.

In an aspect, the present invention discloses that a sunscreen active agent is titanium dioxide and the titanium dioxide can have an anatase, ritile or amorphous structure and the titanium dioxide can be uncoated or coated and can be coated with aluminum compounds, including, without limitation, aluminum oxide, aluminum stearate or aluminum laurate or can be coated with phospholipids or silicone compounds. In a further aspect, the present invention discloses that titanium dioxide can be micronized and has a mean primary particle size ranging from about 10 nm to about 50 nm or a micronized mean primary particle size of 15 nm and/or the titanium dioxide is uncoated and if uncoated titanium dioxide can have a mean particle size of around 35 nm to about 50 nm. In a further aspect, the present invention discloses that a mixture of two or more different particle sizes of titanium dioxide and/or comprises a mixture of coated and uncoated titanium dioxide. In an aspect, the present invention discloses that a composition comprises a sunscreen active agent is encapsulated or two or more sunscreen active agents are encapsulated and/or a sunscreen composition comprises one or more sunscreen active agents.

In an aspect, the present invention discloses that the ratio of sunscreen composition to bodywash, shampoo, conditioner, lotion, gel, soap, cream, hand sanitizer, spray or mousse is about 0.2, 0.5, 0.7 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10; 12, 15, or 20 parts bodywash, shampoo, lotion, conditioner, gel, soap, hand sanitizer, cream, spray or mousse to sunscreen active agent as measured w/w.

In an aspect, the present invention discloses that the pH of the sunscreen composition is from about 6 to about 8, about 6.7 to about 7.5 or about 4.0 to about 10. In a further aspect, the present invention discloses that the pH of the composition is at least 1, 2, 3, 4, 5, 6, 7, 8, 9, 10, 11, 12, 13, or 14.

In an aspect, the present invention discloses that a cellulose derived capsule contains one sunscreen active agent or two or more sunscreen active agents and further, wherein the cellulose derived capsule can be flexible and further, wherein the cellulose derived capsule has a high load rate. In an aspect, the present invention discloses that a cellulose derived capsule is comprised of hydroxypropylcellulose, hydroxypropylmethylcellulose, ethylcellulose, carboxymethylcellulose or any derivatives therefrom and, wherein, the cellulose derived capsule can have a diameter of about 400 nm to about 700 nm. In an additional embodiment, a cellulose derived capsule has a diameter of about 400 nm to about 650 nm, about 400 nm to about 600 nm, about 400 nm to about 550 nm, about 400 nm to about 500 nm, about 400 nm to about 450 nm, about 200 nm to about 750 nm, about 250 nm to about 700 nm, 300 nm to about 600 nm or about 300 nm to about 700 nm. In a further embodiment, 75% or more of the cellulose derived capsules have a diameter of about 300 nm to about 600 nm. In a further embodiment, a cellulose derived capsule has a diameter of at least 25 nm, at least 50 nm, at least 75 nm, at least 100 nm, at least 125 nm, at least 150 nm, at least 175 nm, at least 200 nm, at least 225 nm, at least 250 nm, at least 275 nm, at least 300 nm, at least 325 nm, at least 350 nm, at least 375 nm, at least 400 nm, at least 425 nm, at least 450 nm, at least 475 nm, at least 500 nm, at least 525 nm, at least 550 nm, at least 575 nm, at least 600 nm, at least 625 nm, at least 650 nm, at least 675 nm, at least 700 nm, at least 725 nm, at least 750 nm, at least 775 nm, at least 800 nm, at least 825 nm, at least 850 nm, at least 875 nm, at least 900 nm, at least 925 nm, at least 950 nm, at least 975 nm, at least 1000 nm or more.

In an aspect, the present invention discloses that a sunscreen composition comprises water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients and further, wherein the sunscreen composition includes, without limitation, at least two, three, four, five, six, seven, eight, nine, ten, or more additional agents and further, wherein the additional agents can have a concentration that is from about 0.0001% to about 99.9% (w/v). In an aspect, the present invention discloses that one or more additional agents are encapsulated or one or more additional agents are not encapsulated. In an aspect, the present invention discloses that one or more additional agents are not encapsulated.

In an aspect, the present invention discloses that a sunscreen composition increases the protection of an individual to which the composition is applied. In a further aspect, the present invention discloses that the concentration of a sunscreen active agent that is a UVA or a UVB absorber is from of about 1% to about 40%, or about 2% to about 20%, or about 2% to about 10%, or about 5% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% (w/v). In a further aspect, the present invention discloses that a cellulose derived capsule is prepared so as to experience breakage in the range of about 0, 0.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95% to about 0.50.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95% after application or the cellulose derived capsule is prepared so as to experience breakage in response to conditions that occur on the skin or hair and can be in response to conditions that occur on the skin or hair in a time release or controlled manner. In an additional aspect, the present invention discloses that an additional agent is a vitamin that can be encapsulated in a cellulose derived capsule or not. In a further aspect, the present invention discloses that an additional agent is an anti-acne active that can be encapsulated in a cellulose derived capsule or not. In a further aspect, the present invention discloses that an additional agent is an anti-skin wrinkling active that can be encapsulated in a cellulose derived capsule or not. In a further aspect, the present invention discloses that an additional agent is a botox active that can be encapsulated in a cellulose derived capsule or not. In a further aspect, the present invention discloses that an additional agent is an anti-skin aging or anti-wrinkling active that can be encapsulated in a cellulose derived capsule or not and further, wherein anti-skin aging or anti-wrinkling additional agents can be a bicyclic aromatic compounds, compounds which have retinoid-type activity, free-radical scavengers, hydroxy or keto acids or derivatives thereof, further, wherein an anti-skin aging or anti-wrinkling additional agents are sulfur-containing D and L amino acids and their derivatives and salts, phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. In a further aspect, the present invention discloses that an additional agent is an anti-inflammatory active that can be encapsulated in a cellulose derived capsule or not. In a further aspect, the present invention discloses that an additional agent is anesthetic that can be encapsulated in a cellulose derived capsule or not. In a further aspect, the present invention discloses that an additional agent is an analgesic that can be encapsulated in a cellulose derived capsule or not. In a further aspect, the present invention discloses that an additional agent is an antimicrobial or antifungal that can be encapsulated in a cellulose derived capsule or not. In a further aspect, the present invention discloses that an additional agent is an anti-viral that can be encapsulated in a cellulose derived capsule or not. In a further aspect, the present invention discloses that an additional agent treats dermatological conditions that can be encapsulated in a cellulose derived capsule or not. In a further aspect, the present invention discloses that an additional agent is an anti-cellulite active that can be encapsulated in a cellulose derived capsule or not. In a further aspect, the present invention discloses that an additional agent treats hair loss that can be encapsulated in a cellulose derived capsule or not. In a further aspect, the present invention discloses that an additional agent is hair bleaching agent that can be encapsulated in a cellulose derived capsule or not. In a further aspect, the present invention discloses that an additional agent is a deodorant that can be encapsulated in a cellulose derived capsule or not. In a further aspect, the present invention discloses that an additional agent is an anti-oxidant active that can be encapsulated in a cellulose derived capsule or not. In a further aspect, the present invention discloses that an additional agent is photostable antioxidant that can be encapsulated in a cellulose derived capsule or not. In a further aspect, the present invention discloses that an additional agent is an insect repellent that can be encapsulated in a cellulose derived capsule or not. In a further aspect, the present invention discloses that an additional agent is a polyquaternium and/or a cationic active that can be encapsulated in a cellulose derived capsule or not. In a further aspect, the present invention discloses that an additional agent is film barrier system that can be encapsulated in a cellulose derived capsule or not. In a further aspect, the present invention discloses that an additional agent is a film former that can be encapsulated in a cellulose derived capsule or not. In a further aspect, the present invention discloses that an additional agent is a secondary film former that can be encapsulated in a cellulose derived capsule or not. In a further aspect, the present invention discloses that an additional agent is a preservative. In a further aspect, the present invention discloses that an additional agent is a chelating agent that can be encapsulated in a cellulose derived capsule or not. In a further aspect, the present invention discloses that an additional agent is a thickening agent or gellant that can be encapsulated in a cellulose derived capsule or not. In a further aspect, the present invention discloses that an additional agent is fragrance, dye and/or antimicrobial that can be encapsulated in a cellulose derived capsule or not. In a further aspect, the present invention discloses that an additional agent is a surfactant that can be encapsulated in a cellulose derived capsule or not. In an aspect, the surfactant results in reduced lathering or results in lathering and/or the surfactant is an anionic surfactant, a taurate, a nonionic surfactant, a ampohoteric lathering surfactant, a amphoteric surfactant or a cationic surfactant. In a further aspect, the present invention discloses that an additional agent is a quenching agent that can be encapsulated in a cellulose derived capsule or not. In a further aspect, the present invention discloses that an additional agent is a thickening agent or gellant that can be encapsulated in a cellulose derived capsule or not. In a further aspect, the present invention discloses that an additional agent is a hindered amine light stabilizers that can be encapsulated in a cellulose derived capsule or not. In a further aspect, the present invention discloses that an additional agent is a skin whitener that can be encapsulated in a cellulose derived capsule or not.

In an aspect, the present invention discloses that the sunscreen composition can be applied once per day, applied two, three, four or more times per day, applied every other day or applied about 10, 8, 7, 6, 5, 4, 3, 2 or 1 time per week. In a further aspect, the present invention discloses that a sunscreen can be applied to wet skin and/or hair or applied to dry skin and/or hair. In a further aspect, the present invention discloses that a sunscreen composition contains one, two or more surface-treated metal oxide pigments that block UV radiation, further, wherein the surface-treated metal oxide can block UV radiation in the wavelength range of from about 290 nm to about 400 nm.

In an aspect, the present invention discloses that a cellulose derived capsules containing sunscreen active agents are in the 400-450 nm range, the 400-500 nm range, the 400-550 nm range, the 400-600 nm range, the 400-650 nm range. In a further aspect, the present invention discloses that the cellulose derived capsules contain an active coating on the exterior of the cellulose derived capsule membrane which has absorption properties. In a further aspect, the present invention discloses that the cellulose derived capsules are of different sizes. In a another aspect, the present invention discloses that the cellulose derived capsule is comprised of 0.1%-5% wt/wt of cellulosic material, 5%-20% wt/wt of cellulosic material, 20%-50% wt/wt of cellulosic material or 50%-70% wt/wt of cellulosic material. In a further aspect, the present invention discloses that the cellulose derived capsule is comprised of two or more layers, further, wherein each layer can contain a different sunscreen active agent, wherein each layer ca contain the same sunscreen active agent, wherein each layer can contain a different sunscreen active agent, wherein at least one layer can contain a different sunscreen active agent than at least one other layer, wherein at least one layer can contain a sunscreen active agent and at least one layer contains an antioxidant, wherein at least one layer can contain a sunscreen active agent and at least one layer contains a vitamin, wherein at least one layer can contain a sunscreen active agent and at least one layer contains an anti-inflammatory, wherein at least one layer can contain a sunscreen active agent and at least one layer contains an astringent.

In an aspect, the present invention discloses that a sunscreen composition can be comprised of a cationic surfactant, a cellulose derived capsule and a polymer, can be comprised of an anionic surfactant, cellulose derived encapsulate, and a polymer, can be comprised of a nonionic surfactant, cellulose derived encapsulate, and a polymer, can be comprised of an amphoteric surfactant, cellulose derived encapsulate, and a polymer, wherein the composition can be comprised of a surfactant containing a quat group, wherein said quat group is capable of absorbing UV radiation, can be comprised of a surfactant metal complex to enhance reflective properties, can be comprised of more than one surfactant, a cellulose derived capsule and a polymer, can be comprised of a cellulose derived capsule comprising ethyl cellulose and a surfactant base containing one or more polymers, can be comprised of a cellulose derived capsule comprising carboxymethyl cellulose and a surfactant base containing one or more polymers.

In an aspect, the present invention discloses that a sunscreen active agent is an organic or non-polar highly refractive sunscreen active agent, or a sunscreen active agent is an organic sunscreen active agent and wherein, the composition contains inorganic metals. In an aspect, the present invention discloses that a sunscreen composition comprises a surfactant, apolymer and a cellulose derived capsule, further wherein, the composition is comprised of one or more different cellulose derived capsules, each comprised of a different cellulose derivative.

In an aspect, the present invention discloses that the inner refractive index of a sunscreen composition is 1.5-1.7, is 1.5-1.9, is 1.5-2.2, is 1.5-2.4, is 1.5-2.6, In a further aspect, the present invention discloses that the inner refractive index of a non-sunscreen active agent in the composition is 1.5-2.7. In an additional aspect, the present invention discloses that the inner refractive index of a non organic dispersed with organic sunscreen active agent in the composition is 1.5-2.7. In a further aspect, the present invention discloses that the composition contains cellulose derived capsules of different sizes and the inner refractive index of the composition is greater than 1.5.

In an aspect, the present invention discloses that the composition contains cellulose derived capsules, further wherein, the mixture of cellulose derived capsules contains capsules containing different cellulose derivatives and the inner refractive index of the composition is greater than 1.5. In a further aspect, the present invention discloses that the composition has an overall refractive index of 1.4-2.

DETAILED DESCRIPTION

The present invention encompasses compositions containing one or more sunscreen active agents capable of protecting an individual from the deleterious effects of exposure to the sun's harmful UV radiation (hereinafter, referred to as "sunscreen active agent or sunscreen active agents") in a cellulose derived capsule that may be added, without limitation, to a bodywash, a shampoo, a conditioner, a gel, a hand sanitizer, a cream, a spray, a mouse or a lotion (hereinafter referred to as a "combination product"). In an embodiment, the invention relates to a cellulose derived capsule that encompasses a sunscreen composition, wherein the sunscreen composition comprises one or more sunscreen active agents, further wherein the sunscreen composition is s solid or a liquid. In a further embodiment, the sunscreen composition also contains one or more additional agents that can include, without limitation, surfactants, polymers, antimicrobials, vitamins, antioxidants, pigments, fragrances, hindered amine light stabilizers, skin whitener and other additional agents that after administration by an individual, deposit an active agent on a substrate, for example, without limitation, an individual's skin or hair, forming a film that reflects or absorbs to some degree the harmful radiation from the sun or attenuates the harmful effect of ultraviolet radiation and with certain active agents, provides an additional benefit. The present invention provides a body wash, shampoo, conditioner, gel, hand sanitizer, cream, spray, mousse or a lotion that is formulated so that it may be applied during normal hygienic activities, such as washing, moisturizing or other normal hygiene activities, such that the combination product results in the application of an effective level of a sunscreen active agent encapsulated in a cellulose derived capsule to the body such that the sunscreen active agent continues to provide effective solar protection even after rinsing or washing of an individual's body.

In an embodiment, a sunscreen active agent comprises a sunscreen additive that absorbs or reflects some or all of the sun's ultraviolet ("UV") radiation on the skin of an individual exposed to sunlight and thus, helps to protect an individual against overexposure to the UV radiation. Sunscreen active agents commonly contain one or more of the following ingredients: an organic chemical compound that absorbs UV radiation, inorganic particulates that reflect, scatter and/or absorb UV radiation (such as titanium dioxide, zinc oxide, or a combination of both) and organic particulates that mostly absorb light like organic chemical compounds. In an embodiment, a sunscreen composition can include a surfactant metal complex to enhance the reflective property of a sunscreen composition containing a sunscreen active agent. In a further embodiment, a cellulose derived capsule membrane can increase the absorption properties of a sunscreen formulation.

In an embodiment, a sunscreen active agent is combined with a bodywash, shampoo, conditioner, gel, hand sanitizer, cream, lotion, spray or mousse and can include, without limitation, a additional agent to form a combination product. In an embodiment, a bodywash includes, without limitation, a lathering bodywash or a non-lathering bodywash. In an embodiment, a bodywash includes, without limitation, an emulsion of water and detergent base with added fragrance and is a skin cleaning agent commonly used in a shower or bath. In an embodiment, a body wash includes, without limitation, popular brands such as Fa, Palmolive, Axe, Lynx, Radox, Nivea, Johnson, Senses, Adidas, Umbro, Old Spice, Imperial Leather and right guard. In an embodiment, a bodywash contains a milder surfactant than a shampoo. In a further embodiment, a bodywash includes, without limitation an all-in-one multifunctional, moisturizing cleanser that both provides SPF and imparts color to the skin after application, wherein the bodywash includes, without limitation, iron oxide pigments as well as red petrolatum, at least one, preferably two, anionic lathering surfactants, a non-ionic lathering surfactant, surface-treated zinc oxide pigments, an alkyl silicone and a volatile cyclic silicone.

In an embodiment, a spray includes, without limitation, an aerosol spray. In a further embodiment, a spray includes, without limitation, hair spray, body spray, for example, without limitation, those sold by AXE, spray on insect protection and spray on deodorant. In one aspect of the present invention, the SPF liquid cleansing composition is aerosolized. In a further embodiment, the aerosol spray includes, without limitation, a propellant. In an additional embodiment, a propellant is, without limitation is a mixture of isobutane, butane and propane, including, without limitation A46, AP30 (11% Propane, 29% Isobutane, 60% n-butane); AP40 (22% Propane, 24% Isobutane, 54% n-butane); and AP70 (31% Propane, 23% Isobutane, 46% n-butane).

In an embodiment, a shampoo includes, without limitation, sodium lauryl sulfate and/or sodium laureth sulfate with a co-surfactant, including, without limitation, cocamidopropyl betaine in water to form a thick, viscous liquid. In a further embodiment, a shampoo includes salt, including, without limitation, sodium chloride, a preservative and a fragrance. In an embodiment, a shampoo is formulated to maximize the following qualities, without limitation, pleasing foam, easy rinsing, minimal skin or eye irritation, feels thick and/or creamy, pleasant fragrance, low toxicity, good biodegradability, slightly acidic and no or minimal damage to hair.

In a further embodiment, a lotion includes, without limitation, a low to low medium viscosity topical preparation intended for application to unbroken skin. In an embodiment, a lotion is an oil-in-water emulsion that includes, without limitation, cetearyl alcohol and an emulgent to prevent separation of these two phases. In an embodiment, a lotion contains, without limitation, fragrances, glycerol, petroleum jelly, dyes, preservatives, proteins and stabilizing agents. In an embodiment, lotions include, without limitation a skin medication such as an antibiotic, antiseptic, antifungal, corticosteroid, anti-acne agents or soothing, smoothing, moisturizing or protective agents, including, without limitation, calamine. In an embodiment, a gel includes, without limitation, a solid, jelly-like material that can have properties ranging from soft and weak to hard and tough and include, without limitation, substantially dilute cross-linked system, which exhibit no flow when in a steady-state. In an embodiment a gel includes, without limitation, a hydrogel an organogel or a xerogel.

In an embodiment, a conditioner includes, without limitation, hair conditioner, which can include, without limitation, the following ingredients: moisturizers, reconstructors, acidifiers, detanglers, thermal protectors, glossers, oils, surfactants, lubricants, sequestrants, antistatic agents, preservatives and sunscreen active agents. In an embodiment, a conditioner includes, without limitation, a pack conditioner, a leave-in conditioner, an ordinary conditioner that includes both pack and leave-in ones and hold conditioners.

In an embodiment, a hand sanitizer includes, without limitation, isopropanol, ethanol, n-propanol or povidone-iodine. In a further embodiment, hand sanitizers can contain the following inactive ingredients, without limitation, a thickening agent, including without limitation, polyacrylic acid for alcohol gels, humectants, including without limitation, glycerin for liquid rubs, propylene glycol and essential oils derived from plants. In an embodiment, a hand sanitizer is a non-alcohol hand sanitizer, which includes without limitation, a nitrogenous cationic surface-acting agent, that include, without limitation, benzalkonium chloride, triclosan or povidone-iodine.

In an embodiment, a soap is a salt of a fatty acid. Soaps for cleansing are generally obtained by treating vegetable or animal oils and fats with a strongly alkaline solution. Soaps can be in a solid form, such as a bar or in a decorative shape. Soap can also be a liquid. Other components can be added to soap, without limitation, including oils, fragrances and conditioners. In a further embodiment, a soap contains a surfactant. In another embodiment, a soap does not contain a surfactant.

In an additional embodiment, a soap is a melt and pour soap. The process for a melt and pour soap differs from the cold process, hot process or rebatching process of making soap in that no soap is made (i.e. no actual saponification occurs) in the process; a melt and pour soap base acquired in commerce is melted in a direct heat melter or water jacket melting pot (large double boiler) and additional items such as fragrance, essential oils, moisturizing agents, colorants, or exfoliating agents are added. While still hot, the concoction can be poured into individual molds, tray molds, or blocks which upon cooling can be sliced. In an embodiment, a melt and pour soap is a clear glycerin soap or a white soap made from white coconut oil.

In an embodiment, a soap is Castile soap. Castile soap is a name used in English-speaking countries for olive oil based soap made in a style similar to that originating in the Castile region of Spain. In an embodiment, Castile soap includes, without limitation, sodium hydroxide, potassium hydroxide and/or ash.

In an embodiment, a shampoo, bodywash, conditioner, gel, soap, cream or lotion combination product is applied by hand, washcloth, or any cleansing article such as a brush, loofah, pouf, sponge, or other to an individual.

The sun protection factor of a sunscreen is a laboratory measure of the effectiveness of sunscreen. What this means is that the higher the SPF, the more protection a sunscreen offers against UV-B radiation (the ultraviolet radiation that causes sunburn). The SPF is the amount of UV radiation required to cause sunburn on the skin with the sunscreen on, as a multiple of the amount required without the sunscreen. SPF is determined by measuring the Minimal Erythemal Dose ("MED") and is defined as the threshold dose that produces skin erythema. The MED indicates the amount of energy irradiating the skin and the responsiveness of the skin to the radiation. In order to determine the MED, the reaction of the skin is recorded 24 hours after exposure to UV radiation. The minimal dose that induces any visible reddening at that point is defined as one MED. Redness that occurs immediately after exposure, however, and disappears during the following three to five hours is mainly caused by heat and is not comparable with real UV erythema.

In an embodiment, "average SPF" is the SPF, determined as described herein, for about 5 to about 50 subjects, or about 5 to about 20 subjects, or about 5 to about 10 subjects, where the subjects preferably have Type II skin. The SPF of a particular sunscreen active agent is obtained by dividing the MED of skin that has been protected by an active agent by the MED of unprotected skin. The higher the SPF, the more effective the active agent is in preventing an individual from skin erythema, which is on an individual is recognized as constituting a sunburn. SPF is generally measured in numerical increments that identify how long an individual can be exposed to UV radiation from the sun before that same individual will experience 1 MED. For example, utilizing a sunscreen with an SPF of 6 will allow an individual to be exposed to the sun six times longer than an SPF of 1 before that individual receives 1 MED. As the SPF value of a sunscreen increases, the less chance exists for development UV erythema of the skin. In an embodiment, a sunscreen product containing an sunscreen active agent has an SPF value ranging from about 2 to 70. Methods for measuring SPF are described in, e.g., FDA monograph C.F.R. 21. A method for applying the sunscreen prior to measurement is as follows: Wet 50 cm$^2$ square area of testing site with 10 ml of water delivered with a syringe. Apply test sample as per FDA monograph to area. Work lather on the subject for 3 minutes to allow the product to absorb into the skin. Rinse area after 2 additional minutes with 20 ml of water. Pat dry and allow 15 minutes before exposure to radiation as per FDA monograph.

Log P is a term known to those of skill in the chemical arts. It is a measure of differential solubility of a compound in two solvents. More particularly, it is a partition coefficient expressed as the log ratio of the concentrations of the solute in the solvent. A partition coefficient well known to persons having ordinary skill in the art is based on the solvents Octanol and Water. In an embodiment, a sunscreen active agent has a log P of greater than about 4.0 that blocks or absorbs ultraviolet radiation in the wavelength range of from about 290 nm to about 400 nm and is selected from the group consisting of octylmethoxycinnamate, octocrylene and octyl salicylate. The at least one organic sunscreen agent having a log P of greater than about 4 that blocks or absorbs ultraviolet radiation in the wavelength range of from about 290 nm to about 400 nm includes sunscreens currently approved by the FDA and listed in the Sunscreen Drug Products for Over-The-Counter Human Use Final Monograph published in the Fed era! Register on May 21, 1999 at Volume 64, Number 98, pages 27666-27693 as well as organic sunscreen active agents approved by regulatory agencies in countries other than the United States.

Any sunscreen active agent known in the art or apparent to the skilled artisan may be used in the invention. The term sunscreen active agent as used herein defines ultraviolet ray-blocking compounds exhibiting absorption or blockage within the wavelength region between about 290 and 420 nm. Sunscreen active agents may be classified, without limitation, into five groups based upon their chemical structure: paraamino benzoates; salicylates; cinnamates; benzophenones; and miscellaneous chemicals including menthyl anthralinate and digalloyl trioleate. Inorganic sunscreen active agents may also be used including titanium dioxide, zinc oxide, iron oxide and polymer particles such as those of polyethylene and polyamides.

Specific suitable sunscreen active agents include, for example: p-aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenlyll); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy- or methoxy substituted benzophenones; Uric and vilouric acids; Tannnic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy4,4'-dimethoxybenzophenone, Octabenzone; 4-Isopropyhldibenzoylmethane; Butylmethoxydibenzoylmethane; Etocrylene; and 4-isopropyl-dibenzoylmethane; titanium dioxide, iron oxide, zinc oxide, and mixtures thereof. Other cosmetically-acceptable sunscreens and concentrations (percent by weight of the total cosmetic sunscreen composition) include diethanolamine methoxycinnamate (10% or less), ethyl-[bis(hydroxypropyl)] aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less). In an embodiment, sunscreen active agents are FDA-approved or approved for use in the European Union. For example, FDA-approved sunscreen active agents may be used, singly or, preferably, in combination. See, e.g., U.S. Pat. Nos. 5,169,624; 5,543,136; 5,849,273; 5,904,917; 6,224,852; 6,217,852; and Segarin et al., chapter ViI, pages 189 of Cosmetics Science and Technology, and Final Over-the-Counter Drug Products Monograph on Sunscreens (Federal Register, 1999:64:27666 27963), all of which are incorporated herein by reference.

In an embodiment, zinc oxide is used as a sunscreen active agent and the fine particle size of the zinc oxide is in the range from 2 to 50 microns. In a further embodiment, the zinc oxide is, without limitation, at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more microns. In a further embodiment, zinc oxide can, without limitation, be surface coated to facilitate dispersion.

In an embodiment, a product marketed in the United States, preferred cosmetically-acceptable sunscreen active agents and concentrations (reported as a percentage by weight of the total cosmetic sunscreen composition, and referring to the final percentage of the sunscreen active agent after addition to the bodywash) include: aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), decamsule, dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), zinc oxide (25% or less, an inorganic physical blocker of UVA and UVB) and Tineubin (a UVA absorber manufactured by BASF).

In an embodiment, in the European Union, preferred cosmetically-acceptable photoactive sunscreen active agenst and concentrations (reported as a percentage by weight of the total cosmetic sunscreen composition, and referring to the final percentage of the sunscreen active agent after addition to the bodywash) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), Mexoryl XL, Neo heliopan AP, Benzophenone-9, Uvinul T 150, Uvinul A Plus, Uvasorb HEB, Parsol SLX, benzylidene camphor sulfonic acid (6% or less, expressed as acid), octocrylene (10% or less, expressed as acid), polyacrylamidomethyl benzylidene camphor (6% or less), octyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bisethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine. (10% or less, also called TINOSORB S).

In further embodiments, the sunscreen active agent includes, without limitation, a silicone long-chain molecule with chromophores, e.g., PARASOL SLX (DSM Nutritional Products), which contains benzyl malonate chromophores attached to specific points on a polysiloxane chain. In an additional embodiment, a sunscreen active agent comprises a silicone long-chain molecule with chromophores. In an embodiment, sunscreen compositions include, without limitation, octyl methoxycinnamate, octocrylene, avobenzone, titanium dioxide, and a silicone long-chain molecule with chromophores. In an embodiment, the silicon long-chain molecule may be used in sunscreen active agents at about 0.5 to about 5%, or in a combination product comprising one or more sunscreen active agents and a bodywash, shampoos, lotion, conditioner, gel, soap, hand sanitizer, cream, or spray at a concentration of about 0.2 to about 2% (w/v).

In an embodiment, inorganic physical blockers of UVA and UVB include, without limitation, iron oxide and polymer particles such as those of polyethylene and polyamides. In further embodiments, a sunscreen active agent is, without limitation, cinnamate (e.g., Octylmethoxycinnamate (ethyl hexyl methoxycinnamate), (available under the tradename PARSOL MCX), oxybenzone (e.g., benzophenone-3 (2-Hydroxy4-Methoxybenzophenone), avobenzone (4-tert-Butyl-4'-methoxydibenzoylmethane or PARSOL 1789), octyl salicylate (2-Ethylhexyl Salicylate), octocrylene (2-Ethylhexyl 2-Cyano-3,3-Diphenylacrylate), methyl anthranilate, and/or titanium dioxide, or combinations thereof.

In an embodiment, a p-methoxycinnamic acid ester first sunscreen active agent includes, without limitation, amyl p-methoxycinnamate, 2-ethylhexyl p-methoxycinnamate, 2-ethoxyethyl p-methoxycinnamate, diethanolamine p-methoxycinnamate, n-octyl p-methoxycinnamate and propyl p-methoxycinnamate.

In an embodiment, a second sunscreen active agent recognized as safe and effective by the US Food and Drug Administration includes, without limitation, p-aminobenzoic acid, Cinoxate, Avobenzone, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene ethyl 2-cyano-3,3-diphenyl acrylate, octyl salicylate, oxybenzone, Padimate 0, phenylbenzimidazole sulfonic acid, red petrolatum, sulisobenzone, titanium dioxide, zinc oxide, including regular grades and grades of such fine particle size as enable the composition to be translucent or transparent, and triethanolamine salicylate. Additional sunscreen compounds recognized by European authorities include N,N,N-trimethyl-4-(2-oxoborn-3-ylidene methyl)anilinium methyl sulfate, 3-imidazol-4-ylacrylic acid and its ethyl ester, 2-phenylbenzimidazole-5-sulfonic acid and its salts, ethoxylated 4-aminobenzoic acid, amyl 4-dimethylaminobenzoate, 3,3,5-trimethylcyclohexyl-2-acetamidobenzoate, potassium cinnamate, 4-methoxycinnamic acid salts, propyl 4-methoxycinnamate, salicylic acid salts, amyl 4-methoxycinnamate, mexenone, sulisobenzone, 2-ethylhexyl 2-(4-phenylbenzoyl)-benzoate, 5-methyl-2-phenylbenzoxazole, sodium 3,4-dimethoxyphenylglyoxylate, 1,3-bis(4-methoxyphenyl) propane-1,3-dione, 5-(3,3-dimethyl-2-norbornylidene)-3-penten-2-one, alpha-(2-oxoborn-3-ylidene)-p-xylene-2-sulfonic acid, alpha-(2-oxoborn-3-ylidene)toluene-4-sulfonic acid and its salts, 3-(4-methylbenzylidene)bornan-2-one, 3-benzylidenebornan-2-one, alpha-cyano-4-methoxycinnamic acid and its hexyl ester, 1-p-cumenyl-3-phenylpropane-1,-3-dione, 4-isopropylbenzyl salicylate, cyclohexyl 4-methoxycinnamate, and 1-(4-t-butylphenyl)-3-(4-methoxyphenyl)propane-1,3-dione.

In an embodiment, a sunscreen active agent includes, without limitation, octyl methoxycinnamate at about 4.5 to about 9%, Octocrylene at about 0.5 to about 15%, Avobenzone (e.g., PARSOL 1789) at about 2 to about 4%, and titanium dioxide at about 3 to about 9%.

In an embodiment, a sunscreen composition includes, without limitation, about 0.1 to 7.5 weight percent of octylmethoxy cinnamate, about 0.1 to 6 parts weight percent of octyl salicylate, about 0.1 to 5 parts weight percent of oxybenzone, about 1 to 10 weight percent of cationic surfactant, and about 0.01 to 1 weight percent of a quaternized compound. These sunscreen compositions may further include, without limitation, a film former and/or 0.01 to 1 weight percent of a preservative.

In an embodiment, a composition containing a sunscreen active agent provides protection from the sun's UV radiation after application on average, by greater than an SPF of 1 and up to about SPF 70. In a further embodiment, the average SPF provided by a composition containing a sunscreen active agent is about 1 to about 50, or about 2 to about 50, or about 2 to about 40, or about 2 to about 30, or about 2 to about 20, or about 2 to about 10, or about 2 to about 5, or about 5 to about 25, or about 5 to about 20, or about 5 to about 15, or about 5 to about 10. In an additional embodiment, the average SPF provided by a composition containing a sunscreen active agent is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more. In an embodiment, the average SPF is above about 2, above about 5, above about 10, above about 15. In an embodiment, the average SPF provided by a composition containing a sunscreen active agent remains at least 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, for an average of at least about 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 hours or more or for an average, of at least about 1 day, 2 days, 3 days, 4 days, 5 days, 6 days, 7 days, 8 days, 9 days, 10 days, 11 days, 12 days, 13 days, 14 days, after rinsing. In an embodiment the average SPF provided by a composition containing a sunscreen active agent increases with each additional washing after a first wash, so that after a second, third, fourth, fifth, sixth, seventh, eighth, ninth, tenth, eleventh or more washes, the SPF provided can be at least 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more.

In an embodiment, a composition containing a sunscreen active agent provides protection from the sun's UV radiation after application on average, and after rinsing, by greater than an SPF of 1 and up to about SPF 70. In a further embodiment, the average SPF provided by a composition containing a sunscreen active agent after rinsing is about 1 to about 50, or about 2 to about 50, or about 2 to about 40, or about 2 to about 30, or about 2 to about 20, or about 2 to about 10, or about 2 to about 5, or about 5 to about 25, or about 5 to about 20, or about 5 to about 15, or about 5 to about 10. In an additional embodiment, the average SPF provided by a composition containing a sunscreen active agent, after rinsing, is above about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more. In an embodiment, the average SPF after rinsing is above about 2, above about 5, above about 10, above about 15, In an embodiment, the average SPF provided by a composition containing a sunscreen active agent, after rinsing, remains above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, for an average of at least about 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 hours or more or for an average, of at least about 1 day, 2 days, 3 days, 4 days, 5 days, 6 days, 7 days, 8 days, 9 days, 10 days, 11 days, 12 days, 13 days, 14 days, after rinsing. In an embodiment the average SPF provided by a composition containing a sunscreen active agent increases with each additional washing after a first wash, and a subsequent rinse, so that after a second, third, fourth, fifth, sixth, seventh, eighth, ninth, tenth, eleventh or more washes, the SPF provided can be above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more.

In an embodiment, after application of a composition containing a sunscreen active agent to the skin followed by rinsing, the sunscreen active agent penetrates to an average of at least about 5 microns beneath the skin surface. In an embodiment, the sunscreen active agent penetrates to an average of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145 or 150 microns beneath the skin surface. In a further embodiment, after application of a body wash, shampoo, conditioner, gel, soap, hand sanitizer, cream, spray, mousse and/or and lotion containing sunscreen active agent to the skin and/or hair followed by rinsing, the sunscreen active agent penetrates to an average of no more than about 5, 10, 15, 20, 25, 30, 35, 40, 45, 50, 55, 60, 65, 70, 75, 80, 85, 90, 95, 100, 105, 110, 115, 120, 125, 130, 135, 140, 145 or 150 microns beneath the skin surface. In an additional embodiment, after application of the body wash, shampoo, conditioner, gel, soap, hand sanitizer, cream, spray, mousse and/or and lotion containing an active agent to the skin followed by rinsing, the active agent penetrates to an average of about 5 to about 150, 5 to about 140, to about 5 to about 130, 5 to about 120, 5 to about 110, 5 to about 100, 5 to about 90, 5 to about 80, 5 to about 70, 5 to about 60, 5 to about 50, 5 to about 40, 5 to about 30, 5 to about 20, 5 to about 10, 10 to about 20, 10 to about 30, 10 to about 40, 10 to about 50, 10 to about 60, 10 to about 70, 10 to about 80, 10 to about 90, 10 to about 100, 20 to about 30, 20 to about 40, 20 to about 50, 20 to about 60, 20 to about 70, 20 to about 80, 20 to about 90, 20 to about 100, 30 to about 40, 30 to about 50, 30 to about 60, 30 to about 70, 30 to about 80, 30 to about 90, 30 to about 100, 40 to about 50, 40 to about 60, 40 to about 70, 40 to about 80, 40 to about 90, 40 to about 100, 50 to about 60, 50 to about 70, 50 to about 80, 50 to about 90, 50 to about 100, 60 to about 70, 60 to about 80, 60 to about 90, 60 to about 100, 70 to about 80, 70 to about 90, 70 to about 100, 80 to about 90, 80 to about 100 or 90 to about 100, or about 5, 10, 15, 20, 25, 30, 25, 40, 45, or 50 microns beneath the skin surface. Depth of penetration may be tested by tape stripping methods that are well-known in the art.

In an embodiment, a sunscreen composition containing a sunscreen active agent contains at least one sunscreen active agent. In a further embodiment, a sunscreen composition containing a sunscreen active agent contains one, two, three, four, or more different sunscreen active agent. In an embodiment, a composition containing a sunscreen active agent contains three different sunscreen active agents. In a further embodiment, a composition containing a sunscreen active agent contains four, five or six different sunscreen active agenst. The sunscreen active agent may be an organic molecule or inorganic. The sunscreen active agent may be a UVA absorber, a UVB absorber, a physical blocker, a physical reflector, or any combination thereof. In an embodiment, one or more of the sunscreen active agents is encapsulated in a cellulose capsule. In an embodiment, a composition containing a sunscreen active agent may include, without limitation, one or more other additional agents. In a further embodiment, the additional agents are included in a sunscreen composition that contains one or more sunscreen active agents.

In a further embodiment, the additional agents can be, without limitation, one or more components capable of providing a positive charge to the system to assist with attachment to a negatively charged molecule or surface, such as, without limitation, charged components of skin and/or hair. In an embodiment, the cationic polymer is, without limitation, a quaternium, e.g., polyquaternium. The additional agents can be, without limitation, a film former, including, without limitation, dimethicone and/or petrolatum, and/or a preservative, such as BHT. In a further embodiment, other additional agents, that can be added to a sunscreen formulation, but are not necessarily required, include, without limitation, preservatives, antioxidants, chelating agents, liquid hydrocarbon (e.g., one similar to pentane), foaming agents (e.g., a cationic foaming agent), skin nourishing components, antibacterials, medicinals, and the like.

In an embodiment, the sunscreen composition containing a sunscreen active agent is applied topically to the skin of an individual. In a further embodiment, the sunscreen composition containing a sunscreen active agent is applied to the hair or sprayed onto the skin or hair of an individual. In an additional embodiment, the sunscreen composition containing a sunscreen active agent that is applied topically or sprayed onto the hair or skin of an individual contains, without limitation, at least one additional agent.

In an embodiment, the sunscreen composition containing a sunscreen active agent is applied to an individual with an applicator, including, without limitation, with a sponge, a loofah, a toy, a cotton pad, a wash cloth, a specialized wash cloth, a towel, clothing, a spray bottle, an applicator bottle or any device or article, including a clothing article or applicator. In a further embodiment, a toy, includes, without limitation, a rubber squeeze toy, including, without limitation, a rubber duck, or a plastic squeeze toy. In an embodiment, the applicator is preloaded or can be loaded with the sunscreen composition containing a sunscreen active agent. In an embodiment, the application, includes, without limitation, an applicator bottle with a roller ball, a push button, a nozzle, a turn nob or other means to to apply the sunscreen composition to an individual. In a further embodiment, the applicator provides the sunscreen composition to an individual in metered, defined amounts. In an embodiment, the metering is by pushing down on a nozzle that is part of the applicator. In a further embodiment, the applicator is a squeezable bottle wherein the sunscreen composition can be removed from the bottle as an individual squeezes the bottle. In an embodiment, the sunscreen composition containing a sunscreen active agent is applied using a spray on applicator, including, without limitation, a spray bottle.

In an embodiment, the sunscreen composition containing a sunscreen active agent is a powder or other dry form. In a further embodiment, the sunscreen composition containing a sunscreen active agent is applied to an individual by applying the powder or other dry form to the individual. In a further embodiment, following application of the powder or other dry form, the sunscreen composition containing a sunscreen active agent is rubbed, massaged, caressed onto the individual. In an embodiment, the sunscreen composition containing a sunscreen active agent that is in the form of a powder or other dry form is stored in an applicator. In an embodiment, the applicator is the same as the applicator used for powder or other dry form products, including, without limitation, a baby powder bottle or other applicator that is conformed to the application of a powder or other dry form of a sunscreen composition.

In an embodiment, the sunscreen active agents of the invention can be, without limitation, combined with a conventional bodywash, shampoo, lotion, spray, conditioner, gel, soap, hand sanitizer, cream, or mousse. The bodywash, shampoo, lotion, spray, conditioner, gel, soap, hand sanitizer, cream, or mousse can be, without limitation, any bodywash, shampoo, lotion, spray, conditioner, gel, soap, hand sanitizer, cream or mousse known in the art or apparent to one of skill in the art, as described above. In a further embodiment, the invention provides a sunscreen composition containing at least one or more sunscreen active agents in combination with one or more surfactants. The surfactant(s) may be cationic, anionic, nonionic, zwitterionic, amphoteric, or any combination thereof. In an embodiment, the bodywash, shampoo, lotion, spray, conditioner, gel, soap, hand sanitizer, cream or mousse contains at least one sunscreen active agent that is organic or inorganic, or a combination of both. In an embodiment, sunscreen compositions include UV absorbers, blockers (e.g., many inorganic sunscreens are UV blockers) or reflectors. UV absorbers may be a UVB or UVA absorber (e.g., UVA I or UVA II absorber). In a further embodiment, a sunscreen active agent includes, without limitation, more than one organic sunscreen active agent (e.g., at least one UVB absorber and at least one UVA absorber) and at least one inorganic sunscreen active agent. In an embodiment, a sunscreen active agent is a physical blocker sunscreen, e.g., titanium dioxide. In an additional embodiment, a sunscreen active agent is, without limitation, a cationic polymer and/or a film former as well as any other components described herein for sunscreen active agents. Additional ingredients may include film formers, cationic polymers, antioxidants, preservatives, and the like.

In an embodiment, a sunscreen composition is used, without limitation, to treat an individual suffering from, Seborrheic dermatitis, eczema, xerosis, infestation, dyschromia, keratosis pilaris, acne, anti-aging, sensitive skin, ephilidies, solar lentigines, photo sensitive disease, skin cancer and hx of skin cancer, melisma, auto immune, alopecia, fungal, bacterial, and viral infections, protect colored or treated hair, bromhidrosis, malodor, dandruff, wound healing, insect repellant, pet shampoo/skin care, lindane or similar conditions.

In an embodiment, a sunscreen composition can contain as a sunscreen active agent only titanium dioxide. Titanium dioxide, either alone or in combination with other sunscreens, can have an anatase, rutile, or amorphous structure. Titanium dioxide particles can be uncoated or can be coated with a variety of materials including, without limitation, aluminum compounds such as aluminum oxide, aluminum stearate, aluminum laurate and the like; phospholipids such as lecithin; silicone compounds; and mixtures thereof. Various grades and forms of titanium dioxide are described in CTFA Cosmetic Ingredient Dictionary, Third Edition (1982), pp. 318 319; U.S. Pat. No. 4,820,508 to Wortzman, issued Apr. 11, 1989; and World Patent No. WO 90/11067 to Elsom et al, published Oct. 4, 1990; these three references are incorporated by reference herein in their entirety. Suitable grades of titanium dioxide for use in a sunscreen composition can be purchased from commercial suppliers, including, without limitation, the MT micronized series from Tri-K Industries (Emerson, N.J.). Micronized titanium dioxides generally have a mean primary particle size ranging from about 10 nm to about 50 nm. For example, the titanium dioxide has a mean primary particle size of about 15 nm and this sunscreen active agent is available under the trade designation MT-15OW (uncoated) and MT-100T (coated with stearic acid and aluminum compounds). Uncoated titanium dioxides having mean primary particle sizes of around 35 nm and around 50 nm are available under the trade designations MT-500B and MT-600B, respectively. Other coated titanium dioxides having a mean primary particle size around 15 nm include MT-100F (modified with stearic acid and iron hydroxide) and MT-100S (treated with lauric acid and aluminum hydroxide). Mixtures of two or more types and particle size variations of titanium dioxide can be used in the present invention. In an embodiment the titanium dioxide is a silica-coated titanium dioxide, including, without limitation T-AVO (Eusolex).

In an embodiment, a sunscreen composition contains a zinc based sunscreen active agent (e.g., Z-COTE™ HP 1 [registered trademark, SkinCeuticals]). Zinc sunscreen active agent can be, without limitation, a micro-fine zinc oxide coated with a form of dimethicone that transforms the frequently granular and pasty particles of zinc oxide to a smooth formulation which is transparent and does not give the appearance of skin coated with white paint.

In a further embodiment, inorganic sunscreen active agents are, without limitation, Tioveil and Spectraveil (both of the Tioxide Group). Tioveil include, without limitation, products which are 40% dispersions of surface-treated titanium dioxide in a range of cosmetic vehicles. Spectraveil include, without limitation, products which are 60% dispersions of zinc oxide in a range of cosmetic vehicles. In an embodiment, Tioveil and Spectraveil are film-formers.

In an embodiment, a sunscreen composition comprising one or more sunscreen active agents is encapsulated. In a further, embodiment, a sunscreen composition comprises one or more sunscreen active agents and one or more additional agents that are encapsulated. Encapsulation increases the stability of the sunscreen composition as well as increases the effectiveness of the sunscreen composition to protect an individual from deleterious effects suffered from exposure to the sun's harmful rays. Encapsulation also can minimize their absorption of the sunscreen active agent into the dermis and its excretion in the urine.

In an embodiment, a sunscreen active agent comprises about 0.1% to about 50%, or about 1% to about 30%, or about 1% to about 25%, or about 3% to about 25%, or about 5% to about 25%, or about 10% to about 25% or about 15% to about 25%, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more of the sunscreen composition (all percentages herein are weight per volume percent unless otherwise specified). In an embodiment, a combination of one or more sunscreen active agents and a bodywash, shampoo, lotion, mousse, conditioner, gel, soap, hand sanitizer, cream, or spray, the one or more sunscreen active agents comprise at least about 0.05, 1.5, 2.5, 7.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or, or more than 50% of the sunscreen composition.

In an embodiment, a sunscreen composition absorbs at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of incident radiation at wave lengths of 290 to 320 nanometers, In a further embodiment, a sunscreen composition absorbs at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of incident radiation at wave lengths less than 290 or greater than 320 nanometers.

In an embodiment, a sunscreen composition is combined with a bodywash, shampoo, lotion, conditioner, gel, soap, hand sanitizer, cream, spray or mousse in a ratio of about one part sunscreen active agent to two parts bodywash, shampoo, lotion, conditioner, gel, soap, hand sanitizer, cream, spray or mousse measured as w/w. In a further embodiment, the ratio of sunscreen composition to bodywash, shampoo, lotion, conditioner, gel, soap, hand sanitizer, cream, spray or mousse is, without limitation, about 0.2, 0.5, 0.7 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10; 12, 15, or 20 parts bodywash, shampoo, lotion, conditioner, gel, soap, hand sanitizer, cream, spray or mousse to sunscreen active agent as measured w/w.

In an embodiment, the sunscreen composition has a pH of about 6 to about 8. In a further embodiment, the sunscreen composition has a pH of about 6.7 to about 7.5. In a further embodiment, the sunscreen composition has a pH of at least 1, 2, 3, 4, 5, 6, 7, 8, 9, 10, 11, 12, 13, or 14.

In an embodiment, a sunscreen composition is combined with a bodywash, shampoo, lotion, conditioner, gel, soap, hand sanitizer, cream, spray or mousse all at once, in groups, or separately. In an embodiment, a sunscreen composition comprises at least two separate components that include, without limitation, a first component that comprises all the ingredients except an inorganic or physical blocker sunscreen, and a second component that comprises an inorganic or physical blocker sunscreen active agent. In an embodiment, a first component is added to a bodywash, shampoo, lotion, conditioner, gel, soap, hand sanitizer, cream, spray or mousse with thorough mixing, followed by a second component. In a further embodiment, all ingredients except the titanium dioxide are mixed, then added to a bodywash, shampoo, lotion, conditioner, gel, soap, hand sanitizer, cream, spray or mousse, and then the titanium dioxide is added.

In an embodiment, a sunscreen composition is encapsulated in a cellulose derived capsule. In a further embodiment, a sunscreen composition is encapsulated in a cellulose derived capsule and a second sunscreen composition is not encapsulated. In a further embodiment, a sunscreen composition contains cellulose derived capsules comprising more than one cellulose derivative. In a further embodiment, the cellulose derived capsules in a sunscreen composition are of different sizes and/or contain multiple layers. In an additional embodiment, each layer of a cellulose derived capsule can contain one or more sunscreen active agents and/or additional agents.

In an additional embodiment, one or more different sunscreen compositions are encapsulated in a cellulose derived capsule and one or more sunscreen compositions are not encapsulated. Generally, encapsulation of a molecule, including, without limitation, a sunscreen active agent or a additional agent involves trapping the sunscreen active agent or additional agent in, e.g., a vesicle. In an embodiment, depending on the vesicle of choice, the vesicle may remain intact following application to an individual or it may break open when applied. In a further embodiment, the vesicle may break open when applied over a period of time, wherein the period of time can be continuous until the last vesicle breaks open or at one or more defined period after application to an individual. In an embodiment, the the stability, durability, and/or SPF protection provided by a sunscreen active agent in a bodywash, shampoo, conditioner, gel, soap, hand sanitizer, cream, lotion, spray or mousse can be increased through the selection of a particular cellulose derived capsule that meets the desired requirements.

In an embodiment, a cellulose derived capsule is a capsule wherein at least a portion of the capsule is composed of a cellulose derivative. In a further embodiment, a cellulose derived capsule includes, without limitation, a capsule wherein the capsule is composed solely of a cellulose derivative. In a further embodiment, a cellulose derived capsule includes, without limitation, one or more anionic components as part of the capsule. In a further embodiment, a cellulose derived capsule includes, without limitation, one or more cationic components as part of the capsule. In a further embodiment, a cellulose derived capsule includes, without limitation one or more additional ingredients, including without limitation, a lipid, a dye, a therapeutic, a protein, an antimicrobial, an antibiotic or other molecule. In an embodiment, a capsule is a microcapsule, also known as a microsphere. In an additional embodiment, a cellulose derived capsule is flexible, can have high load rates and can be prepared in large quantities without a high reaction time and drying step. The preparation and purification of cellulose derived capsules are well known in the art and available for one of skill to prepare the cellulose derived capsules of the present invention. In an embodiment, a cellulose derived capsule is photostable. In a further embodiment, a cellulose derived capsule is not photostable and without limitation, disintegrate following exposure to the sun and release their internal contents, including, a sunscreen active agent and any additional agents included in the sunscreen composition.

In an embodiment, a cellulose derivative for use in a cellulose derived capsule includes without limitation, hydroxypropylcellulose, hydroxypropylmethylcellulose, ethylcellulose and carboxymethylcellulose, and any derivatives therefrom. In an embodiment, the cellulose derivative used in a cellulose derived capsule is hydroxypropylcellulose. In a further embodiment the hydroxypropylcellulose has a a medium or low degree of polymerization of the hydroxypropylcellulose.

In an embodiment, a cellulose derived capsule has a diameter of about 400 nm to about 700 nm. In an additional embodiment, a cellulose derived capsule has a diameter of about 400 nm to about 650 nm, about 400 nm to about 600 nm, about 400 nm to about 550 nm, about 400 nm to about 500 nm, about 400 nm to about 450 nm, about 200 nm to about 700 nm, about 250 nm to about 650 nm, about 300 nm to about 600 nm, about 350 nm to about 550 nm. In a further embodiment, 75% or more of the cellulose derived capsules have a diameter of about 300 nm to about 600 nm. In a further embodiment, a cellulose derived capsule has a diameter of at least 25 nm, at least 50 nm, at least 75 nm, at least 100 nm, at least 125 nm, at least 150 nm, at least 175 nm, at least 200 nm, at least 225 nm, at least 250 nm, at least 275 nm, at least 300 nm, at least 325 nm, at least 350 nm, at least 375 nm, at least 400 nm, at least 425 nm, at least 450 nm, at least 475 nm, at least 500 nm, at least 525 nm, at least 550 nm, at least 575 nm, at least 600 nm, at least 625 nm, at least 650 nm, at least 675 nm, at least 700 nm, at least 725 nm, at least 750 nm, at least 775 nm, at least 800 nm, at least 825 nm, at least 850 nm, at least 875 nm, at least 900 nm, at least 925 nm, at least 950 nm, at least 975 nm, at least 1000 nm or more.

In an embodiment, a sunscreen composition includes, without limitation, any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In an embodiment, the sunscreen composition includes, without limitation, at least two, three, four, five, six, seven, eight, nine, ten, or all of these additional ingredients identified in the previous sentence. In a further embodiment, the amount of such ingredients can range from 0.0001% to 99.9% by weight or volume of the composition, or any integer or range in between. In an embodiment, a sunscreen composition includes, without limitation, one or more of the aforementioned additional ingredients, wherein the sunscreen active agent is encapsulated in a cellulose derived capsule and the additional ingredients are not encapsulated in a cellulose derived capsule, In a further embodiment, a sunscreen composition includes, without limitation, a sunscreen agent encapsulated in a cellulose derived capsule and wherein one or more additional ingredients are encapsulated in a cellulose derived capsule with the sunscreen active agent or sunscreen active agents.

In an embodiment, a sunscreen composition or a sunscreen combination product, wherein a sunscreen active agent is encapsulated in a cellulose derived capsule increases the SPF protection of an individual on which a sunscreen composition or a sunscreen combination product is applied as compared to a sunscreen composition or a sunscreen combination product where a sunscreen active agent is not encapsulated. In a further embodiment, a sunscreen composition or a sunscreen combination product, wherein a sunscreen active agent is encapsulated in a cellulose derived capsule increases the SPF protection of an individual on which a sunscreen composition or a sunscreen combination product is applied as compared to a sunscreen composition or a sunscreen combination product where a sunscreen active agent is not encapsulated by at least 0.1 times greater, 0.2 times greater, 0.3 times greater, 0.4 times greater, 0.5 times greater, 0.6 times greater, 0.7 times greater, 0.8 times greater, 0.9 times greater, 1 times greater, 1.25 times greater, 1.5 times greater, 1.75 times greater, 2 times greater, 2.25 times greater, 2.5 times greater, 2.75 times greater, 3 times greater, 3.25 times greater, 3.5 times greater, 3.75 times greater, 4 times greater, 4.25 times greater, 4.5 times greater, 4.75 times greater, 5 times greater, 5.25 times greater, 5.5 times greater, 5.75 times greater, 6 times greater, 6.25 times greater, 6.5 times greater, 6.75 times greater, 7 times greater, 7.25 times greater, 7.5 times greater, 7.75 times greater, 8 times greater, 8.25 times greater, 8.5 times greater, 8.75 times greater, 9 times greater, 9.25 times greater, 9.5 times greater, 9.75 times greater, 10 times greater, 11 times greater, 12 times greater, 13 times greater, 14 times greater, 15 times greater, 16 times greater, 17 times greater, 18 times greater, 19 times greater, 20 times greater, 21 times greater, 22 times greater, 23 times greater, 24 times greater, 25 times greater, 30 times greater, 35 times greater, 40 times greater, 45 times greater, 50 times greater, 55 times greater, 60 times greater, 65 times greater, 70 times greater, 75 times greater, 80 times greater, 85 times greater, 90 times greater, 95 times greater, 100 times greater than a sunscreen agent is not encapsulated.

In an embodiment, a cellulose derived capsule encapsulated UVB absorber, for example, without limitation, octyl methoxycinnamate, is used as a sunscreen active agent at a concentration that results in a final concentration of the UVB absorber in a shampoo, bodywash, conditioner, gel, soap, hand sanitizer, cream, lotion, spray or mousse of about 1% to about 40%, or about 2% to about 20%, or about 2% to about 10%, or about 5% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40%. In an embodiment the final concentration is about 7.6%. In an embodiment, more than one sunscreen active agent is encapsulated in a cellulose derived encapsulate. In a further embodiment, the final concentration of each of the sunscreen active agents, independently, in the final sunscreen additive, is about 1% to about 40%, or about 2% to about 20%, or about 2% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40%. The sunscreen active agents may be encapsulated together or separately, or any combination thereof. In an embodiment, a sunscreen active agent is added to a bodywash, shampoo, conditioner, gel, soap, hand sanitizer, cream, lotion, spray or mousse that includes a sunscreen active agent encapsulated in a cellulose derived capsule, including without limitation, a microcapsule. In a further embodiment, the shampoo, conditioner, gel, soap, hand sanitizer, cream, lotion, spray, mousse or bodywash containing an encapsulated sunscreen active agent also contains, without limitation, a cationic polymer. In an additional embodiment, the shampoo, lotion, spray, mousse, bodywash or conditioner, gel, soap, hand sanitizer, cream, containing an encapsulated sunscreen active agent can also contain, without limitation, a film former, an antioxidant, a preservative, a chelating agent, a thickener, an emollient, and/or other active and inactive ingredients.

In an embodiment, an active sunscreen agent is encapsulated in a cellulosic derived capsule and wherein a sunscreen active agent includes, without limitation an inorganic molecule. In a further embodiment, an inorganic sunscreen agent encapsulated in a cellulosic derived capsule includes, without limitation, titanium, zinc, metal alkoxides and more.

In an embodiment, the cellulose derived capsules, including without limitation, microcapsules, may be prepared so as to experience about 0% breakage, or breakage in a range from about 0.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95% to about 0.50.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95%, after application (or application and rinsing in the case of a bodywash, shampoo or conditioner, gel, soap, hand sanitizer, cream, containing the cellulose derived capsules). In an embodiment, a cellulose derived capsule is formulated so as to break open in response to conditions that occur on the skin, so that after application the cellulose derived capsules act to release their contents in a time-release or controlled manner.

In an embodiment, additional agents that do not protect against the sun's radiation can be encapsulated in a cellulose derived capsule with or without a sunscreen active agent. In an embodiment, additional agents that do not provide protection from the sun's radiation are encapsulated in a cellulose derived capsule that is added to a bodywash, shampoo, conditioner, gel, soap, hand sanitizer, cream, lotion, spray or mousse. In an additional embodiment, the cellulose derived capsule containing an additional agent, also contains a sunscreen active agent. In an embodiment, a additional agent that does not provide protection from the sun's radiation, includes, without limitation, sunless tanning actives, skin lightening actives, anti-acne actives, anti-skin wrinkling and anti-skin aging actives, vitamins, anti-inflammatory actives, anesthetic actives, analgesic actives, anti-pruritic actives, anti-microbial actives (e.g. antifungals, antibacterials, and antiparasitics), anti-virals, anti-allergenics, medicinal actives (e.g., skin rash, skin disease and dermatitis medications), anti-cellulite additives, insect repellant actives, antioxidants, hair growth promoters, hair growth inhibitors, hair bleaching agents, vitamins, deodorant compounds, or more. In a further embodiment, sunless tanning actives include, without limitation, dihydroxyacetone (DHA); glyceryl aldehyde; tyrosine and tyrosine derivatives such as malyltyrosine, tyrosine glucosinate, and ethyl tyrosine; phospho-DOPA, indoles and derivatives. In a further embodiment, skin lightening actives include, without limitation, EMBLICA (also an antioxidant), monobenzone (a depigmenting agent), kojic acid, arbutin, ascorbic acid and derivatives thereof (e.g., magnesium ascorbyl phosphate or sodium ascorbyl phosphate), and extracts (e.g., mulberry extract, placental extract). In an additional embodiment, skin lightening agents include, without limitation, those described in WO 95/34280, WO 95/07432, and WO 95/23780.

In an embodiment, vitamins include, without limitation, Vitamin A and derivatives thereof (including, for example, retinol, see anti-wrinkling actives), ascorbic acid (Vitamin C and derivatives), Vitamin B (e.g., riboflavin, vitamin $B_2$), biotin, Vitamin D (all forms), Vitamin E and derivatives thereof such as tocopheryl acetate, beta-carotene, panthothenic acid and more. In a further embodiment, anti-acne actives include, without limitation, benzoyl peroxide, erythromycin, clindamycin phosphate, 5,7-dichloro-8-hydroxyquinoline, resorcinol, resorcinol acetate, salicylic acid, azaleic acid, long chain dicarboxylic acids, sulfur, zinc, various natural agents such as those derived from green tree, and more. Other non-limiting examples of suitable anti-acne actives for use herein are described in U.S. Pat. No. 5,607, 980, which description is incorporated herein by reference. In an embodiment, anti-skin wrinkling actives include, without limitation, a variety of agents, often in combination, that prevent or treat wrinkling through a variety of actions, including, without limitation, cosmetic products that contain hydroxy acids, retinol, retinoic, retinol palmitate, a derivative of vitamin A, (or its stronger, prescribed version Retin-A and Renova), bicyclic aromatic compounds with retinoid-type activity, including, without limitation, those described in EP 679 630. In an embodiment, antioxidants include, without limitation, vitamin C, vitamin E and coenzyme Q-10. In a further embodiment, a additional agent can include, without limitation, Botox (an extremely diluted form of botulinum toxin).

In an embodiment, anti-skin aging or anti-wrinkling actives include, without limitation, bicyclic aromatic compounds, compounds which have retinoid-type activity, free-radical scavengers, hydroxy or keto acids or derivatives thereof. In a further embodiment, a "free-radical scavenger" includes, without limitation, α-tocopherol, superoxide dismutase, ubiquinol or certain metal-chelating agents. In an additional embodiment, hydroxy acids include, without limitation, α-hydroxy acids such as lactic acid and glycolic acid or β-hydroxy acids such as salicylic acid and salicylic acid derivatives such as the octanoyl derivative; other hydroxy acids and keto acids include, without limitation, malic, citric, mandelic, tartaric or glyceric acids or the salts, amides or esters thereof. In a further embodiment, anti-wrinkling agents and anti-skin aging agents include, without limitation, sulfur-containing D and L amino acids and their derivatives and salts, particularly the N-acetyl derivatives, a preferred example of which is N-acetyl-L-cysteine; thiols, e.g. ethane thiol; fat-soluble vitamins, ascorbyl palmitate, ceramides, pseudoceramides (e.g., pseudoceramides described in U.S. Pat. Nos. 5,198,210; 4,778,823; 4,985,547; 5,175,321, all of which are incorporated by reference herein), phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. In an embodiment, fatty acids and/or alcohols include, without limitation, straight or branched alkyl chains containing 12 20 carbon atoms and linoleic acid. In a further embodiment, anti-wrinkle actives include, without limitation, those described in U.S. Pat. No. 6,217,888, which description is incorporated herein by reference.

In an embodiment, skin whitening actives include, without limitation, skin lighteners and skin bleaching. In an embodiment, skin whitening actives include, without limitation, hydroquinone, arbutin, koiic acid, azelaic acid, vitamin c, *cinnamomum subavenium*, alpha hydroxyl acids ("AHA's"), niacinamide and licorice extract (including, without limitation, glabridin). In an embodiment, skin whitening actives include depigmentation agents, including topical creams that contain the organic compound monobenzone or the chemical mequinol.

In an embodiment an an additional agent is a hindered amine light stabilizers, also referred to as "HALS." HALS are derivatives of 2,2,6,6-tetramethyl piperidine and are extremely efficient stabilizers against light-induced degradation of most polymers. HALS do not absorb UV radiation, but act to inhibit degradation of the polymer. They slow down the photochemically initiated degradation reactions, to some extent in a similar way to antioxidants. In an embodiment, a significant level of stabilization is achieved at relatively low concentrations.

In an embodiment, sunscreen composition that is encapsulated in a cellulose derived capsule are used in products exposed to the sun's UV radiation. In a further embodiment, the products include, without limitation, plastics, including, without limitation, natural, synthetic or semi-synthetic organic solids that are moldable. In a further embodiment, a plastic includes, without limitation, thermoplastics and thermosetting plastics and include, without limitation, polyethylene, polyamides, polyethylene terephthalate, polyesters, acrylonitrile butadiene styrene, polycarbonate, polyurethane, polypropylene, melamine formadehyde, phenolics, polyetheretherketone, polyetherimide, polylactic acid, polymethyl methacrylate, polytetrafluoroethylene, urea-formaldehyde, polystyrene, polyvinyl chloride and polytetrafluoroethylene. In an embodiment, a plastic can be biodegradable or not. In a further embodiment, a plastic includes vinyl or other plastics used in consumer products, including without limitation, automobiles, including, without limitation, seats, dashboard, molding and/or trim.

In an embodiment, sunscreen composition that is encapsulated in a cellulose derived capsule are used in paints. In a further embodiment, a paint including an encapsulated sunscreen composition includes one or more additional agents, including, without limitation, HALS.

In an embodiment, a sunscreen composition that is encapsulated in a cellulose derived capsule are used in products used by the military, police or other governmental or non-governmental force. In an embodiment, a product used by the by the military, police or other governmental or non-governmental force includes, without limitation, sunscreen, paint, clothes, weapons, including, without limitation, weapons containing composite or other synthetic parts, and other by the military, police or other governmental or non-governmental force products. In an embodiment, a sunscreen composition that is encapsulated in a cellulose derived capsule used for by the military, police or other governmental or non-governmental force includes a reflective agent and/or an agent capable of preventing the detection of infrared radiation by an individual or equipment.

In an embodiment, cascading antioxidants include, without limitation, emblica and synovia. In an embodiment, quencher actives are are used for singlet and triplet excited electron stabilization caused from photons of energy and to reduce or eliminate degradation. In an embodiment, quencher actives include, without limitation, electron receptors, including, without limitation, Polycrylene. In an embodiment, an infrared reflective coating comprises an agent that reflects infrared radiation, for instance, without limitation, at a wavelength between about 0.74 μm to about 300 ρn. In a further embodiment, an infrared reflective coating includes, without limitation, coatings which produce different amounts of gloss and reflection. In a further embodiment, a sunscreen composition with an infrared reflective coating is used by a soldier, police, national guard, governmental agent, including, without limitation, an individual working for the Federal Bureau of Investigation, Alcohol, and Tobacco & Firearms, Secret Service, Central Intelligence Agency, Department of Justice or any other governmental agent, whether located in the United States or outside the United States or other individuals who requires an infrared reflective coating.

In an embodiment, anti-inflammatory actives include, without limitation, steroidal, non-steroidal, and other compounds. In a further embodiment, steroidal anti-inflammatory agents include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In an additional embodiment, a steroidal anti-inflammatory for use is hydrocortisone.

In an embodiment, nonsteroidal anti-inflammatory agents include, without limitation, oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (Astrazeneca and NicOx), Celecoxib (Pharmacia Corp.) (4-[5-(4-methylphenyl)-3-(trifluoromethyl)-1H-pyrazol-1-yl] benzenesulfonamide), Meloxicam (Boehringer Ingelheim Pharmaceuticals) (4-hydroxy-2-methyl-N-(5-methyl-2-thiazolyl)-2H-1,2GW-406381 (Glaxosmithkline), Etoricoxib (Merck & Co.), Rofecoxib (MERCK & Co.) (4-[4-(methylsulfonyl) phenyl]-3-phenyl-2(5H)-furanone), Lumiracoxib (Novartis Pharma AG), Valdecoxib (Pharmacia Corp.) (4-(5-methyl-3-phenyl-4-isox-azolyl) benzenesulfonamide), and Etodolac (Wyeth Ayerst Laboratories) ((±) 1,8-diethyl-1,3,4,9-tetrahydropyrano-[3,4-b]acid).

In a further embodiment, anti-inflammatory or other skin active agents include, without limitation, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

In an embodiment, anesthetic actives include, without limitation, butamben picrate, lidocaine, xylocalne, benzocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

In an embodiment, analgesic actives include, without limitation, dyclonine hydrochloride, aloe vera, fentanyl, capsaicin, and the like. In an embodiment, anti-pruritic actives include, without limitation, alclometasone dipropionate, betamethasone valerate, and isopropyl myristate MSD. In an embodiment, anti-microbial actives include, without limitation, antifungal, antibacterial, and antiseptic compounds. Antifungal compounds include, but are not limited to, compounds such as imidazole antifungals. Specific antifungals include butocouazole nitrate, miconazole, econazole, ketoconazole, oxiconizole, haloprogin, clotrimazole, and butenafine HCl, naftifine, terbinafine, ciclopirox, and tolnaftate. Antibacterial and antiseptic compounds include phenol-TEA complex, mupirocin, triclosan, chlorocresol, chlorbutol, iodine, clindamycin, CAE (Anjinomoto Co., Inc., containing DL-pyrrolidone Carboxylic acid salt of L-Cocoyl Arginine Ethyl Ester), povidone-iodine, polymyxin b sulfate-bacitracin, zinc-neomycin sulfate-hydrocortisone, chloramphenicol, methylbenzethonium chloride, and erythromycin and antiseptics (e.g., benzalkonium chloride, benzethonium chloride, chlorhexidine gluconate, mafenide acetate, nitrofurazone, nitromersol, antimicrobial deodorant compounds, antiparasitics, including, without limitation, lindane and the like may be included in compositions of the invention.

In a further embodiment, antimicrobial and antifungal actives include, without limitation, β-lactam drugs, quinolone drugs, ciprofloxacin, norfloxacin, tetracycline, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

In an embodiment, anti-viral agents include, without limitation, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. No. 09/421,084 (Beerse et al.); Ser. No. 09/421,131 (Biedermann et al.); Ser. No. 09/420,646 (Morgan et al.); and Ser. No. 09/421,179 (Page et al.), which were each filed on Oct. 19, 1999.

In an embodiment, anti-allergenics include, without limitation, antihistamines. In a further embodiment, antihistamines are, without limitation, $H_1$ or $H_2$ antagonists or other types of histamine release inhibitors. In an additional embodiment, $H_1$ antagonists are sedating or non-sedating, including, without limitation, diphenhydramine (Benadryl), chlorpheniramine, tripelennamine, promethazine, clemastine, doxylamine, benadryl and more. In a further embodiment, $H_1$-non-sedating antihistamines include, without limitation, astemizole, terfenadine, loratadine etc. Examples of $H_2$ antagonists include cimetadine, famotidine, nizatidine, and ranitidine. In an additional embodiment, histamine-release-inhibitors include, without limitation, cromolyn.

In a further embodiment, an active is a medicinal for treatment of dermatological conditions such as psoriasis, acne, eczema, and other skin conditions due to disease, pathology, accident, and the like and include, without limitation, burn relief ointments, such as o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; herpes treatment drugs, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as 2-(acetyloxy)-9-fluoro-1',2',3',4'-tetrahydro-11-hydroxy-pregna-1,4-dieno [16,17-b]naphthalene-3,20-dione and 21-chloro-9-fluoro-1',2',3',4'-tetrahydro-11 b-hydroxy-pregna-1,4-dieno[16z, 17-b]naphthalene-3,20-dione, and others including those that are antiinflammatories. In an additional embodiment, medicinals include, without limitation, those useful in the treatment of exposure to poison oak, poison ivy, poison sumac, and the like. These include camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate. In an embodiment, other medication capable of topical administration can be incorporated in a composition of the present invention in an amount sufficient to perform its intended function.

In an embodiment, anticellulite actives include, without limitation, isobutylmethylxanthine, caffeine, theophylline, theobromine, aminophylline, yohimbine, and mixtures thereof. In an embodiment, examples of actives suitable for treating hair loss include, without limitation, potassium channel openers or peripheral vasodilators such as minoxidil, diazoxide, and compounds such as N*-cyano-N-(tert-pentyl)-N'-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin El and prostaglandin F2-alpha; fatty acids, such as oleic acid; diuretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, *ginseng*, rehmannia, swertia, sweet orange, zanthoxylum, Serenoa *repens* (saw palmetto), Hypoxis rooperi, stinging nettle, pumpkin seeds, and rye pollen; other botanical extracts including sandlewood, red beet root, *chrysanthemum*, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof. Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

In an embodiment, actives suitable for use in inhibiting hair growth include, without limitation, serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, alpha-tocophenol and derivatives thereof, or mixtures thereof.

In an embodiment, hair bleaching agents include, without limitation, perborate or persulfate salts.

In an embodiment, a sunscreen composition protects against UV radiation given off by man made devices. In a further embodiment, a sunscreen composition protects against UV radiation given off by fluorescent light bulbs, wherein the protective coating applied to a fluorescent light bulb has gaps through which UV radiation is emitted.

In an embodiment, deodorant compounds include, without limitation, astringent salts and bioactive compounds. In an additional embodiment, astringent salts include, without limitation, organic and inorganic salts of aluminum, zirconium, zinc, and mixtures thereof. In an additional embodiment, anions of the astringent salt include, without limitaiton, sulfate, chloride, chlorohydroxide, alum, formate, lactate, benzyl sulfonate or phenyl sulfonate. In an embodiment, antiperspirant astringent salts include, without limitation, aluminum halides, aluminum hydroxyhalides, zirconyl oxyhalides, zirconyl hydroxyhalides, and mixtures thereof. In a further embodiment, aluminum salts include, without limitation, aluminum chloride and the aluminum hydroxyhalides having the general formula $Al_2(OH)_xQ_yXH_2O$, wherein Q is chlorine, bromine or iodine; x is about 2 to about 5; x+y is about 6, wherein x and y are not necessarily integers; and X is about 1 to about 6. In a further embodiment, zirconium compounds include, without limitation, zirconium oxy salts and zirconium hydroxy salts, also referred to as zirconyl salts and zirconyl hydroxy salts, and represented by the general empirical formula $ZrO(OH)_2 2-nz L_z$, wherein z varies from about 0.9 to about 2 and is not necessarily an integer; n is the valence of L; 2-nz is greater than or equal to 0; and L is selected, without limitation, from the group consisting of halides, nitrate, sulfamate, sulfate, and mixtures thereof.

In an embodiment, deodorant compounds include, without limitation, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, numerous other useful antiperspirant compounds listed in the CTFA Handbook at p. 56, incorporated herein by reference, and mixtures thereof.

In an embodiment, the deodorant compound includes, without limitation, a bacteriostatic quaternary ammonium compound, such as, for example, without limitation, cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetralkylammonium carbonates and bicarbonates. In a further embodiment, deodorant compounds include, without limitation, chlorophyllin copper complex, aluminum chloride, aluminum chloride hexahydrate, and methylbenzethonium chloride.

In an embodiment, antioxidants include, without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, tocotrienols and their esters, and 6-hydroxy-2,5,7,8-tetramethylchroman-2-carboxylic acid (commercially available under the tradename TROLOX). Other suitable antioxidants include uric acid and its salts and alkyl esters, sorbic acid and its salts, lipoic acid, amines (e.g., N,N-diethylhydroxylamine, amino-guanidine), sulfhydryl compounds (e.g., glutathione, N-acetyl cysteine), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

In a further embodiment, antioxidants include, without limitation, photostable antioxidants, including, without limitation, a photostable antioxidant marketed under the tradename EMBLICA by EMD Chemicals. In an embodiment, antioxidants, including, without limitation, photostable antioxidants (e.g., EMBLICA), are included in a sunscreen composition at about 0.05 to about 5% (w/v), or about 0.05 to about 2% (w/v), or about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.25%, 4.5%, 4.75%, or 5% (w/v), or in a bodywash, shampoo, conditioner, gel, soap, hand sanitizer, cream, lotion, spray or mousse with or without a sunscreen active agent at about 0.02 to about 2% (w/v), or about 0.02 to about 1% (w/v), or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2% or more.

In an embodiment, insect repellants include, without limitation, N,N-Diethyl-m-toluamide, frequently called "DEET" and available in the form of a concentrate containing at least about 95 percent DEET, dimethyl phthalate, ethyl hexanediol, indalone, di-n-propylisocinchoronat-e, bicycloheptene, dicarboximide and tetrahydrofuraldehyde. In a further embodiment, plant-derived materials with insect repellent activity include, without limitation, citronella oil and other sources of citronella (including lemon grass oil), limonene, rosemary oil and *eucalyptus* oil. Choice of an insect repellent will frequently be influenced by the odor of the repellent. In a further embodiment, DEET is used at high concentrations, including, without limitation, up to about 15% or more, while plant-derived substances are typically used in much lower amounts, such as 0.1% or less.

In an embodiment, skin care agents include, without limitation, those found in the CTFA Cosmetic Ingredient Handbook, Seventh Edition, 1997 and the Eighth Edition, 2000 and Remington's Pharmaceutical Sciences, 20th Ed., Lippincott Williams & Witkins, Baltimore, Md. (2000) (hereinafter Remington's), U.S. Pharmacopeia and National Formulary, The United States Pharmacopeial Convention, Inc., Rockville, Md. and Physician's Desk Reference, Medical Economics Co., Inc., Oradell, N.J. all of which are incorporated herein by reference.

In an embodiment, the invention provides cellulose derived capsules, including, without limitation, microcapsules, that act as a protective barrier on the skin when used either alone, or as an additive in a bodywash, shampoo, conditioner, gel, soap, hand sanitizer, cream, lotion, spray and mousse. In these embodiments, the cellulose derived capsules, including, without limitation, microcapsules, may be used without any additional active ingredients (i.e., empty), providing a physical barrier, or they may be used with additional encapsulated sunscreen active agents and additional agents that enhance their barrier function. In an embodiment, the cellulose derived capsules, including, without limitation, microcapsules, contain one or more agents that absorb radiation, such as graphite, lead, tungsten, and others known in the art, or agents that reflect radiation such as ceramic beads. In an embodiment, because the cellulose derived capsules, including, without limitation, microcapsules, are designed so as to experience minimal or no breakage when applied to the skin, as well as to experience minimal penetration of the skin, it is possible to use even toxic substances (e.g., lead) that provide a screening effect. The cellulose derived capsules, including, without limitation, microcapsules, are eventually removed from the skin through repeated washing and/or normal sloughing of the external skin cell layers. Especially for agents used for one-time or very few exposures, such as can occur for personnel engaged in combating or containing terrorist attacks or in warfare, the invention provides a means to deliver a last line of defense on the skin of personnel where the active used in the microcapsules may be one that is not appropriate for long-term use, but that is appropriate for a limited number of applications in order to protect the wearer from a greater risk (e.g., cellulose derived capsules, including, without limitation, microcapsules, encapsulating lead to protect against a radiation attack).

In an embodiment, the cellulose derived capsules, including, without limitation, microcapsules, is prepared so to experience no or minimal breakage when applied to the skin, either as is or in the form of a bodywash, shampoo, conditioner, gel, soap, hand sanitizer, cream, lotion, spray or mousse. In a further embodiment, the cellulose derived capsules, including, without limitation, microcapsules, is prepared so to experience various degrees of breakage, on average, when applied as is or in a bodywash, shampoo, conditioner, gel, soap, hand sanitizer, cream, spray or mousse. In an embodiment, the cellulose derived capsules, including, without limitation, microcapsules, is prepared so as to experience about 0% breakage, or breakage in a range from about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% after application (or application and rinsing in the case of a bodywash, shampoo, conditioner, gel, soap, hand sanitizer, cream, and possibly with a lotion, spray or mousse containing the the cellulose derived capsules, including, without limitation, microcapsules,). In a further embodiment, the the cellulose derived capsules, including, without limitation, microcapsules, are formulated so as to break open in response to conditions that occur on the skin, so that after application the the cellulose derived capsules, including, without limitation, microcapsules, act to release their contents in a time-release or controlled manner. In an embodiment, skin or hair conditions can vary with the user's environment, the variation of which can trigger breakage of microcapsules, include pH, temperature, friction, exposure to light or air, pressure, and the like.

In an embodiment the sunscreen composition, includes, without limitation, a cationic component, including, without limitation, cationic polymers. In an embodiment, cationic components, including, without limitation, cationic polymers, include, without limitation, those described in U.S. Pat. Nos. 6,224,852; 3,816,616; 4,272,515; 4,298,494; 4,080,310; 4,048,301; 4,009,256; and 3,186,911, those available commercially including, without limitation, from Union Carbide Corp. under the trademark POLYMER JR., from Celanese-Stein Hall under the trademark JAGUAR, from GAF Corporation under the tradename Gafquatm and from Merck & Co., Inc under the trademark MERQUAT by. In a further embodiment, a cationic component includes, without limitation, Merquat 100, a highly charged cationic dimethyldiallylammonium chloride homopolymer, and MERQUAT™ 550, a highly charged cationic copolymer prepared with dimethyldiallylammonium chloride and acrylamide. These materials are designated in the CTFA dictionary as Quaternium40 and Quaternium-41, respectively.

In an embodiment, the sunscreen composition includes, without limitation, polyquaterniums. In a further embodiment, the sunscreen composition includes, without limitation, quaternized material in powder form, including, but not limited to, the polyquaterniums. In an additional embodiment, polyquaterniums include, but are not limited to, polyquaternium-4, -7, -11, -22, -37, -44, -5, and -64 and CELQUAT L-200 for polyquaternium-4. Useful in some embodiments of the invention is a dry cationic component, such as sold under the tradename CAE (Anjinomoto Co., Inc.), containing DL-pyrrolidone Carboxylic acid salt of L-Cocoyl Arginine Ethyl Ester, which is a cationic agent useful for binding to proteins and providing an antimicrobial effect. In an embodiment, a sunscreen composition includes, without limitation, a cationic component, including, without limitation, a cationic polymer that comprises about 0.1 to about 20%, or about 0.1 to about 10%, or about 0.5 to about 10%, or about 1 to about 10%, or about 0.5 to about 5%, or about 0.5 to about 3% or about 1 to about 5%, or about 1 to about 3%, or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more of the total sunscreen composition. In an additional embodiment, the cationic component is polyquaternium-4. In another embodiment, the polyquaternium-4 is present at about 1% (w/v) of the sunscreen composition.

In an embodiment, a bodywash, shampoo, conditioner, gel, soap, hand sanitizer, cream, lotion, spray or mousse combined with a sunscreen composition includes, without limitation, a cationic component, including, without limitation, a cationic polymer that comprises about 0.1 to about 20%, or about 0.1 to about 10%, or about 0.5 to about 10%, or about 1 to about 10%, or about 0.5 to about 5%, or about 0.5 to about 3% or about 1 to about 5%, or about 1 to about 3%, or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more of the total sunscreen composition. In an additional embodiment, the cationic component is polyquaternium-4. In another embodiment, the polyquaternium-4 is present at about 1% (w/v) of the sunscreen composition. In an embodiment, a bodywash, shampoo, conditioner, gel, soap, hand sanitizer, cream, lotion, spray or mousse combined with a sunscreen composition includes, without limitation, a cationic component, including, without limitation, a cationic polymer that comprises about 0.03 to about 7%, or about 0.03 to about 4%, or about 0.2 to about 4%, or about 0.3 to about 4%, or about 0.2 to about 2%, or about 0.3 to about 4%, or about 0.3 to about 1%, or about 0.3 or 0.4% of the total composition. In some embodiments, the cationic component is polyquaternium-4; in some embodiments the polyquaternium-4 is present at about 0.33% (w/v) of the total combined composition.

In an embodiment, a sunscreen composition includes, without limitation, a film barrier system, typically a hydrophobic layer that serves to maintain the residual sunscreen after rinse. In an embodiment, a film barrier system includes, without limitation, petrolatum, silicon derivatives, polymers, including, without limitation, those with carboxylic ends. In a further embodiment, a film former includes, without limitation, emollient esters, lanolin derivatives (e.g., acetylated lanolins), and superfatted oils. In an additional embodiment, a film former includes, without limitation, MOISTUREGUARD™, which contains petrolatum, dimethicone, stearamidopropyl dimethylamine stearate, and tocopheryl acetate, available from Engelhard.

In an embodiment, a sunscreen composition includes, without limitation, an acrylic co-polymer as a film former. An additional embodiment, a sunscreen composition includes, without limitation, a liquid acrylic copolymer formulation, including, without limitation, DERMACRYL, marketed by National Starch and Chemical. Acrylic co-polymers may be included in sunscreen additives at about 0.1 to about 5%, or about 0.2 to about 3%, or about 0.2%, 0.3%, 0.4%, or 0.5%, or in sunscreen/bodywashes at about 0.05 to about 2%, or about 0.1 to about 1%, or about 0.05%, 0.1%, 0.2%, 0.3%, 0.4%, or 0.5% or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10% or more.

In an embodiment, a secondary film former can be included in a sunscreen composition and include, without limitation, keratin or other protein derivative in an amino acid complex such as cysteine. In an embodiment, a film former is present in a sunscreen composition in the range of about 0.1 to about 25%, or about 1 to about 10%; or about 2 to about 6%; or about 3, 4, or 5% or about about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more. In an additional embodiment, a film former, including, without limitation, MoistureGuard is used at a concentration of about 4.2%. In a further embodiment, a film former is used at a 4.2% concentration.

In an embodiment, an agent can have more than one function. For example, without limitation, inorganic blockers such as Tioveil and Spectraveil (both of the Tioxide Group), can act as film-formers and other advantageous uses here. In addition, many emollients may also perform a film former function in that they provide a barrier on the skin. Thus, in a further embodiment, a sunscreen composition includes, without limitation, water-insoluble emollients that include, without limitation, fatty acids such as oleic and stearic; fatty alcohols such as cetyl, and hexadecyl (ENJAY); esters such as diisopropyl adipate, benzoic acid esters of $C_9$-$C_{15}$ alcohols, and isononyl iso-nonanoate; alkanes such as mineral oil; silicones; such as dimethyl polysiloxane and ethers such as polyoxypropylene butyl ethers and polyoxypropylene cetyl ethers. In an embodiment, a water-insoluble emollient is used at a concentration from about 2% to about 15% by weight, 4% to about 10% or about about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more (w/v) of the composition. In a further embodiment film formers include, without limitation, polythylenes, including, without limitation, those available from New Phase Technologies as PERFORMALENE 400, a polyethylene having a molecular weight of 400 or polyethylene 2000 (molecular weight of 2000), which is available from New Phase Technologies as PERFORMALENE 2000. In an additional embodiment, a suitable film former/waterproofing agent includes, without limitation, synthetic wax, also available from New Phase Technologies as PERFORMA V-825 octadecene/MA copolymer or any film former chemistry known in the art. In an embodiment, film formers include, without limitation, acacia gum, cellulose derivatives, guar derivatives and all those set forth on pages 68 69 of the C.T.F.A. Cosmetic Ingredient Handbook, First Edition, 1988, which is hereby incorporated by reference. Such film formers include acrylamides copolymer, acrylamide/sodium aciylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic anhydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenean, calcium/sodium PVM/MA copolymer, carboxymethyl hydroxyethyl cellulose, cellulose gum, collodion, copal, corn starch/aciylainide/sodium acrylate copolymer, damar, diethylene glycolamine/epichlorohydrin/piperazine copolymer, DMJ-IF, dodecanedoic acid/cetearyl alcoholglycol copolymer, ethylcellulose, ethylene/acrylate copolymer, ethylene/maleic anhydride copolymer, ethylene/vinyl acetate copolymer, ethyl ester of PVM/fvIA copolymer, flexible collodian, gum benzoin, gutta percha, hydroxybutyl methylceflu lose, hydroxyethylcellulose, hydroxyethyl ethyl cellulose, hydroxypropylceilulose, hydroxypropyl guar, hydroxypropyl methylcellulose, isopropyl ester of PVM/MA copolymer, maltodextrin, melamine/formaldehyde resin, methacryloyl ethyl betainelmethacrylates copolymer, nitrocellulose, octylacrylamide/acrylates/butylaminoethylmethaciylate copolymer, octylacrylamide/acrylates copolymer, phthalic anhydride/glycerin/gycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium- 14, Polyquaternium-15, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methaciylate copolymer, sucrose benzoate/sucrose acetate isobutyrate copolymer, toluenesulfonamide/formaldehyde resin, tragacath gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, zein and those set forth in U.S. Pat. Nos. 6,838,419; 6,838,088; 6,780,422; 6,531,118; and 5,916,541, all of which are incorporated herein by reference.

In an embodiment, a sunscreen composition includes, without limitation, a wide variety of additional components selected so as to avoid any undesirable reaction with the primary components (e.g., one or more of the sunscreen active agents) of the composition. The CTFA Cosmetic Ingredient Handbook, Seventh Edition, 1997 and the Eighth Edition, 2000 (incorporated by reference herein), provide a broad source of possible cosmetic and pharmaceutical ingredients typically used in skin care compositions. In an embodiment, additional components include, without limitation, one or more of the following: Absorbents, abrasives, anticaking agents, antifoaming agents, binders, biological additives, buffering agents, bulking agents, chelating agents/sequestrants (e.g., disodium EDTA), chemical additives, colorants, cosmetic astringents, cosmetic biocides, denaturants, drug astringents, emollients (including glycerin alovera, and Vitamins A, C, and D [hydrating agents and skin protectants]), foam boosters, fragrance components, gums, humectants/moisturizers (including urea, guanidine, glycolic acid, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof), hydrotropes, neutralizing agents, opacifying agents and pigments, pH adjusters, plasticizers, preservatives, propellants, reducing agents, skin bleaching agents, skin protectants, solubilizing agents, and suspending agents (e.g., Carbomer 1382).

In an embodiment, the sunscreen composition includes, without limitation, a preservative, including, without limitation, citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines (e.g., imidiazolinylurea), triclosan, hydantoins (e.g., dimethyloldimethylhydantoin), isothiazolidinone compounds and mixtures thereof, KATHON CG and KATHON CGII, which contain methylchloroisothiazolinone and methylisothiazolinone (Rohm and Haas). In an embodiment, the quantity of preservative is in the range from 0.001 to 2%, preferably from 0.01 to 0.2% or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more.

In an embodiment, a sunscreen composition includes, without limitation, a chelating agent. In a further embodiment, chelating agents include, without limitation, substances used to chelate or bind metallic ions, such as with a heterocyclic ring structure so that the ion is held by chemical bonds from each of the participating rings. In a further embodiment, chelating agents include, without limitation, ethylene diaminetetraacetic acid (EDTA), EDTA disodium, calcium disodium edetate, EDTA trisodium, EDTA tetrasodium and EDTA dipotassium. In an embodiment, one or more chelating agents is included in a sunscreen composition in amounts ranging from about 0.001 to about 0.2 weight percent, or about 0.01% w/v or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more (w/v).

In an embodiment, a sunscreen composition includes, without limitation, thickening agents or gellants to adjust the texture and viscosity of the composition. In an embodiment, thickening agents or gellants include, without limitation, CARBOPOL™ resins [e.g., 934, 971, 974, 980, 981] and PEMULEN™ [TR-1 and TR-2] [both CARBOPOL™ and PEMULEN™ are registered trademarks of BF Goodrich], Noveon AA-1, ETD resins, and ULTREZ™ resins [registered trademark, BF Goodrich] or carbomers.

In an embodiment, a sunscreen composition includes, without limitation a non-polar wax, including, without limitation, ester waxes, diester waxes, hydrocarbon waxes, silicone waxes and triglyceride waxes and mixtures thereof. In another embodiment, a sunscreen composition includes, without limitation, a liquid hydrocarbon (similar to pentane), and/or a cationic foaming agent derived from arginine and or cysteine.

In an embodiment, additional ingredients which can be present in a sunscreen composition include, without limitation, fragrance, dyes, antimicrobial materials such as triclocarban, triclosan, iodophors, iodine formulations, phenolic compounds, e.g. hexachlorophene, and bisbiguanides, e.g. chlorhexidene gluconate, and the like. See, e.g. U.S. Pat. Nos. 6,827,795; 6,517,854; 6,010,817; 5,173,216; 5,719,113; 5,259,984; 5,562,912; 5,629,006; 5,728,662; 5,767,163; 5,750,579; 5,591,442; 5,650,143; 5,772,640; and 4,478,821.

In an embodiment, the components comprising a sunscreen composition are mixed in, without limitation, water or oil. In an embodiment, a sunscreen composition or sunscreen composition combined with a bodywash, shampoo, conditioner, gel, soap, hand sanitizer, cream, lotion, spray or mousse includes, without limitation, one or more surfactants. The use of surfactants in bodywashes is well-known in the art. Any surfactant known in the art and appropriate for a bodywash, shampoo, conditioner, gel, soap, hand sanitizer, cream, lotion, spray or mousse may be used. See, McCutcheon's Detergents & Emulsifiers, M.C. Publishing Co. (North American edition 1989); Schwartz, et al., Surface Active Agents, Their Chemistry and Technology, New York, Interscience Publishers, 1949, and U.S. Pat. Nos.

6,096,697; 4,741,855; 4,788,066; 5,104,646; 5,106,609; 2,658,072; 2,438,091; 2,528,378; 2,486,921; 2,486,922; 2,396,278; 2,979,465; 3,179,599; 5,322,643; 5,084,212; 3,332,880; 4,122,029; 4,265,878; 4,421,769; 3,929,678; 3,959,461; 4,387,090; 4,303,543; and 6,224,852; and in British Patent Nos. 848,224 and 791,415. Also see CTFA Cosmetic Ingredient Dictionary, 4th Edition 1991, pages 509 514 for various long chain alkyl cationic surfactants; and Richmond, James M., Cationic Surfactants, Marcel Dekker, Inc., New York and Basel, 1990.

In an embodiment, surfactant(s) includes, without limitation, cationic, anionic, nonionic, zwitterionic, amphoteric, or any combination of surfactants thereof. In a further embodiment, surfactants include, without limitation, alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. In a further embodiment, alkyl sulfates include, without limitation, sodium, ammonium, potassium, magnesium, or TEA salts of lauryl or myristyl sulfate or ammonium, sodium, magnesium, or TEA laureth-3 sulfate.

In an embodiment, a sunscreen composition has a surfactant concentration of about 0.01% to about 10% (w/v). In a further embodiment, a sunscreen composition has a surfactant concentration of about 3% to about 5%. In a further embodiment, a sunscreen composition has a surfactant concentration of at least 0.01%, at least 0.02%, at least 0.03%, at least 0.04%, at least 0.05%, at least 0.06%, at least 0.07%, at least 0.08%, at least 0.09%, at least 0.1%, at least 0.25%, at least 0.5%, at least 0.75%, at least 1%, at least 1.25%, at least 1.5%, at least 1.75%, at least 2%, at least 2.25%, at least 2.5%, at least 2.75%, at least 3%, at least 3.25%, at least 3.5%, at least 3.75%, at least 4%, at least 4.25%, at least 4.5%, at least 4.75%, at least 5%, at least 5.25%, at least 5.5%, at least 5.75%, at least 6%, at least 6.25%, at least 6.5%, at least 6.75%, at least 7%, at least 7.25%, at least 7.5%, at least 7.75%, at least 8%, at least 8.25%, at least 8.5%, at least 8.75%, at least 9%, at least 9.25%, at least 9.5%, at least 9.75%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25% (w/v).

In an embodiment, a sunscreen composition with a surfactant concentration of about 0.01% to about 5% or about 3% to about 5% and wherein the sunscreen active agent or agents are encapsulated within a cellulose derived capsule when applied to the wet skin of an individual spreads across the surface to which the sunscreen composition is applied with the same degree of evenness and ease as a sunscreen composition with a higher concentration of surfactant. In a further embodiment, a sunscreen composition with a surfactant concentration of about 0.01% to about 5% or about 3% to about 5% lathers less than a sunscreen composition with a higher surfactant concentration. In an embodiment, a sunscreen composition with a surfactant concentration of about 0.01% to about 5% or about 3% to about 5% also includes film formers, secondary polymers and emulsifiers.

In an embodiment, a surfactant is an environmentally favourable surfactant including, without limitation, dodecyl glucosides.

In an embodiment, a surfactant is a lathering surfactant. In a further embodiment, a lathering surfactant has a log P of less than about 2.5 that produces foam when mixed with and agitated in water. In an additional embodiment, an anionic lathering surfactant is a sulfate, wherein the sulfate is, without limitation, an alkyl sulfate or an alkyl ether sulfate. In a further embodiment, the sulfates include, without limitation, sodium laureth sulfate and ammonium laureth sulfate. Sodium laureth sulfate is an article of commerce available from a number of sources, including under the tradename Steal CS-370 from Stepan. It has a molecular formula $CH_3(CH_2)_{10}CH_2(OCH_2CH_2)_2OSO_3Na$ and conforms to the following structure:

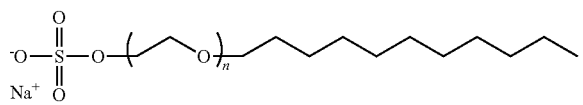

In an embodiment, a sunscreen composition or a bodywash, shampoo, conditioner, gel, soap, hand sanitizer, cream, lotion, spray or mousse combined with a sunscreen composition, includes, without limitation, sodium laureth sulfate at a concentration of from about 10% to about 15% or from about 7.5% to about 8.5%. In a further embodiment, ammonium laureth sulfate is used in combination with an alkyl glucoside, wherein the alkyl glucoside includes, without limitation, decyl glucoside. The combination of ammonium laureth sulfate and decyl glucoside is sold under the tradename Plantaren PS-100 by Cognis. In an embodiment, ammonium laureth sulfate in combination with decyl glucoside is present in a sunscreen composition or a bodywash, shampoo, conditioner, gel, soap, hand sanitizer, cream, lotion, spray or mousse combined with a sunscreen composition at a concentration of from about 5% to about 10%, or from about 7.5% to about 8.5%.

In a further embodiment, a lathering surfactant includes one, two, three or more anionic lathering surfactants, including, without limitation, sulfates, including, without limitation, sodium laureth sulfate and ammonium laureth sulfate. In an embodiment, sodium laureth sulfate and ammonium laureth sulfate are combined with decyl glucoside. In an additional embodiment, the two sulfates are present at a combined concentration of from about 15% to about 25%.

In a further embodiment, anionic surfactants, include, without limitation, sulfated monoglycerides of the form $R1CO-O-CH_2-C(OH)H-CH_2-O-SO_3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine, monoethanolamine and sodium cocomonoglyceride sulfate. In a further embodiment, anionic surfactants include, without limitation, olefin sulfonates of the form $R1SO_3M$, wherein R1 is a mono-olefin having from about 12 to about 24 carbon atoms, and M is a water-soluble cation such as ammonium, sodium, potassium, magnesium, triethanolamine, diethanolamine and monoethanolamine. In an embodiment, a sulfonated olefin is sodium C14/C16 alpha olefin sulfonate. In a further embodiment, anionic surfactants, include, without limitation, linear alkylbenzene sulfonates of the form $R_1-C_6H_4-SO_3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine monoethanolamine and sodium dodecylbenzene sulfonate. In an additional embodiment, anionic surfactants include, without limitation, primary or secondary alkane sulfonates of the form R1 $SO_3$M, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. In a further embodiment, alkane sulfonate include, without limitation, alkali metal or ammonium C 13 C 17 paraffin sulfonates. In an additional embodiment, anionic surfactants include, without limitation, alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

In an embodiment, taurates include, without limitation, taurine, N-alkyltaurines such as the one prepared by reacting dodecylamine with sodium isethionate as detailed in U.S. Pat. No. 2,658,072. In a further embodiment, anionic surfactants include, without limitation, acyl isethionates, including, without limitation, acyl isethionates include ammonium cocoyl isethionate, sodium cocoyl isethionate, sodium lauroyl isethionate, alkylglyceryl ether sulfonates of the form R1-OCH$_2$—C(OH)H—CH$_2$—SO$_3$M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine, sodium cocoglyceryl ether sulfonate, Sulfonated fatty acids of the form R1-CH(SO$_4$)—COOH and sulfonated methyl esters of the from R1-CH(SO$_4$)—CO—O—CH$_3$, where R1 is a saturated or unsaturated, branched or unbranched alkyl group from about 8 to about 24 carbon atoms (e.g., alpha sulphonated coconut fatty acid and lauryl methyl ester); phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.); acyl glutamates corresponding to the formula R1CO—N(COOH)—CH$_2$CH$_2$—CO$_2$M wherein R1 is a saturated or unsaturated, branched or unbranched alkyl or alkenyl group of about 8 to about 24 carbon atoms, and M is a water-soluble cation (e.g., sodium lauroyl glutamate and sodium cocoyl glutamate); alkanoyl sarcosinates corresponding to the formula R1CON(CH$_3$)—CH$_2$CH$_2$—CO$_2$M wherein R1 is a saturated or unsaturated, branched or unbranched alkyl or alkenyl group of about 10 to about 20 carbon atoms, and M is a water-soluble cation (e.g., sodium lauroyl sarcosinate, lauroyl sarcosine, sodium cocoyl sarcosinate, and ammonium lauroyl sarcosinate); alkyl ether carboxylates corresponding to the formula R1-(OCH$_2$CH$_2$)x-OCH$_2$—CO$_2$M wherein R1 is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula R1CO—[O—CH(CH$_3$)—CO]x-CO$_2$M wherein R1 is a saturated or unsaturated, branched or unbranched alkyl or alkenyl group of about 8 to about 24 carbon atoms, x is 3, and M is a water-soluble cation (e.g., sodium cocoyl lactylate); carboxylates, nonlimiting examples of which include sodium lauroyl carboxylate, sodium cocoyl carboxylate, and ammonium lauroyl carboxylate; anionic flourosurfactants; and natural soaps derived from the saponification of vegetable and/or animal fats & oils examples of which include sodium laurate, sodium myristate, palmitate, stearate and tallowate, cocoate. In a further embodiment, a soap is a semi-solid. In another embodiment, a soap includes a wax to form a solid soap bar.

In an embodiment a counter cation, M, is used on the anionic surfactant. In a further embodiment, a counter cation includes, without limitation, sodium, potassium, ammonium, monoethanolamine, diethanolamine, and triethanolamine.

In an embodiment, nonionic surfactants include, without limitation, alkyl glucosides, alkyl polyglucosides, polyhydroxy fatty acid amides, alkoxylated fatty acid esters, sucrose esters, amine oxides, and mixtures thereof. Alkyl glucosides and alkyl polyglucosides are condensation products of long chain alcohols, including, without limitation, C8 30 alcohols, with sugars or starches or sugar or starch polymers, including, without limitation, glycosides or polyglycosides and are represented by the formula (S)$_n$—O—R wherein S is a sugar moiety such as glucose, fructose, mannose, and galactose; n is an integer of from about 1 to about 1000, and R is a C8 30 alkyl group. In an embodiment, long chain alcohols from which the alkyl group can be derived include, without limitation, decyl alcohol, cetyl alcohol, stearyl alcohol, lauryl alcohol, myristyl alcohol, oleyl alcohol, and more. In a further embodiment, these surfactants include, without limitation, those wherein S is a glucose moiety, R is a C8 20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). In an additional embodiment, sucrose ester surfactants include, without limitation, sucrose cocoate and sucrose laurate.

In another embodiment, nonionic surfactants include, without limitation, polyhydroxy fatty acid amide surfactants, more specific examples of which include glucosamides. In an embodiment a process for making compositions containing polyhydroxy fatty acid amides are disclosed, for example, in G.B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934. In an embodiment, nonionic surfactants include, without limitation, amine oxides, including, without limitation, those corresponding to the general formula $R_1R_2$, $R_3$NO, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. In an embodiment, amine oxides include, without limitation, dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

The term "amphoteric surfactant," as used herein, is also intended to encompass zwitterionic surfactants, which are well known to formulators skilled in the art as a subset of amphoteric surfactants.

In an embodiment, amphoteric lathering surfactants include, without limitation, derivatives of aliphatic secondary and tertiary amines, including, without limitation, those wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. In an embodiment, amphoteric or zwitterionic surfactants include, without limitation, betaines, sultaines, hydroxysultaines, alkyliminoacetates, iminodialkanoates, aminoalkanoates, and mixtures thereof. In an embodiment, betaines include, without limitation, the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH($CH_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel). In a further embodiment, sultaines and hydroxysultaines include, without limitation, materials such as cocamidopropyl hydroxysultaine (available as Mirataine CBS from Rhone-Poulenc).

In an embodiment, amphoteric surfactants include, without limitation, the following compounds: Cetyl dimethyl betaine (this material also has the CTFA designation cetyl betaine); Cocamidopropylbetaine; Cocamidopropyl hydroxy sultaine. Examples of other useful amphoteric surfactants are alkyliminoacetates, and iminodialkanoates and aminoalkanoates of the formulas RN[($CH_2$)—$CO_2$-M]$_2$ and RNH($CH_2$)$_m$$CO_2$ M wherein m is from 1 to 4, R is a $C_8$-$C_{22}$ alkyl or alkenyl, and M is H, alkali metal, alkaline earth metal ammonium, alkanolammonium or imidazolinium and ammonium derivatives. In a further embodiment, amphoteric surfactants include, without limitation, sodium 3-dodecyl-aminopropionate, sodium 3-dodecylaminopropane sulfonate. In a further embodiment, N-higher alkyl aspartic acids include, without limitation, those produced according to the teaching of U.S. Pat. No. 2,438,091; and the products sold under the trade name "Miranol" and described in U.S. Pat. No. 2,528,378. In a further embodiment, amphoterics include, without limitation, amphoteric phosphates, such as coamidopropyl PG-dimonium chloride phosphate (commercially available as Monaquat PTC, from Mona Corp.). In another embodiment, amphoacetates include, without limitation, disodium lauroamphodiacetate, sodium lauroamphoacetate, and mixtures thereof.

In an embodiment, a sunscreen composition or a sunscreen composition combined with a bodywash, shampoo, conditioner, gel, soap, hand sanitizer, cream, lotion, spray or mousse include, without limitation, at least one cationic surfactant. In an embodiment, cationic surfactants include, without limitation, fatty amines, di-fatty quaternary amines, tri-fatty quaternary amines, imidazolinium quaternary amines, and combinations thereof. In a further embodiment, fatty amines include, without limitation, monalkyl quaternary amines such as cetyltrimethylammonium bromide. In an embodiment, quaternary amine include, without limitation, dialklamidoethyl hydroxyethylmonium methosulfate, In an embodiment, a sunscreen composition or a sunscreen composition combined with a bodywash, shampoo, conditioner, gel, soap, hand sanitizer, cream, lotion, spray or mousse include, without limitation, stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride. Additional cationic surfactants are disclosed in U.S. Pat. No. 4,303,543 see column 4, lines 58 and column 5, lines 1 42, incorporated herein by references. Also see CTFA Cosmetic Ingredient Dictionary, 4th Edition 1991, pages 509 514 for various long chain alkyl cationic surfactants; incorporated herein by reference.

In an embodiment, the total amount of surfactants, including, without limitation, a cationic surfactant, is present in a sunscreen composition or a sunscreen composition combined with a bodywash, shampoo, conditioner, gel, soap, hand sanitizer, cream, lotion, spray or mousse at about 0.1 to about 20%, or about 0.1 to about 10%, or about 0.1 to about 5%, or about 0.5 to about 5%, or about 1 to about 10%, or about 1 to about 5%, or about 0.1 to about 2%, or about 1 to about 2% or about 0.01% w/v or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more w/v. In addition to surfactants, other ingredients, as described above for additives, may be included in a sunscreen composition combined with a bodywash, shampoo, conditioner, gel, soap, hand sanitizer, cream, lotion, spray or mousse. In an embodiment, soapless cleansers are used in addition to, or instead of, soaps/surfactants, including, without limitation OILATUM™ AD (registered trademark, Stiefel Laboratories) AQUANIL™ (registered trademark, Person & Covey, Inc.), CETAPHIL™ (trademark, Galderma Laboratories, Inc.) or SPECTRODERM™ (registered trademark, Draxis Pharmaceutical Inc.), or their equivalents, may be utilized as a soapless component in the present invention.

In an embodiment, a bodywash is, without limitation, SUAVE Body Wash, which has the following ingredients: Water, Ammonium Lauryl Sulfate, Ammonium Laureth Sulfate, Cocamidopropyl Betaine, Fragrance, Glycerin, Hydrolyzed Milk Protein & Honey Extract, PEG-10 Sunflower Glycerides, Cocamide MEA, Guar Hydroxypropylrimonium Chloride, Acrylates Copolymer, PEG-5 Cocamide, *Helianthus Annuus* (Sunflower) Seed Oil or *Glycine Soja* (Soybean) Oil, Tetrasoidum EDTA, Propylene Glycol, Ammonium Chloride, Sodium Hydroxide, Methylchloroisothiazolinone, Methylisothiazolinone, Titanium Dioxide (CI 77891).

The additional agents and sunscreen active agent in a sunscreen composition are selected for use in a combination product that includes a bodywash, shampoo, conditioner, gel, soap, hand sanitizer, cream, lotion, spray or mousse (a "combination product"), with a combination product applied to the surface of an individual, including an individual's skin and hair. In an embodiment, application can occur during washing in a suitable or effective amount, with application over part or the whole body. A shampoo or conditioner, gel, soap, hand sanitizer, cream, may be applied to hair, though in an embodiment, the shampoo combination product may be rinsed over part or the whole body, with a sunscreen composition adhering to the skin and hair. A selected amount of a combination product may be applied directly to the skin, for instance, without limitation, a lotion, spray or bodywash or may be used through intermediate application to a washcloth, pad, sponge, or other applicator. After lathering, dirt and sloughed-off skin may be washed away by rinsing with water leaving behind one or more of the sunscreen active agents, and in an embodiment, without limitation, a sunscreen active agent encapsulated in a cellulose derived capsule.

In an embodiment, methods for protection of skin from sunlight include, applying a combination product containing a sunscreen active agent, including, without limitation, a sunscreen active agent encapsulated in a cellulose derived capsule, wherein after application of the combination product to an individual's outer surface, including, without limitation, an individual's skin, the skin is protected from sunlight with an average SPF of at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In a further embodiment, the skin is protected from sunlight with an average SPF of at least about 2. In a further embodiment, the skin is protected from sunlight with an average SPF of at least about 5. In a further embodiment, the skin is protected from sunlight with an average SPF of at least about 10. In a further embodiment, the skin is protected from sunlight with an average SPF of at least about 15. In a further embodiment, the combination product is applied more than once; in these cases, the SPF may be cumulative and can increase with the second wash to, e.g., an average of more than 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In a further embodiment, the individual rinses off after application of a combination product, with the SPF following rinsing at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more. In an additional embodiment, a combination product is applied once per day. In a further embodiment, a combination product is applied more than once per day, for example, 2, 3, 4, or more than 4 times per day. In an additional embodiment, a combination product is applied about every other day. In a further embodiment, the combination product is applied about 10, 8, 7, 6, 5, 4, 3, 2 or 1 time per week.

In an embodiment, a sunscreen active agent, including, without limitation, a sunscreen active agent encapsulated in a cellulose derived capsule does not penetrate more than about 1, 2, 5, 7, 10, 15, 20, 25, 30, 35, 40, 45, or 50 microns into the skin of an individual following one application of a combination product. In an additional embodiment, a sunscreen active agent, including, without limitation, a sunscreen active agent encapsulated in a cellulose derived capsule, does not penetrate more than about 1, 2, 5, 7, 10, 15, 20, 25, 30, 35, 40, 45, 50, 60, 70, 80, 90, 100, 120, or 150 microns into the skin, even after repeated applications.

In a further embodiment a sunscreen active agent, including, without limitation, a sunscreen active agent encapsulated in a cellulose derived capsule is designed to penetrate into the skin, and can penetrate to at least about 1, 2, 5, 7, 10, 15, 20, 25, 30, 35, 40, 45, or 50 microns into the skin after one application with a combination product. In a further embodiment, a sunscreen active agent, including, without limitation, a sunscreen active agent encapsulated in a cellulose derived capsule, penetrates more than about 1, 2, 5, 7, 10, 15, 20, 25, 30, 35, 40, 45, 50, 60, 70, 80, 90, 100, 120, or 150 microns into the skin. In a further embodiment penetration occurs following a single application. In a further embodiment, penetration occurs following a single application and rinsing. In a further embodiment, penetration occurs with repeated applications. In a further embodiment, penetration occurs with repeated applications and rinsings.

Any additive described herein, including, without limitation, sunscreen active agents and/or additional agents, generally as a component of a bodywash, shampoo, conditioner, gel, soap, hand sanitizer, cream, lotion, spray or mousse, may be used in the methods of the invention. In an embodiment, the sunscreen active agents and/or additional agents is encapsulated in a cellulose derived capsule. It is understood that a combination product can be applied to an individual's surface, including, without limitation, an individual's skin and/or hair while the skin and/or hair is wet or while it is dry. In an embodiment, the combination product contains one, two or more surface-treated metal oxide pigments that block ultraviolet radiation in the wavelength range of from about 290 nm to about 400 nm. In an additional embodiment, the one, two or more surface-treated metal oxide pigments are present at a combined concentration (based on the total weight of the composition) of at least about 0.1%, 0.2%, 0.3%, 0.4%, 0.5%, 0.6%, 0.7%, 0.8%, 0.9%, 1%, 1.25%, 1.5%, 1.75%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%.

In an embodiment, a sunscreen composition has an inner refractive index of 1.5-1.7, 1.5-1.9, 1.5-2.2, 1.5-2.4 or 1.5-2.6. In a further embodiment, a sunscreen composition has a non-sunscreen active agent with an inner refractive index of 1.5-2.7. In a further embodiment, a sunscreen composition has a non organic dispersed with organic sunscreen active agent with an inner refractive index of 1.5-2.7. In a further embodiment, a sunscreen composition has cellulose derived capsules of different sizes with an inner refractive index of 1.5-2.7. In a further embodiment, a sunscreen composition has a mixture of cellulose derived capsules containing different cellulose derivatives with an inner refractive index of 1.5-2.7. In an embodiment, a sunscreen composition has an overall refractive index of 1.4-2.

Aspects of the present specification may also be described as follows:
1. A sunscreen composition comprising a sunscreen active agent encapsulated in a cellulose derived capsule and one or more additional agents.
2. A sunscreen composition of embodiment 1, wherein a sunscreen composition is combined with a bodywash, shampoo, conditioner, gel, soap, hand sanitizer, cream, spray, mousse or lotion.
3. A sunscreen composition of embodiment 1 or 2, wherein a sunscreen active agent absorbs or blocks UV radiation from about 290 to about 420 nm.

4. A sunscreen composition of any one of embodiments 1-3, wherein a sunscreen active agent is selected from paraamino benzoates, salicylates, cinnamates, benzophenones; and miscellaneous chemicals including menthyl anthralinate and digalloyl trioleate.
5. A sunscreen composition of any one of embodiments 1-3, wherein a sunscreen active agent is selected from p-aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenlyll); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy- or methoxy substituted benzophenones; Uric and vilouric acids; Tannnic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy4,4'-dimethoxybenzophenone, Octabenzone; 4-Isopropyhldibenzoylmethane; Butylmethoxydibenzoylmethane; Etocrylene; and 4-isopropyl-dibenzoylmethane; titanium dioxide, iron oxide, zinc oxide, and mixtures thereof. Other cosmetically-acceptable sunscreens and concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).
6. A sunscreen composition of any one of embodiments 1-3, wherein a sunscreen active agent is a zinc oxide.
7. A sunscreen composition of embodiment 6, wherein a zinc oxide particle is in the range of about 2 to about 50 microns.
8. A sunscreen composition of embodiment 6, wherein a zinc oxide particle is in the range of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more microns.
9. A sunscreen composition of any one of embodiments 6-8, wherein a zinc oxide is surface coated to facilitate dispersion.
10. A sunscreen composition of any one of embodiments 1-3, wherein a sunscreen active agent included in a sunscreen composition in the United States is selected from aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), decamsule, dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), and zinc oxide (25% or less, an inorganic physical blocker of UVA and UVB).
11. A sunscreen composition of any one of embodiments 1-3, wherein a sunscreen active agent included in a sunscreen composition in Euorpe is selected from Cellulosic derived capsules in the 400-700 nm range containing active sunscreen agents PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), Mexoryl XL, Neo heliopan AP, Benzophenone-9, Uvinul T 150, Uvinul A Plus, Uvasorb HEB, Parsol SLX, benzylidene camphor sulfonic acid (6% or less, expressed as acid), octocrylene (10% or less, expressed as acid), polyacrylamidomethyl benzylidene camphor (6% or less), octyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bisbenztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine. (10% or less, also called TINOSORB S).
12. A sunscreen composition of any one of embodiments 1-3, wherein a sunscreen active agent is selected from silicone long-chain molecule with chromophores, e.g., PARASOL SLX (DSM Nutritional Products), which contains benzyl malonate chromophores attached to specific points on a polysiloxane chain. In an additional embodiment, a sunscreen active agent comprises a silicone long-chain molecule with chromophores. In an embodiment, sunscreen compositions include, without limitation, octyl methoxycinnamate, octocrylene, avobenzone, titanium dioxide, and a silicone long-chain molecule with chromophores.

13. A sunscreen composition of embodiment 12, wherein a silicon long-chain molecule is included at a concentration of about 0.5 to about 5%.

14. A sunscreen composition of embodiment 12, wherein a silicon long-chain molecule is included in a combination product at a concentration of about 0.2 to about 2% (w/v).

15. A sunscreen composition of of any one of embodiments 1-15, wherein, a sunscreen active agent is an inorganic physical blocker of UVA solar radiation.

16. A sunscreen composition of any one of embodiments 1-15, wherein a sunscreen active agent is an inorganic physical blocker of UVB solar radiation.

17. A sunscreen composition of any one of embodiments 1-3, wherein a sunscreen active agent is an iron oxide or a polymer.

18. A sunscreen composition of embodiment 17, wherein a polymer is a polyethylene or a polyamide.

19. A sunscreen composition of any one of embodiments 1-3, wherein a sunscreen active agent is selected from cinnamate (e.g., Octylmethoxycinnamate (ethyl hexyl methoxycinnamate), (available under the tradename PARSOL MCX), oxybenzone (e.g., benzophenone-3 (2-Hydroxy4-Methoxybenzophenone), avobenzone (4-tert-Butyl-4'-methoxydibenzoylmethane or PARSOL 1789), octyl salicylate (2-Ethylhexyl Salicylate), octocrylene (2-Ethylhexyl 2-Cyano-3,3-Diphenylacrylate), methyl anthranilate, and/or titanium dioxide, Tineubin or combinations thereof.

20. A sunscreen composition of any one of embodiments 1-3, wherein a sunscreen active agent is a p-methoxycinnamic acid ester.

21. A sunscreen composition of embodiment 20, wherein a sunscreen active agent is selected from amyl p-methoxycinnamate, 2-ethylhexyl p-methoxycinnamate, 2-ethoxyethyl p-methoxycinnamate, diethanolamine p-methoxycinnamate, n-octyl p-methoxycinnamate and propyl p-methoxycinnamate.

22. A sunscreen composition of any one of embodiments 1-21, wherein the composition comprises one, two, three, four or more sunscreen active agents.

23. A sunscreen composition of any one of embodiments 1-3, wherein a second sunscreen active agent is selected from p-aminobenzoic acid, Cinoxate, Avobenzone, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene ethyl 2-cyano-3,3-diphenyl acrylate, octyl salicylate, oxybenzone, Padimate 0, phenylbenzimidazole sulfonic acid, red petrolatum, sulisobenzone, titanium dioxide, zinc oxide, including regular grades and grades of such fine particle size as enable the composition to be translucent or transparent, and triethanolamine salicylate. Additional sunscreen compounds recognized by European authorities include N,N,N-trimethyl-4-(2-oxoborn-3-ylidene methyl)anilinium methyl sulfate, 3-imidazol-4-ylacrylic acid and its ethyl ester, 2-phenylbenzimidazole-5-sulfonic acid and its salts, ethoxylated 4-aminobenzoic acid, amyl 4-dimethylaminobenzoate, 3,3,5-trimethylcyclohexyl-2-acetamidobenzoate, potassium cinnamate, 4-methoxycinnamic acid salts, propyl 4-methoxycinnamate, salicylic acid salts, amyl 4-methoxycinnamate, mexenone, sulisobenzone, 2-ethylhexyl 2-(4-phenylbenzoyl)-benzoate, 5-methyl-2-phenylbenzoxazole, sodium 3,4-dimethoxyphenylglyoxylate, 1,3-bis(4-methoxphenyl)propane-1,3-dione, 5-(3,3-dimethyl-2-norbornylidene)-3-penten-2-one, alpha-(2-oxoborn-3-ylidene)-p-xylene-2-sulfonic acid, alpha-(2-oxoborn-3-ylidene)toluene-4-sulfonic acid and its salts, 3-(4-methylbenzylidene)bornan-2-one, 3-benzylidenebornan-2-one, alpha-cyano-4-methoxycinnamic acid and its hexyl ester, 1-p-cumenyl-3-phenylpropane-1,-3-dione, 4-isopropylbenzyl salicylate, cyclohexyl 4-methoxycinnamate, and 1-(4-t-butylphenyl)-3-(4-methoxyphenyl)propane-1,3-dione.

24. A sunscreen composition of any one of embodiments 1-3, wherein a sunscreen active agent is octyl methoxycinnamate at a concentration of about 4.5% to about 15% (w/v).

25. A sunscreen composition of any one of embodiments 1-3, wherein a sunscreen active agent is Octocrylene at a concentration of about 0.5% to about 15% (w/v).

26. A sunscreen composition of any one of embodiments 1-3, wherein a sunscreen active agent is Avobenzone (e.g., PARSOL 1789) at a concentration of about 2% to about 4% (w/v), 27. A sunscreen composition of any one of embodiments 1-3, wherein a sunscreen active agent is titanium dioxide at a concentration of about 3% to about 9% (w/v).

28. A sunscreen composition of any one of embodiments 1-3, wherein the composition contains an active agent at about 0.1 to 7.5 weight percent of octylmethoxy cinnamate, and/or about 0.1 to 6 parts weight percent of octyl salicylate, and/or about 0.1 to 5 parts weight percent of oxybenzone, and/or about 1 to 10 weight percent of cationic surfactant, and/or about 0.01 to 1 weight percent of a quaternized compound.

29. A sunscreen composition of any one of embodiments 1-28, wherein the composition contains a firm former.

30. A sunscreen composition of any one of embodiments 1-30, wherein the composition contains a preservative.

31. A sunscreen composition of embodiment 30, wherein the preservative is at a concentration of about 0.01% to about 1% (w/v).

32. A sunscreen composition of any one of embodiments 1-32, wherein the SPF protection provided by a sunscreen active agent in the composition is from about 1 to 70.

33. A sunscreen composition of any one of embodiments 1-32, wherein the SPF protection provided by a sunscreen active agent in the composition is from about 1 to about 50, or about 2 to about 50, or about 2 to about 40, or about 2 to about 30, or about 2 to about 20, or about 2 to about 10, or about 2 to about 5, or about 5 to about 25, or about 5 to about 20, or about 5 to about 15, or about 5 to about 10.

34. A sunscreen composition of any one of embodiments 1-32, wherein the SPF protection provided by a sunscreen composition in the composition is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more.

35. A sunscreen composition of any one of embodiments 1-32, wherein the SPF protection provided by a sunscreen composition in the composition remains above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more 36. A sunscreen composition of any one of embodiments 1-32, wherein the SPF protection provided by the composition lasts at least about 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 hours or more.

37. A sunscreen composition of any one of embodiments 1-36, wherein the SPF protection provided by the composition lasts for an average of at least about about 1 day, 2 days, 3 days, 4 days, 5 days, 6 days, 7 days, 8 days, 9 days, 10 days, 11 days, 12 days, 13 days, 14 days, after rinsing.

38. A sunscreen composition of any one of embodiments 1-37, wherein the SPF protection provided by the composition increases after each additional application.

39. A sunscreen composition of embodiment 38, wherein the SPF protection provided by the composition increases after each additional application so that after a second, third, fourth, fifth, sixth, seventh, eighth, ninth, tenth, eleventh or more washes, the SPF provided can be above about 1, 2, 3, 4, 5, 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more.

40. A sunscreen composition of any one of embodiments 1-40, wherein the composition includes a cationic polymer.

41. A sunscreen composition of embodiment 40, wherein the cationic polymer is a quaternium or a polyquaternium.

42. A sunscreen composition of embodiment 29, wherein the film former is dimethicone and/or petrolatum.

43. A sunscreen composition of embodiment 30, wherein the preservative is BHT.

44. A sunscreen composition of any one of embodiments 1-43, wherein the additional agent is an antioxidant, a chelating agent, a liquid hydrocarbon, a foaming agent, a skin nourishing substance, sunless tanning actives, skin lightening actives, anti-acne actives, anti-skin wrinkling and anti-skin aging actives, vitamins, anti-inflammatory actives, anesthetic actives, analgesic actives, anti-pruritic actives, anti-microbial actives (e.g. antifungals, antibacterials, and antiparasitics), anti-virals, anti-allergenics, medicinal actives (e.g., skin rash, skin disease and dermatitis medications), anti-cellulite additives, insect repellant actives, antioxidants, hair growth promoters, hair growth inhibitors, hair bleaching agents, vitamins, deodorant compounds, dihydroxyacetone (DHA); glyceryl aldehyde; tyrosine and tyrosine derivatives such as malyltyrosine, tyrosine glucosinate, and ethyl tyrosine; phospho-DOPA, indoles and derivatives, skin lightening actives include, without limitation, EMBLICA (also an antioxidant), monobenzone (a depigmenting agent), kojic acid, arbutin, ascorbic acid and derivatives thereof (e.g., magnesium ascorbyl phosphate or sodium ascorbyl phosphate), and extracts (e.g., mulberry extract, placental extract).

45. A sunscreen composition of any one of embodiments 1-44, wherein the composition is applied topically.

46. A sunscreen composition of embodiment 45, wherein the composition is sprayed.

47. A sunscreen composition of any one of embodiments 1-46, wherein an additional agent is a surfactant.

48. A sunscreen composition of embodiment 47, wherein the surfactant is cationic, anionic, nonionic, zwitterionic, amphoteric, or any combination thereof.

49. A sunscreen composition of any one of embodiments 1-48, wherein a sunscreen active agent is organic or inorganic.

50. A sunscreen composition of any one of embodiments 1-49, wherein the sunscreen composition includes an additional agent to treat a condition suffered by an individual.

51. A sunscreen composition of embodiment 50, wherein the composition is used to treat Seborrheic dermatitis, eczema, xerosis, infestation, dyschromia, keratosis pilaris, acne, anti-aging, sensitive skin, ephilidies, solar lentigines, photo sensitive disease, skin cancer and hx of skin cancer, melisma, auto immune, alopecia, fungal, bacterial, and viral infections, protect colored or treated hair, bromhidrosis, malodor, dandruff, wound healing, insect repellant, pet shampoo/skin care, lindane or similar conditions.

52. A sunscreen composition of any one of embodiments 1-3, wherein a sunscreen active agent is titanium dioxide.

53. A sunscreen composition of embodiment 52, wherein the titanium dioxide has an anatase, ritile or amorphous structure.

54. A sunscreen composition of embodiment 52, wherein the titanium dioxide is uncoated or coated.

55. A sunscreen composition of embodiment 54, wherein the titanium dioxide is coated with aluminum compounds.

56. A sunscreen composition of embodiment 55, wherein the titanium dioxide is coated with aluminum oxide, aluminum stearate or aluminum laurate.

57. A sunscreen composition of embodiment 54, wherein the titanium dioxide is coated with phospholipids or silicone compounds.

58. A sunscreen composition of embodiment 52, wherein the titanium dioxide is micronized and has a mean primary particle size ranging from about 10 nm to about 50 nm.

59. A sunscreen composition of embodiment 52, wherein the titanium dioxide has a micronized mean primary particle size of 15 nm.

60. A sunscreen composition of embodiment 52, wherein the titanium dioxide is uncoated.

61. A sunscreen composition of embodiment 60, wherein the uncoated titanium dioxide has a mean particle size of around 35 nm to about 50 nm.

62. A sunscreen composition of embodiment 52, wherein the composition comprises a mixture of two or more different particle sizes of titanium dioxide.

63. A sunscreen composition of embodiment 52, wherein the composition comprises a mixture of coated and uncoated titanium dioxide.

64. A sunscreen composition of any one of embodiments 1-63, wherein the composition comprises a sunscreen active agent is encapsulated.

65. A sunscreen composition of any one of embodiments 1-63, wherein the composition comprises two or more sunscreen active agents are encapsulated.

66. A sunscreen composition of any one of embodiments 1-65, wherein the composition comprises one or more sunscreen active agents, each comprising at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more of the sunscreen composition (w/v).

67. A sunscreen composition of any one of embodiments 1-65, wherein the composition comprises one or more sunscreen active agents, each comprising at least about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more of the sunscreen composition (w/v).

68. A sunscreen composition of any one of embodiments 1-68, wherein the composition absorbs at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of incident radiation at wave lengths of 290 to 320 nanometers, 69. A sunscreen composition of any one of embodiments 1-68, wherein the composition absorbs at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of incident radiation at wave lengths less than 290 or greater than 320 nanometers.

70. A sunscreen composition of any one of embodiments 1-69, wherein the ratio of sunscreen composition to bodywash, shampoo, conditioner, lotion, gel, soap, cream, hand sanitizer, spray or mousse is about 0.2, 0.5, 0.7 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10; 12, 15, or 20 parts bodywash, shampoo, lotion, conditioner, gel, soap, hand sanitizer, cream, spray or mousse to sunscreen active agent as measured w/w.

71. A sunscreen composition of any one of embodiments 1-70, wherein the pH of the composition is from about 6 to about 8.

72. A sunscreen composition of any one of embodiments 1-70, wherein the pH of the composition is from about 6.7 to about 7.5. pH to 4.0 to about 10.

73. A sunscreen composition of any one of embodiments 1-70, wherein the pH of the composition is at least 1, 2, 3, 4, 5, 6, 7, 8, 9, 10, 11, 12, 13, or 14.

74. A sunscreen composition according to any one of embodiments 1-73, wherein a cellulose derived capsule contains one sunscreen active agent.

75. A sunscreen composition according to any one of embodiments 1-73, wherein a cellulose derived capsule contains two or more sunscreen active agents.

76. A sunscreen composition according to any one of embodiments 1-73, wherein the cellulose derived capsule is flexible.

77. A sunscreen composition according to any one of embodiments 1-73, wherein the cellulose derived capsule has a high load rate.

78. A sunscreen composition according to any one of embodiments 1-77, wherein the cellulose derived capsule is comprised of hydroxypropylcellulose, hydroxypropylmethylcellulose, ethylcellulose, carboxymethylcellulose or any derivatives therefrom.

79. A sunscreen composition according to any one of embodiments 1-78, wherein the cellulose derived capsule has a diameter of about 400 nm to about 700 nm. In an additional embodiment, a cellulose derived capsule has a diameter of about 400 nm to about 650 nm, about 400 nm to about 600 nm, about 400 nm to about 550 nm, about 400 nm to about 500 nm, about 400 nm to about 450 nm. In a further embodiment, a cellulose derived capsule has a diameter of at least 25 nm, at least 50 nm, at least 75 nm, at least 100 nm, at least 125 nm, at least 150 nm, at least 175 nm, at least 200 nm, at least 225 nm, at least 250 nm, at least 275 nm, at least 300 nm, at least 325 nm, at least 350 nm, at least 375 nm, at least 400 nm, at least 425 nm, at least 450 nm, at least 475 nm, at least 500 nm, at least 525 nm, at least 550 nm, at least 575 nm, at least 600 nm, at least 625 nm, at least 650 nm, at least 675 nm, at least 700 nm, at least 725 nm, at least 750 nm, at least 775 nm, at least 800 nm, at least 825 nm, at least 850 nm, at least 875 nm, at least 900 nm, at least 925 nm, at least 950 nm, at least 975 nm, at least 1000 nm or more.

80. A sunscreen composition of any one of embodiments 1-79, wherein the composition comprises water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients.

81. A sunscreen composition of any one of embodiments 1-80, wherein the composition includes, without limitation, at least two, three, four, five, six, seven, eight, nine, ten, or more additional agents.

82. A sunscreen composition of embodiment 81, wherein the additional agents have a concentration that is from about 0.0001% to about 99.9% (w/v).

83. A sunscreen composition of any one of embodiments 1-82, wherein one or more additional agents are encapsulated.

84. A sunscreen composition of any one of embodiments 1-82, wherein one or more additional agents are encapsulated and one or more additional agents are not encapsulated.

85. A sunscreen composition of any one of embodiments 1-82, wherein one or more additional agents are not encapsulated.

86. A sunscreen composition of any one of embodiments 1-85, wherein the composition increases the protection of an individual to which the composition is applied by at least 0.1 times greater, 0.2 times greater, 0.3 times greater, 0.4 times greater, 0.5 times greater, 0.6 times greater, 0.7 times greater, 0.8 times greater, 0.9 times greater, 1 times greater, 1.25 times greater, 1.5 times greater, 1.75 times greater, 2 times greater, 2.25 times greater, 2.5 times greater, 2.75 times greater, 3 times greater, 3.25 times greater, 3.5 times greater, 3.75 times greater, 4 times greater, 4.25 times greater, 4.5 times greater, 4.75 times greater, 5 times greater, 5.25 times greater, 5.5 times greater, 5.75 times greater, 6 times greater, 6.25 times greater, 6.5 times greater, 6.75 times greater, 7 times greater, 7.25 times greater, 7.5 times greater, 7.75 times greater, 8 times greater, 8.25 times greater, 8.5 times greater, 8.75 times greater, 9 times greater, 9.25 times greater, 9.5 times greater, 9.75 times greater, 10 times greater, 11 times greater, 12 times greater, 13 times greater, 14 times greater, 15 times greater, 16 times greater, 17 times greater, 18 times greater, 19 times greater, 20 times greater, 21 times greater, 22 times greater, 23 times greater, 24 times greater, 25 times greater, 30 times greater, 35 times greater, 40 times greater, 45 times greater, 50 times greater, 55 times greater, 60 times greater, 65 times greater, 70 times greater, 75 times greater, 80 times greater, 85 times greater, 90 times greater, 95 times greater, 100 times greater than a sunscreen active agent is not encapsulated 87. A sunscreen composition of any one of embodiments 1-86, wherein the concentration of a sunscreen active agent that is a UVA absorber is from of about 1% to about 40%, or about 2% to about 20%, or about 2% to about 10%, or about 5% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% (w/v).

88. A sunscreen composition of any one of embodiments 1-86, wherein the concentration of a sunscreen active agent that is a UVB absorber is from of about 1% to about 40%, or about 2% to about 20%, or about 2% to about 10%, or about 5% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% (w/v).

89. A sunscreen composition of any one of embodiments 1-86, wherein the concentration of a sunscreen active agent is from of about 1% to about 40%, or about 2% to about 20%, or about 2% to about 10%, or about 5% to about 10%, or about 1%, 2%, 3%, 4%, 5%, 6%, 7%, 7.4%, 7.5%, 7.6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% (w/v).

90. A sunscreen composition of any one of embodiments 1-89, wherein the cellulose derived capsule is prepared so as to experience breakage in the range of about 0, 0.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95% to about 0.50.1, 0.5, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or 95% after application.

91. A sunscreen composition of any one of embodiments 1-89, wherein the cellulose derived capsule is prepared so as to experience breakage in response to conditions that occur on the skin or hair.

92. A sunscreen composition of any one of embodiments 1-89, wherein the cellulose derived capsule is prepared so as to experience breakage in response to conditions that occur on the skin or hair in a time release or controlled manner.

93. A sunscreen composition of any one of embodiments 1-92, wherein the additional agent is a vitamin.

94. A sunscreen composition of embodiment 93, wherein the vitamin is selected from Vitamin A and derivatives thereof (including, for example, retinol, see anti-wrinkling actives), ascorbic acid (Vitamin C and derivatives), Vitamin B (e.g., riboflavin, vitamin $B_2$), biotin, Vitamin D (all forms), Vitamin E and derivatives thereof such as tocopheryl acetate, beta-carotene, panthothenic acid, vitamin C, vitamin E and coenzyme Q-10 more.

95. A sunscreen composition of embodiment 93, wherein the vitamin is encapsulated in a cellulose derived capsule.

96. A sunscreen composition of embodiment 93, wherein the vitamin is not encapsulated in a cellulose derived capsule.

97. A sunscreen composition of any one of embodiments 1-92, wherein the additional agent is an anti-acne active.

98. A sunscreen composition of embodiment 97, wherein the anti-acne active is selected from benzoyl peroxide, erythromycin, clindamycin phosphate, 5,7-dichloro-8-hydroxyquinoline, resorcinol, resorcinol acetate, salicylic acid, azaleic acid, long chain dicarboxylic acids, sulfur, zinc, various natural agents such as those derived from green tree, and more.

99. A sunscreen composition of embodiment 97, wherein the anti-acne active is encapsulated in a cellulose derived capsule.

100. A sunscreen composition of embodiment 97, wherein the anti-acne active is not encapsulated in a cellulose derived capsule.

101. A sunscreen composition of any one of embodiments 1-92, wherein the additional agent is an anti-skin wrinkling active.

102. A sunscreen composition of embodiment 101, wherein the anti-skin wrinkling active is selected from cosmetic products that contain hydroxy acids, retinol, retinoic, retinol palmitate, a derivative of vitamin A, (or its stronger, prescribed version Retin-A and Renova), bicyclic aromatic compounds with retinoid-type activity and more.

103. A sunscreen composition of embodiment 101 wherein the anti-skin wrinkling active is encapsulated in a cellulose derived capsule.

104. A sunscreen composition of embodiment 101 wherein the anti-skin wrinkling active is not encapsulated in a cellulose derived capsule.

105. A sunscreen composition of any one of embodiments 1-92, wherein the additional agent is a botulinium toxin serotype A.

106. A sunscreen composition of embodiment 105, wherein an anti-skin aging or anti-wrinkling additional agents are bicyclic aromatic compounds, compounds which have retinoid-type activity, free-radical scavengers, hydroxy or keto acids or derivatives thereof.
107. A sunscreen composition of embodiment 106, wherein the free-radical scavengers are selected from α-tocopherol, superoxide dismutase, ubiquinol or certain metal-chelating agents.
108. A sunscreen composition of embodiment 106, wherein hydroxyl acids are selected from α-hydroxy acids such as lactic acid and glycolic acid or β-hydroxy acids such as salicylic acid and salicylic acid derivatives such as the octanoyl derivative; other hydroxy acids and keto acids include, without limitation, malic, citric, mandelic, tartaric or glyceric acids or the salts, amides or esters thereof.
109. A sunscreen composition of any one of embodiments 1-104, wherein an anti-skin aging or anti-wrinkling additional agents are sulfur-containing D and L amino acids and their derivatives and salts, phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof.
110. A sunscreen composition of any one of embodiments 1-92, wherein the additional agent is an anti-inflammatory active.
111. A sunscreen composition of embodiment 110, wherein the anti-inflammatory active is selected from corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

112. A sunscreen composition of embodiment 110, wherein the anti-inflammatory active is selected from nonsteroidal anti-inflammatory agents include, without limitation, oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof, COX-2 inhibitors including AZD 3582 (Astrazeneca and NicOx), Celecoxib (Pharmacia Corp.) (4-[5-(4-methyl-phenyl)-3-(trifluoromethyl)-1H-pyrazol-1-yl] benzenesulfonamide), Meloxicam (Boehringer Ingelheim Pharmaceuticals) (4-hydroxy-2-methyl-N-(5-methyl-2-thiazolyl)-2H-1,2GW-406381 (Glaxosmithkline), Etoricoxib (MERCK & Co.), Rofecoxib (MERCK & Co.) (4-[4-(methylsulfonyl) phenyl]-3-phenyl-2(5H)-furanone), Lumiracoxib (Novartis Pharma AG), Valdecoxib (Pharmacia Corp.) (4-(5-methyl-3-phenyl-4-isox-azolyl) benzenesulfonamide), and Etodolac (Wyeth Ayerst Laboratories) ((±) 1,8-diethyl-1,3,4,9-tetrahydropyrano-[3,4-b]acid).

113. A sunscreen composition of embodiment 110, wherein the anti-inflammatory active is encapsulated in a cellulose derived capsule.

114. A sunscreen composition of embodiment 110, wherein the anti-inflammatory active is not encapsulated in a cellulose derived capsule.

115. A sunscreen composition of embodiment 114, wherein an additional agent is selected from candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

116. A sunscreen composition of any one of embodiments 1-92, wherein the additional agent is an anesthetic.

117. A sunscreen composition of embodiment 116, wherein the anesthetic is selected from butamben picrate, lidocaine, xylocalne, benzocaine, bupivacaine, chloroprocaine, dibucaine, etidocaine, mepivacaine, tetracaine, dyclonine, hexylcaine, procaine, cocaine, ketamine, pramoxine, phenol, and pharmaceutically acceptable salts thereof.

118. A sunscreen composition of embodiment 116, wherein the anesthetic is encapsulated in a cellulose derived capsule.

119. A sunscreen composition of embodiment 116, wherein the anesthetic is not encapsulated in a cellulose derived capsule.

120. A sunscreen composition of any one of embodiments 1-92, wherein the additional agent is an analgesic.

121. A sunscreen composition of embodiment 120, wherein the analgesic is selected from dyclonine hydrochloride, aloe vera, fentanyl, capsaicin, and the like. In an embodiment, anti-pruritic actives include, without limitation, alclometasone dipropionate, betamethasone valerate, and isopropyl myristate MSD. In an embodiment, anti-microbial actives include, without limitation, antifungal, antibacterial, and antiseptic compounds. Antifungal compounds include, but are not limited to, compounds such as imidazole antifungals. Specific antifungals include butocouazole nitrate, miconazole, econazole, ketoconazole, oxiconizole, haloprogin, clotrimazole, and butenafine HCl, naftifine, terbinafine, ciclopirox, and tolnaftate. Antibacterial and antiseptic compounds include phenol-TEA complex, mupirocin, triclosan, chlorocresol, chlorbutol, iodine, clindamycin, CAE (Anjinomoto Co., Inc., containing DL-pyrrolidone Carboxylic acid salt of L-Cocoyl Arginine Ethyl Ester), povidone-iodine, polymyxin b sulfate-bacitracin, zinc-neomycin sulfate-hydrocortisone, chloramphenicol, methylbenzethonium chloride, and erythromycin and antiseptics (e.g., benzalkonium chloride, benzethonium chloride, chlorhexidine gluconate, mafenide acetate, nitrofurazone, nitromersol, antimicrobial deodorant compounds, antiparasitics, and lindane.

122. A sunscreen composition of embodiment 120, wherein the analgesic is encapsulated in a cellulose derived capsule.

123. A sunscreen composition of embodiment 120, wherein the analgesic is not encapsulated in a cellulose derived capsule.

124. A sunscreen composition of any one of embodiments 1-92, wherein the additional agent is an antimicrobial and antifungal.

125. A sunscreen composition of embodiment 124, wherein the antimicrobial and antifungal is selected from beta.-lactam drugs, quinolone drugs, ciprofloxacin, norfloxacin, tetracycline, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.
126. A sunscreen composition of embodiment 124, wherein the antimicrobial and antifungal is encapsulated in a cellulose derived capsule.
127. A sunscreen composition of embodiment 124, wherein the antimicrobial and antifungal is not encapsulated in a cellulose derived capsule.
128. A sunscreen composition of any one of embodiments 1-92, wherein the additional agent is an anti-viral.
129. A sunscreen composition of embodiment 128, wherein the anti-viral is selected from limitatin, metal salts, silver nitrate, copper sulfate, iron chloride, organic acids, malic acid, salicylic acid, succinic acid and benzoic acid.
130. A sunscreen composition of embodiment 128, wherein the anti-viral is encapsulated in a cellulose derived capsule.
131. A sunscreen composition of embodiment 129, wherein the anti-viral is not encapsulated in a cellulose derived capsule.
132. A sunscreen composition of any one of embodiments 1-92, wherein the additional agent is an anti-allergenics.
133. A sunscreen composition of embodiment 132, wherein the anti-allergenics is an antihistamine.
134. A sunscreen composition of embodiment 132, wherein the antihistamine is selected from diphenhydramine (Benadryl), chlorpheniramine, tripelennamine, promethazine, clemastine, doxylamine, benadryl and more. In a further embodiment, $H_1$-non-sedating antihistamines include, without limitation, astemizole, terfenadine, loratadine, cimetadine, cromolyn, famotidine, nizatidine, and ranitidine.
135. A sunscreen composition of embodiment 132, wherein the anti-allergenics is encapsulated in a cellulose derived capsule.
136. A sunscreen composition of embodiment 132, wherein the anti-allergenics is not encapsulated in a cellulose derived capsule.
137. A sunscreen composition of any one of embodiments 1-92, wherein the additional agent treats dermatological conditions.
138. A sunscreen composition of embodiment 137, wherein the dermatological condition is selected from psoriasis, acne, eczema, and other skin conditions due to disease, pathology, accident, and the like.
139. A sunscreen composition of embodiment 137, wherein the treatment of a dermatological condition is selected from o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; herpes treatment drugs, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as 2-(acetyloxy)-9-fluoro-1',2',3',4'-tetrahydro-11-hydroxypregna-1,4-dieno [16,17-b]naphthalene-3,20-dione and 21-chloro-9-fluoro-1',2',3',4'-tetrahydro-11 b-hydroxypregna-1,4-dieno[16z, 17-b]naphthalene-3,20-dione, camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, or hydrocortisone acetate.
140. A sunscreen composition of embodiment 137, wherein the dermatological condition is encapsulated in a cellulose derived capsule.
141. A sunscreen composition of embodiment 137, wherein the dermatological condition is not encapsulated in a cellulose derived capsule.
142. A sunscreen composition of any one of embodiments 1-92, wherein the additional agent is an anticellulite active.
143. A sunscreen composition of embodiment 142, wherein the anticellulite active is selected from isobutylmethylxanthine, caffeine, theophylline, theobromine, aminophylline, yohimbine, and mixtures thereof.
144. A sunscreen composition of embodiment 142, wherein the anti-allergenics is encapsulated in a cellulose derived capsule.
145. A sunscreen composition of embodiment 142, wherein the anti-allergenics is not encapsulated in a cellulose derived capsule.
146. A sunscreen composition of any one of embodiments 1-92, wherein the additional agent treats hair loss.
147. A sunscreen composition of embodiment 146, wherein the hair loss treatment active is selected from potassium channel openers or peripheral vasodilators such as minoxidil, diazoxide, and compounds such as N*-cyano-N-(tert-pentyl)-N'-3-pyridinyl-guanidine; vitamins, such as vitamin E and vitamin C, and derivatives thereof such as vitamin E acetate and vitamin C palmitate; hormones, such as erythropoietin, prostaglandins, such as prostaglandin El and prostaglandin F2-alpha; fatty acids, such as oleic acid; diuretics such as spironolactone; heat shock proteins ("HSP"), HSP 27,d HSP 72; calcium channel blockers, such as verapamil HCL, nifedipine, and diltiazemamiloride; cyclosporin and Fk-506; 5 alpha-reductase inhibitors such as finasteride; EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, *ginseng*, rehmannia, swertia, sweet orange, zanthoxylum, Serenoa *repens* (saw palmetto), Hypoxis rooperi, stinging nettle, pumpkin seeds, and rye pollen; other botanical extracts including sandlewood, red beet root, *chrysanthemum*, rosemary, burdock root, Kalium Phosphoricum D2, Azadirachta indica D2, and Joborandi DI; ketoconazole and elubiol;

streptomycin; cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin: quercetin, isoquercitrin, hespeddin, naringin, and methylhesperidin, and flavonoids and transglycosidated derivatives, minoxidil, piperdinyl)-2,4-pyrimidinediamine-3-oxide, N'-cyano-N-(tert-pentyl)-N'-3-pyridinylguanidine, finasteride, retinoids and derivatives thereof, ketoconazole, elubiol, trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, alpha-tocophenol or mixtures thereof.

148. A sunscreen composition of embodiment 146, wherein the hair growth stimulant is encapsulated in a cellulose derived capsule.

149. A sunscreen composition of embodiment 146, wherein the hair growth stimulant is not encapsulated in a cellulose derived capsule.

150. A sunscreen composition of any one of embodiments 1-92, wherein the additional agent is a hair bleaching agent.

151. A sunscreen composition of embodiment 150, wherein the hair bleaching agent is selected from perborate or persulfate salts.

152. A sunscreen composition of embodiment 150, wherein the hair bleaching agent is encapsulated in a cellulose derived capsule.

153. A sunscreen composition of embodiment 150, wherein the hair bleaching agent is not encapsulated in a cellulose derived capsule.

154. A sunscreen composition of any one of embodiments 1-92, wherein the additional agent is a deodorant.

155. A sunscreen composition of embodiment 154, wherein the deodorant is selected from astringent salts and bioactive compounds.

156. A sunscreen composition of embodiment 155, wherein the astringent salts are selected from organic and inorganic salts of aluminum, zirconium, zinc, sulfate, chloride, chlorohydroxide, alum, formate, lactate, benzyl sulfonate or phenyl sulfonate, aluminum chloride, aluminum halides, aluminum hydroxyhalides, zirconyl oxyhalides, zirconyl hydroxyhalides, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, chlorophyllin copper complex, aluminum chloride, aluminum chloride hexahydrate, and methylbenzethonium and mixtures thereof 157. A sunscreen composition of embodiment 154, wherein the deodorant is a bacteriostatic quaternary aluminum compound.

158. A sunscreen composition of embodiment 156, wherein the aluminum compound is selected from cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; alkali metal carbonates and bicarbonates, and ammonium and tetralkylammonium carbonates and bicarbonates.

159. A sunscreen composition of embodiment 154, wherein the deodorant is encapsulated in a cellulose derived capsule.

160. A sunscreen composition of embodiment 154, wherein the deodorant agent is not encapsulated in a cellulose derived capsule.

161. A sunscreen composition of any one of embodiments 1-92, wherein the additional agent is an antioxidant.

162. A sunscreen composition of embodiment 161, wherein the antioxidants is selected from propyl, octyl and dodecyl esters of gallic acid, butylated hydroxyanisole, butylated hydroxytoluene (BHT), nordihydroguaiaretic acid, Vitamin A, ascorbic acid and its salts, ascorbyl esters of fatty acids, ascorbic acid derivatives, magnesium ascorbyl phosphate, sodium ascorbyl phosphate, ascorbyl sorbate, tocopherol, tocopherol acetate, other esters of tocopherol, tocotrienols and their esters, 6-hydroxy-2,5,7,8-tetramethylchroman-2-carboxylic acid, uric acid and its salts and alkyl esters, sorbic acid and its salts, lipoic acid, amines, N,N-diethylhydroxylamine, amino-guanidine, sulfhydryl compounds, glutathione, N-acetyl cysteine, dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

163. A sunscreen composition of embodiment 161, wherein the antioxidants is encapsulated in a cellulose derived capsule.

164. A sunscreen composition of embodiment 161, wherein the antioxidants is not encapsulated in a cellulose derived capsule.

165. A sunscreen composition of any one of embodiments 1-92, wherein the additional agent is a photostable antioxidant.

166. A sunscreen composition of embodiment 165, wherein the photostable antioxidant is encapsulated in a cellulose derived capsule.

167. A sunscreen composition of embodiment 165, wherein the photostable antioxidant is not encapsulated in a cellulose derived capsule.

168. A sunscreen composition of any one of embodiments 1-92, wherein the additional agent is an insect repellent.

169. A sunscreen composition of embodiment 168, wherein the insect repellent is selected from N,N-Diethyl-m-toluamide, dimethyl phthalate, ethyl hexanediol, indalone, citronella oil, lemon grass oil, limonene, rosemary oil and *eucalyptus* oil, di-n-propylisocinchoronat-e, bicycloheptene, dicarboximide and tetrahydrofuraldehyde.

170. A sunscreen composition of embodiment 168, wherein the insect repellent is encapsulated in a cellulose derived capsule.

171. A sunscreen composition of embodiment 168, wherein the insect repellent is not encapsulated in a cellulose derived capsule.

172. A sunscreen composition of embodiment 41, wherein a polyquaternium is polyquaternium-4, -7, -11, -22, -37, -44, -5, and -64.

173. A sunscreen composition of any one of embodiments 1-92, wherein the additional agent is a cationic agent.

174. A sunscreen composition of embodiment 173, wherein the cationic agent is comprises about 0.1 to about 20%, or about 0.1 to about 10%, or about 0.5 to about 10%, or about 1 to about 10%, or about 0.5 to about 5%, or about 0.5 to about 3% or about 1 to about 5%, or about 1 to about 3% of the sunscreen composition (w/v).

175. A sunscreen composition of embodiment 173, wherein the cationic agent comprises about about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more of the sunscreen composition (w/v).

176. A sunscreen composition of any of embodiments 1-2, wherein the additional agent is a film barrier system.

177. A sunscreen composition of embodiment 176, wherein the film barrier system is selected from petrolatum, silicon derivatives and polymers with carboxylic ends.

178. A sunscreen composition of embodiment 176, wherein the film barrier system is encapsulated in a cellulose derived capsule.

179. A sunscreen composition of embodiment 176, wherein the film barrier system is not encapsulated in a cellulose derived capsule.

180. A sunscreen composition of any one of embodiments 1-92, wherein the additional agent is a film former.

181. A sunscreen composition of embodiment 180, wherein the film former is selected from emollient esters, lanolin derivatives, acetylated lanolins, dimethicone, stearamidopropyl dimethylamine stearate tocopheryl acetate, superfatted oils, synthetic wax, acacia gum, cellulose derivatives, guar derivatives acrylamides copolymer, acrylamide/sodium aciylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic anhydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenean, calcium/sodium PVM/MA copolymer, carboxymethyl hydroxyethyl cellulose, cellulose gum, collodion, copal, corn starch/aciylainide/sodium acrylate copolymer, damar, diethylene glycolamine/epichlorohydrin/piperazine copolymer, DMJ-IF, dodecanedoic acid/cetearyl alcoholglycol copolymer, ethylcellulose, ethylene/acrylate copolymer, ethylene/maleic anhydride copolymer, ethylene/vinyl acetate copolymer, ethyl ester of PVM/fvIA copolymer, flexible collodian, gum benzoin, gutta percha, hydroxybutyl methylcellulose, hydroxyethylcellulose, hydroxyethyl ethyl cellulose, hydroxypropylceilulose, hydroxypropyl guar, hydroxypropyl methylcellulose, isopropyl ester of PVM/MA copolymer, maltodextrin, melamine/formaldehyde resin, methacryloyl ethyl betainelmethacrylates copolymer, nitrocellulose, octylacrylamide/acrylates/butylaminoethylmethaciylate copolymer, octylacrylamide/acrylates copolymer, phthalic anhydride/glycerin/gycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methaciylate copolymer, sucrose benzoate/sucrose acetate isobutyrate copolymer, toluenesulfonamide/formaldehyde resin, tragacath gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, zein.

182. A sunscreen composition of embodiment 180, wherein the film former is a liquid acrylic copolymer.

183. A sunscreen composition of embodiment 182, wherein a sunscreen composition includes a liquid acrylic copolymer at a concentration of about 0.05%, 0.1%, 0.2%, 0.3%, 0.4%, or 0.5% or about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10% or more.

184. A sunscreen composition of embodiment 180, wherein the film former is encapsulated in a cellulose derived capsule.
185. A sunscreen composition of embodiment 180, wherein the film former is not encapsulated in a cellulose derived capsule.
186. A sunscreen composition of any one of embodiments 1-92, wherein the additional agent is a secondary film former.
187. A sunscreen composition of embodiment 186, wherein the secondary film former is selected from keratin or other protein derivative in an amino acid complex such as cysteine.
188. A sunscreen composition of embodiment 187, wherein a sunscreen composition includes a secondary film former at a concentration of about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more.
189. A sunscreen composition of embodiment 186, wherein the secondary film former is encapsulated in a cellulose derived capsule.
190. A sunscreen composition of embodiment 186, wherein the secondary film former is not encapsulated in a cellulose derived capsule.
191. A sunscreen composition of any one of embodiments 1-92, wherein the additional agent is a preservative.
192. A sunscreen composition of embodiment 191, wherein the preservative is selected from citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines, imidiazolinylurea, triclosan, hydantoins, dimethyloldimethylhydantoin, isothiazolidinone compounds and mixtures thereof, methylchloroisothiazolinone and methylisothiazolinone.
193. A sunscreen composition of embodiment 191, wherein the concentration of preservative in a sunscreen composition is about about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more (w/v).
194. A sunscreen composition of embodiment 191, wherein the preservative is encapsulated in a cellulose derived capsule.
195. A sunscreen composition of embodiment 191, wherein the preservative is not encapsulated in a cellulose derived capsule.
196. A sunscreen composition of any one of embodiments 1-92, wherein the additional agent is a chelating agent.
197. A sunscreen composition of embodiment 196, wherein the chelating agent is selected from heterocyclic ring structures, ethylene diaminetetraacetic acid (EDTA), EDTA disodium, calcium disodium edetate, EDTA trisodium, EDTA tetrasodium and EDTA dipotassium.
198. A sunscreen composition of embodiment 196, wherein the concentration of chelating agent in a sunscreen composition is about about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more (w/v).
199. A sunscreen composition of embodiment 196, wherein the chelating agent is encapsulated in a cellulose derived capsule.
200. A sunscreen composition of embodiment 196, wherein the chelating agent is not encapsulated in a cellulose derived capsule.
201. A sunscreen composition of any one of embodiments 1-92, wherein the additional agent is a thickening agent or gellant.
202. A sunscreen composition of embodiment 201, wherein the thickening agent or gellant system is selected from CARBOPOL™ resins [e.g., 934, 971, 974, 980, 981] and PEMULEN™ [TR-1 and TR-2] [both CARBOPOL™ and PEMULEN™ are registered trademarks of BF Goodrich], Noveon AA-1, ETD resins, and ULTREZ™ resins [registered trademark, BF Goodrich] or carbomers.
203. A sunscreen composition of embodiment 201, wherein the thickening agent or gellant is encapsulated in a cellulose derived capsule.
204. A sunscreen composition of embodiment 201, wherein the thickening agent or gellant is not encapsulated in a cellulose derived capsule.
205. A sunscreen composition of any one of embodiments 1-92, wherein the additional agent is a fragrance, dye or antimicrobial material.
206. A sunscreen composition of embodiment 205, wherein the antimicrobial material is selected from triclocarban, triclosan, iodophors, iodine formulations, phenolic compounds, e.g. hexachlorophene, and bisbiguanides, e.g. chlorhexidene gluconate.
207. A sunscreen composition of embodiment 205, wherein fragrance, dye or antimicrobial material is encapsulated in a cellulose derived capsule.
208. A sunscreen composition of embodiment 205, wherein the fragrance, dye or antimicrobial material is not encapsulated in a cellulose derived capsule.
209. A sunscreen composition of any one of embodiments 1-208, wherein the composition is mixed together in a water or an oil.
210. A sunscreen composition of any one of embodiments 1-92, wherein the additional agent is a surfactant.
211. A sunscreen composition of embodiment 210, wherein the surfactant is selected from cationic, anionic, nonionic, zwitterionic, amphoteric, or any combination of surfactants thereof. In a further embodiment, surfactants include, without limitation, alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, sodium, ammonium, potassium, magnesium, or TEA salts of lauryl or myristyl sulfate or ammonium, sodium, magnesium, or TEA laureth-3 sulfate and combinations thereof.
212. A sunscreen composition of embodiment 201, wherein the concentration of surfactant included in a sunscreen composition is at least 0.01%, at least 0.02%, at least 0.03%, at least 0.04%, at least 0.05%, at least 0.06%, at least 0.07%, at least 0.08%, at least 0.09%, at least 0.1%, at least 0.25%, at least 0.5%, at least 0.75%, at least 1%, at least 1.25%, at least 1.5%, at least 1.75%, at least 2%, at least 2.25%, at least 2.5%, at least 2.75%, at least 3%, at least 3.25%, at least 3.5%, at least 3.75%, at least 4%, at least 4.25%, at least 4.5%, at least 4.75%, at least 5%, at least 5.25%, at least 5.5%, at least 5.75%, at least 6%, at least 6.25%, at least 6.5%, at least 6.75%, at least 7%, at least 7.25%, at least 7.5%, at least 7.75%, at least 8%, at least 8.25%, at least 8.5%, at least 8.75%, at least 9%, at least 9.25%, at least 9.5%, at least 9.75%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25% (w/v).

213. A sunscreen composition of embodiment 210, wherein the concentration of surfactant included in a sunscreen composition is about 0.01% to about 5%.

214. A sunscreen composition of embodiment 210, wherein the concentration of surfactant included in a sunscreen composition is about 3% to about 5%.

215. A sunscreen composition of embodiment 213, wherein the concentration of surfactant results in reduced lathering.

216. A sunscreen composition of embodiment 210, wherein the concentration of surfactant included in a sunscreen composition is about 7.5% to 15%.

217. A sunscreen composition of embodiment 216, wherein the concentration of surfactant results in lathering.

218. A sunscreen composition of embodiment 210, wherein the surfactant is an anionic surfactant.

219. A sunscreen composition of embodiment 218, wherein the anionic surfactant is selected from sulfated monoglycerides of the form $R1CO-O-CH_2-C(OH)H-CH_2-O-SO_3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine, monoethanolamine and sodium cocomonoglyceride sulfate, olefin sulfonates of the form $R1SO_3M$, wherein R1 is a mono-olefin having from about 12 to about 24 carbon atoms, and M is a water-soluble cation such as ammonium, sodium, potassium, magnesium, triethanolamine, diethanolamine and monoethanolamine, sodium C14/C16 alpha olefin sulfonate, linear alkylbenzene sulfonates of the form $R_1-C_6H_4-SO_3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine monoethanolamine and sodium dodecylbenzene sulfonate. In an additional embodiment, anionic surfactants include, without limitation, primary or secondary alkane sulfonates of the form $R1\ SO_3M$, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine, alkane sulfonate, alkali metal or ammonium C 13 C 17 paraffin sulfonates, alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid, acyl isethionates, including, without limitation, acyl isethionates include ammonium cocoyl isethionate, sodium cocoyl isethionate, sodium lauroyl isethionate, alkylglyceryl ether sulfonates of the form $R1\text{-}OCH_2-C(OH)H-CH_2-SO_3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine, sodium cocoglyceryl ether sulfonate, Sulfonated fatty acids of the form $R1\text{-}CH(SO_4)-COOH$ and sulfonated methyl esters of the from $R1\text{-}CH(SO_4)-CO-O-CH_3$, where R1 is a saturated or unsaturated, branched or unbranched alkyl group from about 8 to about 24 carbon atoms, alpha sulphonated coconut fatty acid and lauryl methyl ester; phosphates such as monoalkyl, dialkyl, and trialkylphosphate salts formed by the reaction of phosphorous pentoxide with monohydric branched or unbranched alcohols having from about 8 to about 24 carbon atoms, sodium mono or dilaurylphosphate, ethoxylated monoalkyl phosphates, acyl glutamates corresponding to the formula $R1CO-N(COOH)-CH_2CH_2-CO_2M$ wherein R1 is a saturated or unsaturated, branched or unbranched alkyl or alkenyl group of about 8 to about 24 carbon atoms, and M is a water-soluble cation, sodium lauroyl glutamate and sodium cocoyl glutamate, alkanoyl sarcosinates corresponding to the formula $R1CON(CH_3)-CH_2CH_2-CO_2M$ wherein R1 is a saturated or unsaturated, branched or unbranched alkyl or alkenyl group of about 10 to about 20 carbon atoms, and M is a water-soluble cation, sodium lauroyl sarcosinate, lauroyl sarcosine, sodium cocoyl sarcosinate, and ammonium lauroyl sarcosinate, alkyl ether carboxylates corresponding to the formula $R1\text{-}(OCH_2CH_2)x\text{-}OCH_2-CO_2M$ wherein R1 is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula $R1CO-[O-CH(CH_3)-CO]x\text{-}CO_2M$ wherein R1 is a saturated or unsaturated, branched or unbranched alkyl or alkenyl group of about 8 to about 24 carbon atoms, x is 3, and M is a water-soluble cation, sodium cocoyl lactylate, carboxylates, nonlimiting examples of which include sodium lauroyl carboxylate, sodium cocoyl carboxylate, and ammonium lauroyl carboxylate; anionic flourosurfactants; natural soaps derived from the saponification of vegetable and/or animal fats & oils examples of which include sodium laurate, sodium myristate, palmitate, stearate and tallowate cocoate.

220. A sunscreen composition of embodiment 210, wherein the surfactant is a taurate.

221. A sunscreen composition of embodiment 218, wherein the taurate is selected from taurine, N-alkyltaurines.

222. A sunscreen composition of embodiment 210, wherein the surfactant is a nonionic surfactant.

223. A sunscreen composition of embodiment 218, wherein the nonionic surfactant is selected from alkyl glucosides, alkyl polyglucosides, polyhydroxy fatty acid amides, alkoxylated fatty acid esters, sucrose esters, amine oxides, glycosides or polyglycosides and are represented by the formula $(S)_n-O-R$ wherein S is a sugar moiety such as glucose, fructose, mannose, and galactose; n is an integer of from about 1 to about 1000, and R is a $C_{8\text{-}30}$ alkyl group decyl alcohol, cetyl alcohol, stearyl alcohol, lauryl alcohol, myristyl alcohol, oleyl alcohol, decyl polyglucoside, sucrose cocoate, polyhydroxy fatty acid amide, glucosamides and sucrose laurate.

224. A sunscreen composition of embodiment 210, wherein the surfactant is an ampohoteric lathering surfactant.

225. A sunscreen composition of embodiment 218, wherein the ampoteric lathering surfactant is selected from carboxy, sulfonate, sulfate, phosphate, or phosphonate. In an embodiment, amphoteric or zwitterionic surfactants include, without limitation, betaines, sultaines, hydroxysultaines, alkyliminoacetates, iminodialkanoates, aminoalkanoates, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl, and cocamidopropyl betaine, sultaines, hydroxysultaines and cocamidopropyl hydroxysultaine.

226. A sunscreen composition of embodiment 210, wherein the surfactant is an amphoteric surfactant.

227. A sunscreen composition of embodiment 218, wherein the amphoteric surfactant is selected from taurine, Cetyl dimethyl betaine, Cocamidopropylbetaine; Cocamidopropyl hydroxy sultaine, alkyliminoacetates, and iminodialkanoates and aminoalkanoates of the formulas $RN[(CH_2)CO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, alkanolammonium or imidazolinium and ammonium derivatives, sodium 3-dodecyl-aminopropionate, sodium 3-dodecylaminopropane sulfonate, N-higher alkyl aspartic acids, amphoteric phosphates, such as coamidopropyl PG-dimonium chloride phosphate, disodium lauroamphodiacetate, sodium lauroamphoacetate, and mixtures thereof.

228. A sunscreen composition of embodiment 210, wherein the surfactant is a cationic surfactant.

229. A sunscreen composition of embodiment 218, wherein the cationic surfactant is selected from fatty amines, di-fatty quaternary amines, tri-fatty quaternary amines, imidazolinium quaternary amines, monoalkyl quaternary amines such as cetyltrimethylammonium bromide, dialklamidoethyl hydroxyethylmonium methosulfate stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride and stearalkonium chloride.

230. A sunscreen composition of embodiment 210, wherein the concentration of a cationic surfactant included in a sunscreen composition is about 0.1%, 0.2%, 0.3%, 0.4%, 0.5%, 0.6%, 0.7%, 0.8%, 0.9%, 1% or 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% or more (w/v).

231. A sunscreen composition of embodiment 210, wherein the surfactant is encapsulated in a cellulose derived capsule.

232. A sunscreen composition of embodiment 210, wherein the surfactant is not encapsulated in a cellulose derived capsule.

233. A sunscreen composition of any one of embodiments 1-232, wherein the composition provides an SPF protection that is at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more.

234. A sunscreen composition of any one of embodiments 1-234, wherein the composition is applied two or more times to an individual and the cumulative SPF protection following the two or more applications is at least about at least about 1, 2, 3, 4, 5, 6, 7, 8, 9, 10, 11, 12, 1.3, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more.

235. A sunscreen composition of any one of embodiments 1-234, wherein the composition is applied once per day.

236. A sunscreen composition of any one of embodiments 1-234, wherein the composition is applied two, three, four or more times per day.

237. A sunscreen composition of any one of embodiments 1-234, wherein the composition is applied every other day.

238. A sunscreen composition of any one of embodiments 1-234, wherein the composition is applied about 10, 8, 7, 6, 5, 4, 3, 2 or 1 time per week.

239. A sunscreen composition of any one of embodiments 1-238, wherein the composition is applied to wet skin and/or hair.

240. A sunscreen composition of any one of embodiments 1-238, wherein the composition is applied to dry skin and/or hair.

241. A sunscreen composition of any one of embodiments 1-240, wherein the composition contains one, two or more surface-treated metal oxide pigments that block UV radiation.

242. A sunscreen composition of embodiment 241, wherein the surface-treated metal oxide blocks UV radiation in the wavelength range of from about 290 nm to about 400 nm.

243. A sunscreen composition of embodiment 241, wherein the combined concentration of the one, two or three surface-metal oxide pigments is at least about 0.1%, 0.2%, 0.3%, 0.4%, 0.5%, 0.6%, 0.7%, 0.8%, 0.9%, 1%, 1.25%, 1.5%, 1.75%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%.

244. A sunscreen composition of any one of embodiments 1-243, wherein the cellulose derived capsules containing sunscreen active agents are in the 400-450 nm range.

245. A sunscreen composition of any one of embodiments 1-243, wherein the cellulose derived capsules containing sunscreen active agents are in the 400-500 nm range.

246. A sunscreen composition of any one of embodiments 1-243, wherein the cellulose derived capsules containing sunscreen active agents are in the 400-550 nm range.

247. A sunscreen composition of any one of embodiments 1-243, wherein the cellulose derived capsules containing sunscreen active agents are in the 400-600 nm range.

248. A sunscreen composition of any one of embodiments 1-243, wherein the cellulose derived capsules containing sunscreen active agents are in the 400-650 nm range.

249. A sunscreen composition of any one of embodiments 1-248, wherein the cellulose derived capsules containing active coating on the exterior of the cellulose derived capsule membrane which has absorption properties.

250. A sunscreen composition of any one of embodiments 1-249, wherein the cellulose derived capsules, further wherein, the cellulose derived capsules are of different sizes.

251. A sunscreen composition of any one of embodiments 1-250, wherein the cellulose derived capsule is comprised of 0.1%-5% wt/wt of cellulosic material.

252. A sunscreen composition of any one of embodiments 1-250, wherein the cellulose derived capsule is comprised of 5%-20% wt/wt of cellulosic material.

253. A sunscreen composition of any one of embodiments 1-250, wherein the cellulose derived capsule is comprised of 20%-50% wt/wt of cellulosic material.

254. A sunscreen composition of any one of embodiments 1-250, wherein the cellulose derived capsule is comprised of 50%-70% wt/wt of cellulosic material.

255. A sunscreen composition of any one of embodiments 1-254, wherein the cellulose derived capsule is comprised of two or more layers.

256. A sunscreen composition of embodiment 255, wherein each layer contains a different sunscreen active agent.

257. A sunscreen composition of embodiment 255, wherein each layer contains the same sunscreen active agent.

258. A sunscreen composition of embodiment 255, wherein each layer contains a different sunscreen active agent.

259. A sunscreen composition of embodiment 255, wherein at least one layer contains a different sunscreen active agent than at least one other layer.

260. A sunscreen composition of embodiment 255, wherein at least one layer contains a sunscreen active agent and at least one layer contains an antioxidant.

261. A sunscreen composition of embodiment 255, wherein at least one layer contains a sunscreen active agent and at least one layer contains a vitamin.

262. A sunscreen composition of embodiment 255, wherein at least one layer contains a sunscreen active agent and at least one layer contains an anti-inflammatory.

263. A sunscreen composition of embodiment 255, wherein at least one layer contains a sunscreen active agent and at least one layer contains an astringent.

264. A sunscreen composition of any one of embodiments 1-263, wherein the composition is comprised of a cationic surfactant, a cellulose derived capsule and a polymer.

265. A sunscreen composition of any one of embodiments 1-263, wherein the composition is comprised of an anionic surfactant, cellulose derived encapsulate, and a polymer.

266. A sunscreen composition of any one of embodiments 1-263, wherein the composition is comprised of a non-ionic surfactant, cellulose derived encapsulate, and a polymer.

267. A sunscreen composition of any one of embodiments 1-263, wherein the composition is comprised of an amphoteric surfactant, cellulose derived encapsulate, and a polymer.

268. A sunscreen composition of any one of embodiments 1-263, wherein the composition is comprised of a surfactant containing a quat group, wherein said quat group is capable of absorbing UV radiation.

269. A sunscreen composition of any one of embodiments 1-263, wherein the composition is comprised of a surfactant metal complex to enhance reflective properties.

270. A sunscreen composition of any one of embodiments 1-263, wherein the composition is comprised of more than one surfactant, a cellulose derived capsule and a polymer.

271. A sunscreen composition of any one of embodiments 1-270, wherein the composition is comprised of a cellulose derived capsule comprising ethyl cellulose and a surfactant base containing one or more polymers.

272. A sunscreen composition of any one of embodiments 1-270, wherein the composition is comprised of a cellulose derived capsule comprising carboxymethyl cellulose and a surfactant base containing one or more polymers.

273. A sunscreen composition of any one of embodiments 1-272, wherein the sunscreen active agent is an organic or non-polar highly refractive sunscreen active agent.

274. A sunscreen composition of any one of embodiments 1-273, wherein the sunscreen active agent is an organic sunscreen active agent and wherein, the composition contains inorganic metals.

275. A sunscreen composition of any one of embodiments 1-274, wherein the sunscreen composition comprises a surfactant, apolymer and a cellulose derived capsule, further wherein, the composition is comprised of one or more different cellulose derived capsules, each comprised of a different cellulose derivative.

276. A sunscreen composition of any one of embodiments 1-275, wherein the inner refractive index of the composition is 1.5-1.7.

277. A sunscreen composition of any one of embodiments 1-275, wherein the inner refractive index of the composition is 1.5-1.7.

278. A sunscreen composition of any one of embodiments 1-275, wherein the inner refractive index of the composition is 1.5-1.9.

279. A sunscreen composition of any one of embodiments 1-275, wherein the inner refractive index of the composition is 1.5-2.2.

280. A sunscreen composition of any one of embodiments 1-275, wherein the inner refractive index of the composition is 1.5-2.4.

281. A sunscreen composition of any one of embodiments 1-275, wherein the inner refractive index of the composition is 1.5-2.6.

282. A sunscreen composition of any one of embodiments 1-275, wherein the inner refractive index of a non-sunscreen active agent in the composition is 1.5-2.7.

283. A sunscreen composition of any one of embodiments 1-275, wherein the inner refractive index of a non organic dispersed with organic sunscreen active agent in the composition is 1.5-2.7.

284. A sunscreen composition of any one of embodiments 1-283, wherein the composition contains cellulose derived capsules of different sizes and the inner refractive index of the composition is greater than 1.5.

285. A sunscreen composition of any one of embodiments 1-283, wherein the composition contains cellulose derived capsules, further wherein, the mixture of cellulose derived capsules contains capsules containing different cellulose derivatives and the inner refractive index of the composition is greater than 1.5.

286. A sunscreen composition of any one of embodiments 1-285, wherein the composition has an overall refractive index of 1.4-2.

287. A sunscreen composition of any one of embodiments 1-286, wherein the cellulose derived capsule wherein 75% or more of the cellulose derived capsules have a diameter of about 300 nm to about 600 nm.

288. A sunscreen composition of any one of embodiments 1-92, wherein the additional agent is a skin whitening active.
289. A sunscreen composition of embodiment 288, wherein the skin whitening agent is a skin lightener and/or a skin bleaching agent.
290. A sunscreen composition of embodiment 288, wherein the skin whitening agent is encapsulated in a cellulose derived capsule.
291. A sunscreen composition of embodiment 288, wherein the skin whitening agent is not encapsulated in a cellulose derived capsule.
292. A sunscreen composition of any one of embodiments 1-92, wherein the additional agent is a cascading antioxidant agent.
293. A sunscreen composition of embodiment 292, wherein the cascading antioxidant agent is emblica or synovia.
294. A sunscreen composition of embodiment 292, wherein the cascading antioxidant agent is encapsulated in a cellulose derived capsule.
295. A sunscreen composition of embodiment 292, wherein the cascading antioxidant agent is not encapsulated in a cellulose derived capsule.
296. A sunscreen composition of any one of embodiments 1-92, wherein the additional agent is a quencher active.
297. A sunscreen composition of embodiment 288, wherein the quencher is Polycrylene.
298. A sunscreen composition of embodiment 288, wherein the quencher is encapsulated in a cellulose derived capsule.
299. A sunscreen composition of embodiment 288, wherein the quencher is not encapsulated in a cellulose derived capsule.
300. A sunscreen composition of any one of embodiments 1-92, wherein the additional agent is an infrared reflective coating.
301. A sunscreen composition of embodiment 288, wherein the infrared reflective coating is encapsulated in a cellulose derived capsule.
302. A sunscreen composition of embodiment 288, wherein the infrared reflective coating is not encapsulated in a cellulose derived capsule.
303. A sunscreen composition of any one of embodiments 2-302, wherein the soap includes a surfactant.
304. A sunscreen composition of any one of embodiments 2-302, wherein the soap does not include a surfactant.
305. A sunscreen composition of any one of embodiments 2-302, wherein the soap is a melt and pour soap.
306. A sunscreen composition of any one of embodiments 2-302, wherein the soap is Castile soap.
307. A sunscreen composition of any of embodiments 1-92, wherein the additional agent is a hindered amine light stabilizer.
308. A sunscreen composition of embodiment 288, wherein the hindered amine light stabilizer is encapsulated in a cellulose derived capsule.
309. A sunscreen composition of embodiment 288, wherein the hindered amine light stabilizer is not encapsulated in a cellulose derived capsule.
310. A sunscreen composition of any one of embodiments 1-309, wherein the sunscreen composition is encapsulated in a cellulose derived capsule and, further wherein, the composition is included in a paint.
311. A sunscreen composition of any one of embodiments 1-309, wherein the sunscreen composition is encapsulated in a cellulose derived capsule and, further wherein, the encapsulated composition is included in a plastic.
312. A sunscreen composition of embodiment 311, wherein the plastic is selected from natural, synthetic or semi-synthetic organic solids that are moldable.
313. A sunscreen composition of embodiment 311, wherein the plastic is selected from thermoplastics and thermosetting plastics.
314. A sunscreen composition of embodiment 313, wherein the thermoplastics and thermosetting plastic are selected from polyethylene, polyamides, polyethylene terephthalate, polyesters, acrylonitrile butadiene styrene, polycarbonate, polyurethane, polypropylene, melamine formadehyde, phenolics, polyetheretherketone, polyetherimide, polylactic acid, polymethyl methacrylate, polytetrafluoroethylene, urea-formaldehyde, polystyrene, polyvinyl chloride and polytetrafluoroethylene.
315. A sunscreen composition of embodiment 311, wherein the plastic is biodegradable.
316. A sunscreen composition of embodiment 311, wherein the plastic is used in a consumer product.
317. A sunscreen composition of embodiment 316, wherein the consumer product is an automobile.
318. A sunscreen composition of embodiment 317, wherein the plastic in the automobile includes vinyl.
319. A sunscreen composition of any one of embodiments 1-318, wherein the sunscreen composition is encapsulated in a cellulose derived capsule and further, wherein, the encapsulated composition is used in a paint.
320. A sunscreen composition of any one of embodiments 1-319, wherein the composition is used in a military, police or other governmental or non-governmental force product.
321. A sunscreen composition of embodiment 320 wherein the military, police or other governmental or non-governmental force product is selected from, sunscreen, paint, clothes, weapons, including, without limitation, weapons containing composite or other synthetic parts, and other military products.
322. A sunscreen composition of embodiment 320 wherein the military, police or other governmental or non-governmental force product includes a reflective agent.
323. A sunscreen composition of embodiment 320 wherein the military, police or other governmental or non-governmental force product includes an agent capable of preventing the detection of infrared radiation by an individual or equipment.

EXAMPLES

Example 1: SPF Testing of Sunscreen Composition

Various sunscreen compositions were tested to determine their SPF value. The test consisted of applying the sunscreen composition by wetting the application site on an individual with 10 ml of water delivered via a syringe followed by application of the test material monograph amount. The lather was then worked in for two minutes. After 30 seconds, the site was rinsed with 20 ml of water and patted dry. The test site was then rubbed using moderate pressure for 20 seconds. The material was allowed to dry for 15 minutes.

TABLE 1

Evaluation of Sun Protection by SPF Determination (FDA)-Static (Rinse/Lather/Rinse/Rub)

| Subject No. | Gender | MED/Hr | $I^a$ (Amps) | Skin Type | MED I $(J/M^2)$ | MED II $(J/M^2)$ | $STD^b$ | SPF Values Static | RLR/RUB |
|---|---|---|---|---|---|---|---|---|---|
| 62-0539 | F | 127.3 | 6.0 | I | 30.33 | 30.33 | 16.30 | 39.60 | 34.50 |
| 48-9212 | F | 129.2 | 6.0 | II | 46.20 | 46.20 | 18.75 | 39.60 | 34.50 |
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 30.00 |
| 76-0164 | M | 125.9 | 6.0 | II | 46.20 | 46.20 | 18.75 | 39.60 | 34.50 |
| 54-1578 | F | 127.1 | 5.4 | II | 46.20 | 46.20 | 16.30 | 39.60 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| Mean (x) | | | | | | | 17.53 | 38.07 | 33.15 |
| Standard Deviation(s) | | | | | | | 1.29 | 2.46 | 2.17 |
| Standard Error | | | | | | | 0.41 | 0.78 | 0.69 |
| Standard Error % of Mean | | | | | | | 2.34 | 2.05 | 2.08 |
| N | | | | | | | 10 | 10 | 10 |
| Upper 5% t Dist. | | | | | | | 2.2622 | 1.8331 | 1.8331 |
| A Values | | | | | | | 0.9228 | 1.4260 | 1.2579 |
| Label SPF | | | | | | | 16 | 36 | 31 |

$^a$I is Intensity of Light Source.
$^b$7% PadO/3% Oxyb.

TABLE 2

Evaluation of Sun Protection by SPF Determination (FDA)-80 Minute Water Immersion

| Subject No. | Gender | MED/Hr | $I^a$ (Amps) | Skin Type | MED I $(J/M^2)$ | MED II $(J/M^2)$ | $STD^b$ | WR Control | SPF Values Static | WR |
|---|---|---|---|---|---|---|---|---|---|---|
| 78-4159 | M | 127.1 | 6.0 | II | 46.20 | 46.20 | 16.30 | 15.00 | 34.50 | 34.50 |
| 72-7479 | M | 128.1 | 6.0 | II | 46.20 | 46.20 | 18.75 | 18.00 | 34.50 | 34.50 |
| Mean (x) | | | | | | | 17.53 | 16.50 | 34.50 | 34.50 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

$^a$I is Intensity of Light Source.
$^b$7% PadO/3% Oxyb.

TABLE 3

Evaluation of Sun Protection by SPF Determination (FDA)-Rinse/Lather/Rinse/Rub-Water Resistant-80 Minute Water Immersion

| Subject No. | Gender | MED/Hr | $I^a$ (Amps) | Skin Type | MED I $(J/M^2)$ | MED II $(J/M^2)$ | $STD^b$ | WR Control | SPF Values Static | WR |
|---|---|---|---|---|---|---|---|---|---|---|
| 78-4159 | M | 126.7 | 5.8 | II | 46.20 | 46.20 | 16.30 | 18.00 | 34.50 | 34.50 |
| 48-1671 | F | 126.2 | 6.0 | II | 30.33 | 30.33 | 18.75 | 15.00 | 34.50 | 30.00 |
| Mean (x) | | | | | | | 17.53 | 16.50 | 34.50 | 32.25 |
| Standard Deviation(s) | | | | | | | 1.73 | 2.12 | 0.00 | 3.18 |
| Standard Error | | | | | | | 1.23 | 1.50 | 0.00 | 2.25 |
| Standard Error % of Mean | | | | | | | 7.02 | 9.09 | 0.00 | 6.98 |
| N | | | | | | | 2 | 2 | 2 | 2 |

$^a$I is Intensity of Light Source.
$^b$7% PadO/3% Oxyb.

TABLE 4

Evaluation of Sun Protection by SPF Determination
(FDA)-Static (Rinse/Lather/Rinse/Rub)

| Subject No. | Gender | MED/Hr | $I^a$ (Amps) | Skin Type | MED I $(J/M^2)$ | MED II $(J/M^2)$ | $STD^b$ | SPF Values Static | RLR/RUB |
|---|---|---|---|---|---|---|---|---|---|
| 62-0539 | F | 127.3 | 6.0 | I | 30.33 | 30.33 | 16.30 | 34.50 | 34.50 |
| 48-9212 | F | 129.2 | 6.0 | II | 46.20 | 46.20 | 18.75 | 34.50 | 34.50 |
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 34.50 |
| 76-0164 | M | 125.9 | 6.0 | II | 46.20 | 46.20 | 18.75 | 39.60 | 34.50 |
| 54-1578 | F | 127.1 | 5.4 | II | 46.20 | 46.20 | 16.30 | 34.50 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| Mean (x) | | | | | | | 17.53 | 36.54 | 33.60 |
| Standard Deviation(s) | | | | | | | 1.29 | 2.63 | 1.90 |
| Standard Error | | | | | | | 0.41 | 0.83 | 0.60 |
| Standard Error % of Mean | | | | | | | 2.34 | 2.27 | 1.79 |
| N | | | | | | | 10 | 10 | 10 |
| Upper 5% t Dist. | | | | | | | 2.2622 | 1.8331 | 1.8331 |
| A Values | | | | | | | 0.9228 | 1.5246 | 1.1014 |
| Label SPF | | | | | | | 16 | 35 | 32 |

$^a$I is Intensity of Light Source.
$^b$7% PadO/3% Oxyb.

TABLE 5

Evaluation of Sun Protection by SPF Determination (FDA)-
80 Minute Water Immersion

| Subject No. | Gender | MED/Hr | $I^a$ (Amps) | Skin Type | MED I $(J/M^2)$ | MED II $(J/M^2)$ | $STD^b$ | WR Control | SPF Values Static | WR |
|---|---|---|---|---|---|---|---|---|---|---|
| 78-4159 | M | 127.1 | 6.0 | II | 46.20 | 46.20 | 16.30 | 15.00 | 34.50 | 30.00 |
| 72-7479 | M | 128.1 | 6.0 | II | 46.20 | 46.20 | 18.75 | 18.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

$^a$I is Intensity of Light Source.
$^b$7% PadO/3% Oxyb.

TABLE 6

Evaluation of Sun Protection by SPF Determination (FDA)-
Rinse/Lather/Rinse/Rub-Water Resistant-80 Minute Water Immersion

| Subject No. | Gender | MED/Hr | $I^a$ (Amps) | Skin Type | MED I $(J/M^2)$ | MED II $(J/M^2)$ | $STD^b$ | WR Control | SPF Values Static | WR |
|---|---|---|---|---|---|---|---|---|---|---|
| 78-4159 | M | 126.7 | 5.8 | II | 46.20 | 46.20 | 16.30 | 18.00 | 34.50 | 30.00 |
| 48-1671 | F | 126.2 | 6.0 | II | 30.33 | 30.33 | 18.75 | 15.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

$^a$I is Intensity of Light Source.
$^b$7% PadO/3% Oxyb.

Table 1 through Table 3 show that following administration of a sunscreen composition to a spot on an adult individual and the subsequent washing and patting dry of the spot on the individual with water, the mean residual SPF from the sunscreen composition applied to the spot on the individual was 38.07 (Table 1), 34.50 (Table 2) and 34.50 (Table 3).

Table 4 through Table 6 show that following administration of a sunscreen composition to a spot on a child and the subsequent washing and patting dry of the spot on the individual with water, the mean residual SPF from the sunscreen composition applied to the spot on the individual was 36.54 (Table 4), 34.50 (Table 5) and 34.50 (Table 6).

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A composition comprising a sunscreen composition, the sunscreen composition comprising:
   a. first flexible cellulose derived capsules encapsulating a first sunscreen composition comprising octocrylene and avobenzone;
   b. second flexible cellulose derived capsules encapsulating a second sunscreen composition comprising octinoxate;
   c. at least 10% (w/v) of one or more anionic surfactant that includes a sulfate;
   d. about 1% (w/v) to about 10% (w/v) of a zwitterionic surfactant that includes a betaine; and
   e. about 0.1% to about 10% of a polyquaternium;
   wherein the first and second flexible cellulose derived capsules consist of i) cellulose, ethylcellulose, hydroxypropylcellulose, hydroxypropylmethylcellulose, carboxymethylcellulose, a derivative of cellulose, a derivative of hydroxypropylcellulose, a derivative of hydroxypropylmethylcellulose, a derivative of ethylcellulose, a derivative of carboxymethylcellulose, or any combination thereof, and ii) the encapsulated first or second sunscreen composition, respectively; and wherein the first and second flexible cellulose derived capsules have a mean diameter of about 200 nm to about 750 nm; and wherein the composition has an SPF of at least about 20.

2. The composition of claim 1, wherein the amount of octinoxate is from about 2% (w/v) to about 10% (w/v).

3. The composition of claim 1, wherein the amount of octinoxate is about 10% (w/v).

4. The composition of claim 3, wherein the amount of octinoxate is about 7.5% (w/v) or less.

5. The composition of claim 1, wherein the amount of octinoxate is at least 5% (w/v).

6. The composition of claim 1, wherein the amount of octocrylene is from about 0.5% (w/v) to about 15% (w/v) and the amount of avobenzone is about 2% (w/v) to about 4% (w/v).

7. The composition of claim 6, wherein the amount of octocrylene is about 10% (w/v) or less and the amount of avobenzone is about 3% (w/v) or less.

8. The composition of claim 1, further comprising cellulose derived capsules comprising a silicone, cellulose derived capsules comprising a fat including a triglyceride, or a combination thereof.

9. The composition of claim 8, wherein the amount of the silicone is from about 2% (w/v) to about 15% (w/v).

10. The composition of claim 8, wherein the amount of the silicone is about 0.1% (w/v).

11. The composition of claim 8, wherein the amount of the silicone is about 1% (w/v).

12. The composition of claim 8, wherein the amount of the silicone is about 0.4% (w/v).

13. The composition of claim 8, wherein the silicone containing compound is dimethyl polysiloxane.

14. The composition of claim 8, wherein the amount of the fat is about 0.1% (w/v).

15. The composition of claim 8, wherein the amount of the fat is about 0.2% (w/v).

16. The composition of claim 8, wherein the amount of the fat is about 0.3% (w/v).

17. The composition of claim 8, wherein the amount of the fat is about 0.4% (w/v).

18. The composition of claim 1, wherein the sulfate comprises sodium lauryl sulfate and sodium laureth sufate.

19. The composition of claim 18, wherein the amount of sodium lauryl sulfate is from about 0.01% (w/v) to about 10% (w/v).

20. The composition of claim 18, wherein the amount of sodium laureth sulfate is from about 0.01% (w/v) to about 10% (w/v).

21. The composition of claim 1, wherein the betaine is cocamidopropyl betaine.

22. The composition of claim 1, wherein the amount of the polyquaternium is from about 0.5% (w/v) to about 5% (w/v).

23. The composition of claim 1, wherein the first flexible cellulose derived capsules have a mean diameter of about 300 nm to about 700 nm, the second flexible cellulose derived capsules have a mean diameter of about 300 nm to about 700 nm, or both the first and second flexible cellulose derived capsules have a mean diameter of about 300 nm to about 700 nm.

* * * * *